US006296852B1

(12) United States Patent
Johnson et al.

(10) Patent No.: US 6,296,852 B1
(45) Date of Patent: *Oct. 2, 2001

(54) RECOMBINANT AVIAN ADENOVIRUS VECTOR

(75) Inventors: Michael A. Johnson, Thornbury; Christopher T. Prideaux, Coburg; Richard J. McCoy, Highton; John W. Lowenthal, Belmont, all of (AU)

(73) Assignee: Commonwealth Scientific and Industrial Research Organisation, Campbell (AU)

( * ) Notice: Subject to any disclaimer, the term of this patent is extended or adjusted under 35 U.S.C. 154(b) by 0 days.

This patent is subject to a terminal disclaimer.

(21) Appl. No.: 09/272,032

(22) Filed: Mar. 18, 1999

Related U.S. Application Data

(63) Continuation-in-part of application No. 08/448,617, filed on Sep. 8, 1995, now abandoned.

(30) Foreign Application Priority Data

Apr. 14, 1993 (AU) .................................................. PL 8297
Apr. 14, 1994 (WO) .................................. PCT/AU94/00189

(51) Int. Cl.$^7$ .......................... A61K 39/12; A61K 39/23; C12N 15/00
(52) U.S. Cl. .................................... 424/199.1; 424/233.1; 424/185.1; 424/184.1; 424/186.1; 424/8.16; 424/204.1; 435/320.1; 435/235.1; 536/23.72; 536/23.1; 935/24
(58) Field of Search .............................. 424/199.1, 184.1, 424/816, 199.2, 204.1, 185.1, 186.1, 233.1, 130.1; 435/320.1, 235.1, 24; 536/23.72, 23.1

(56) References Cited

U.S. PATENT DOCUMENTS 4,769,330  9/1988  Paoletti et al. ..................... 435/172.3
6,083,724  7/2000  Lowenthal et al. ............... 435/69.51

FOREIGN PATENT DOCUMENTS

B-11596/83    7/1983   (AU) .
B-48840/85    5/1986   (AU) .
156 478      10/1985   (EP) .
2031122   *   3/1995   (RU) .
WO 97/40180 * 10/1997  (WO) .

OTHER PUBLICATIONS

Michou et al . Journal of Virology, Feb., 1999, p. 1399–1410, Feb. 1999.*
Zakharchuk et al . Gene, 1995, vol. 161, pp. 189–193, 1995.*
U.S. application No. 09/443,218, filed Nov. 19, 1999, Lowenthal et al.
Sheppard, M. and H. Trist (1992) "Characterization of the Avian Adenovirus Penton Base" *Virology* 188:881–886.
Zhang et al. (1991) "Identification and Characterization of Viral Polypeptides From Type–II Avian Adenoviruses" *Am. J. Vet. Res.* (7)52:1137–1141.
Heine et al. (1991) "Sequence Analysis and Expression of the Host–Protective Immunogen VP2 of a Variant Strain of Infectious Bursal Disease Virus Which Can Circumvent Vaccination With Standard Type I Strains" *Journal of General Virology* 72:1835–1843.

* cited by examiner

*Primary Examiner*—Ali R. Salimi
(74) *Attorney, Agent, or Firm*—Greenlee, Winner and Sullivan, P.C.

(57) ABSTRACT

This invention relates to a recombinant vector comprising a recombinant avian adenovirus incorporating, and capable of expression of at least one heterologous nucleotide sequence. The nucleotide sequence is preferably one which encodes an antigenic determinate of infectious bursal disease virus. The invention further relates to a method of production of recombinant vectors, to methods of preparation of vaccines based on the vectors, to administration strategies and to methods of protecting poultry from disease.

41 Claims, 11 Drawing Sheets

Restriction enzyme maps of FAV CFA 19

FIG. 5

I. The 5' upstream enhancer sequence for the Major Late Promoter (FAVMLP) of Adenovirus CFA20

BASE COUNT     29 A     47 C     67 G     52 T     195 Total

```
  1  TGCTCGTGAC  CAGCCCAAAA  CAAAGCATGC  TATTTGGGTG  GCATAACGTT
 51  TGTTTTCGAC  TTGTTTGTCC  AGGCTTTCTA  GGTGGAGTAC  GGTGAGCGCC
101  TCCGGTGGCG  CGTCGAGGAA  TCGAACGGGC  TTGAATGCGG  TCTCGGTGGC
151  TCGCGAGTGG  GCGGGGTTTG  TTTCTGCCGG  CGGTCGCCCG  TCATC
```

II. FAVMLP TATA box plus sequence leading to the Leader sequence

BASE COUNT     7 A     8 C     8 G     8 T     31 Total

```
  1  TATATAAAGG  CCGCAGGTGA  GCGCTTCTTC  C
```

III. First Leader sequence of Adenovirus CFA20 (FAVLS1)

BASE COUNT     5 A     13 C     13 G     9 T     40 Total

```
  1  AGCTCCTGAT  CGACTTCGGA  GAGGTCTGCC  TCCTCGGCGG
```

IV. Second Leader sequence of Adenovirus CFA20 (FAVLS2)

BASE COUNT     26 A     40 C     38 G     27 T     131 Total

```
  1  GGATCCTGTC  CGAGCCATCC  CGCTTGAGGA  TCGTTTTCGA  CCGCGCGGAC
 51  GAGCCGCTGA  GTGTCTAGCT  CGCCAAAGGC  TTCGACGAAG  AGGTTGAGCC
101  AATCGTCTTC  AGCGAACACT  TCCGATCCAG  G
```

V. Total spliced sequence

BASE COUNT     31 A     54 C     51 G     36 T     169 Total

```
  1  AGCTCCTGAT  CGACTTCGGA  GAGGTCTGCC  TCCTCGGCGG  ATCCTGTCCG
 51  AGCCATCCCG  CTTGAGGATC  GTTTTCGACC  GCGCGGACGA  GCCGCTGAGT
101  GTCTAGCTCG  CCAAAGGCTT  CGACGAAGAG  GTTGAGCCAA  TCGTCTTCAG
151  CGAACACTTC  CGATCCAGG
```

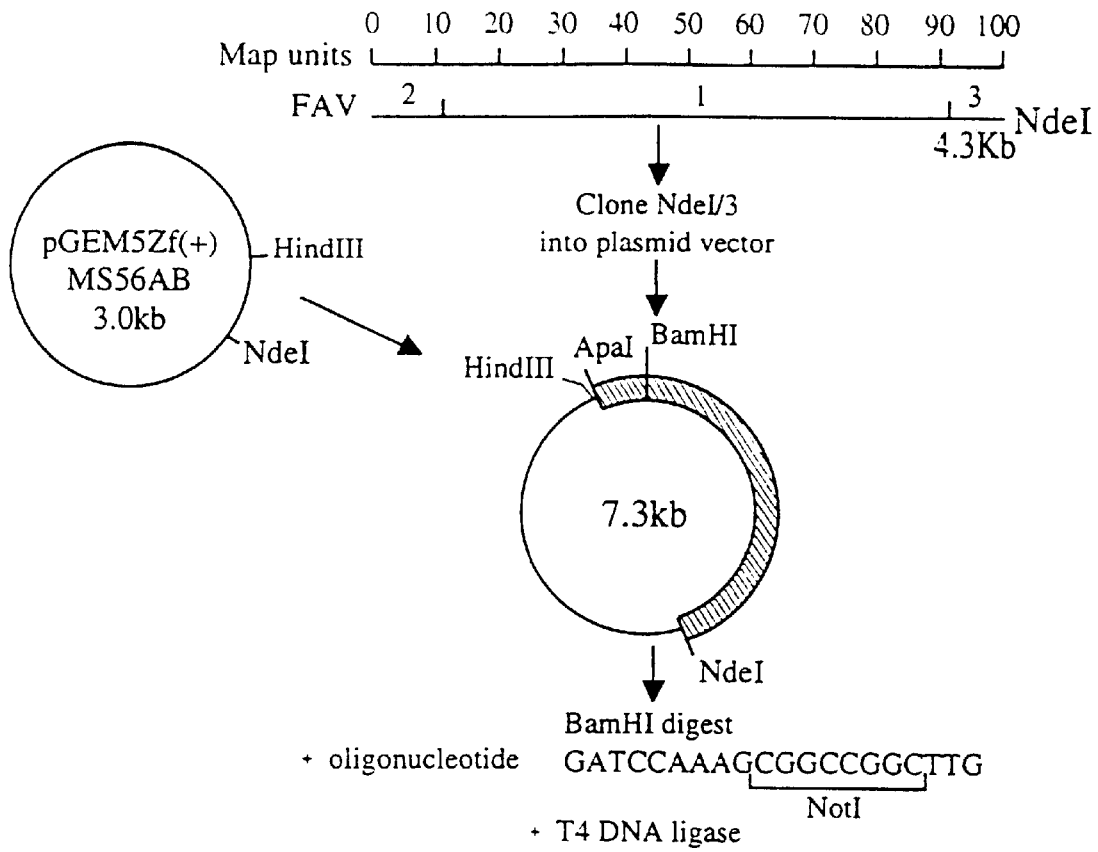
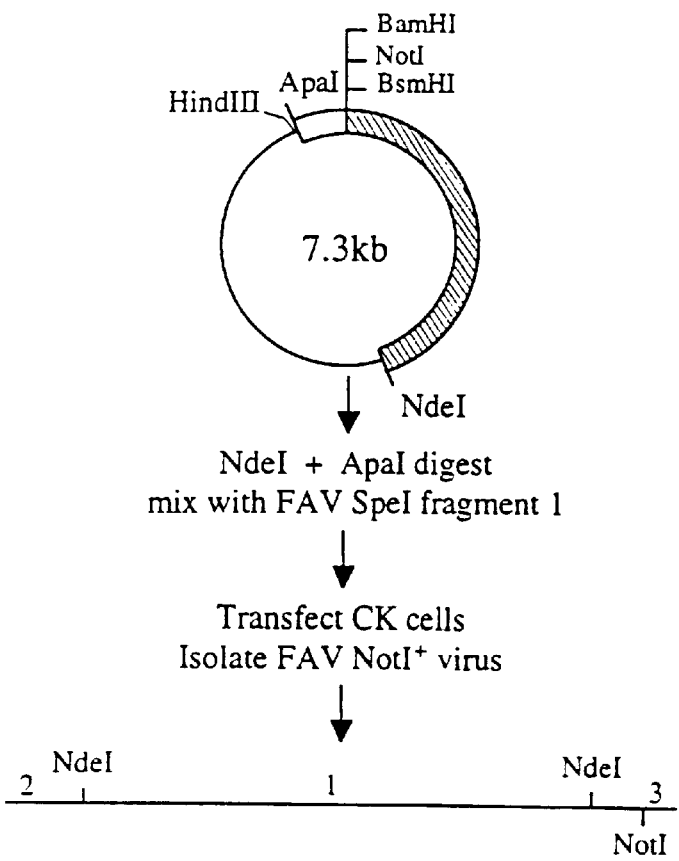
Fig 7.

The major late promoter expression expression cassette containing ChIFNγ inserted into SnaBI-SmaI deletion in the NheI/2 fragment of serotype 8. This fragment was used with SpeI/1 genomic DNA in transfections to produce a recombinant virus which expressed ChIFNγ.

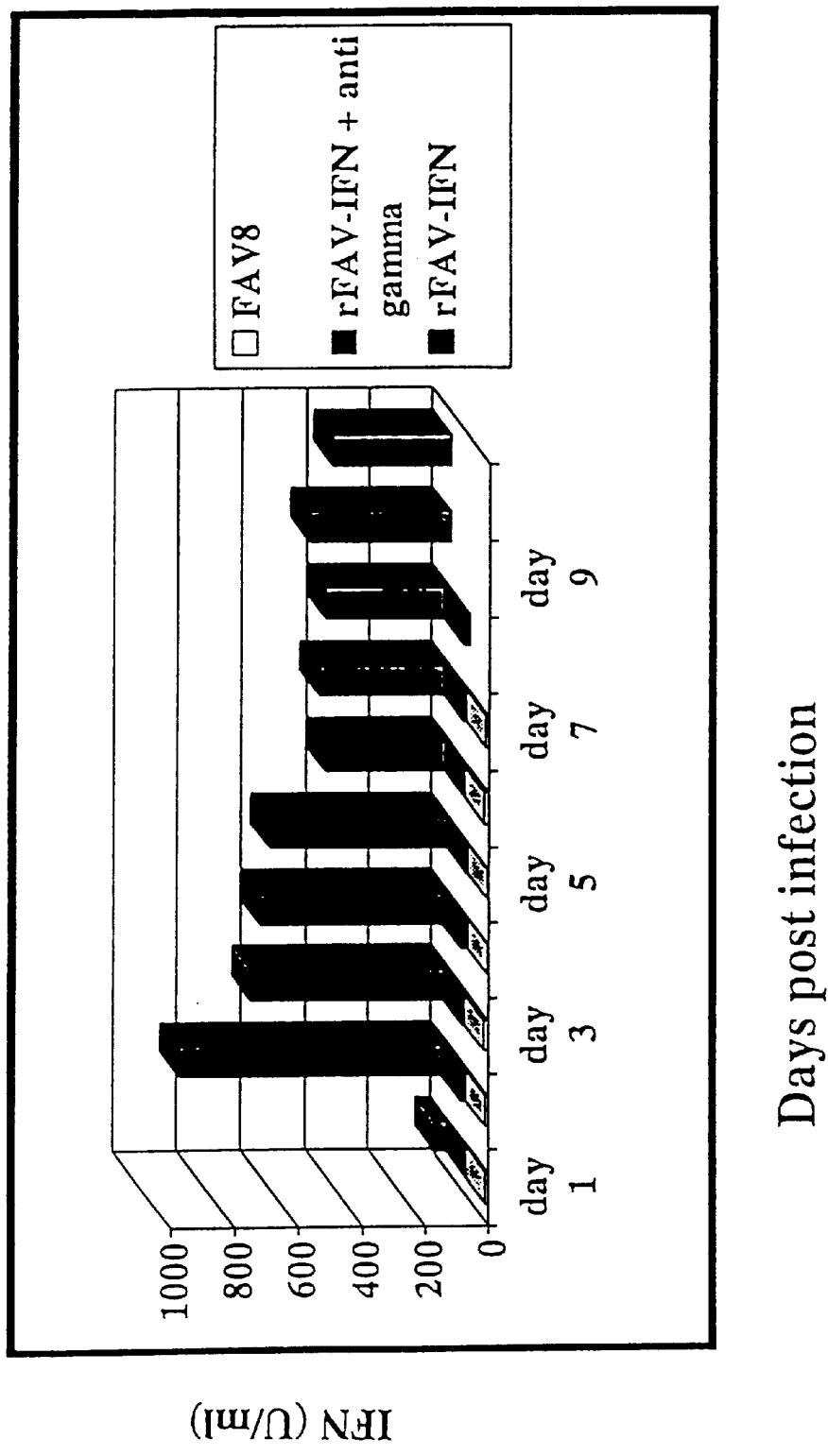
Fig 11. Nitrite assay: detection of ChIFNγ activity

RECOMBINANT AVIAN ADENOVIRUS VECTOR

CROSS REFERENCE TO RELATED APPLICATIONS

This application is a continuation-in-part of U.S. application Ser. No. 08/448,617, filed Sep. 8, 1995, ABN which is a national phase application of International Patent Application No. PCT/AU94/00189, filed Apr. 14, 1994, which claims priority from Australian Patent application No. AU PL 8297, filed Apr. 14, 1993 now abandoned.

FIELD OF INVENTION

This invention relates to delivery vectors for antigen producing genes (heterologous gene sequences) used to generate immune responses in commercial poultry flocks susceptible to decimation by disease. Such vectors are especially useful for the preparation of vaccines which can be easily administered on a large scale to protect poultry flocks against disease. This invention also relates to a method of production of suitable delivery vectors, to methods of preparation of vaccines based on the vectors, to administration strategies and to a method of protecting poultry from disease.

BACKGROUND OF THE INVENTION

The productivity of the intensive poultry industry depends on the control of infectious diseases. In Australia the cost of disease to industry is conservatively estimated at $50 million annually. Whilst diseases can be controlled in part by good hygiene and quarantine measures, the industry must still rely on vaccination to protect flocks. In a commercial situation the difficulty and cost in the administration of suitable preventative or curative agents or adjuvants is caused by the sheer number of poultry to be treated. Thus, vaccines must be cheap, effective and easy to deliver.

Conventionally, vaccines constituting live viral particles have been prepared by virus passage and selection of attenuated forms. Alternatively, killed vaccines were prepared from virulent viruses.

One recent attempt to vaccinate commercial bird flocks against a common viral infection is that described in AU-A-34353/93 (VIROGENETICS CORPORATION). This application describes a recombinant poxvirus such as vaccinia virus or fowlpox virus containing heterologous DNA from the Marek's disease virus which is used as a vaccine to induce an immunological response in a host animal. However, the use of poxviruses has the disadvantage that the immune response of poultry is not sustained sufficiently long enough to generate adequate protection. Particularly, the immunoprotection generated may not be sufficient to protect a bird once maternal antibody has ceased to play a role in antibody mediated immunity.

A different approach has been taken by a group at Medisorb Technologies, Inc., in the U.S. as reported in the journal *Genetic Engineering News* September 1993. This approach used a conventional Salmonella vaccine encapsulated in a biodegradable microsphere based on polylactic-colycolic acid. The approach requires, however that the microsphere be injected into the bird. This approach is not necessarily commercially feasible for large flocks.

It is thus an aim of this invention to provide a delivery vehicle for heterologous sequences of genetic material that is particularly suited to administration on a large scale.

In particular, it is an aim of this invention to provide or enhance means for the generation and/or optimization of antibodies and/or cell-mediated immunity so as to provide protection against infection with common avian diseases, which means is quickly and effectively administered, particularly to large flocks of poultry, that is, to provide or enhance means for the induction of an antibody response and/or cell mediated response in a recipient which affords the recipient protection against infection with common avian diseases. It is an additional aim to provide a process for preparation of a suitable means for the induction of an antibody response and/or cell mediated immune response so as to protect birds against infection with common avian diseases. It is a further aim to provide a protection strategy.

SUMMARY OF INVENTION

The invention provides, in one embodiment, a recombinant avian adenovirus capable of expressing DNA of interest, said DNA of interest being stably integrated into an appropriate site of said recombinant avian adenovirus genome.

In another embodiment the invention provides a recombinant vector comprising a recombinant avian adenovirus which incorporates at least one heterologous nucleotide sequence. Preferably the heterologous nucleotide sequence is capable of expression as an antigenic polypeptide and/or an immunopotentiating molecule.

In another embodiment the invention provides an immunogenic composition comprising at least one recombinant avian adenovirus vector incorporating and expressing at least one heterologous coding sequence and suitable carriers and/or excipients.

It is to be understood that an immunogenic composition includes a vaccine, and it is capable of inducing an antibody response and/or a cell mediated response affording immune protection to the recipient. It is also understood that an immunogenic composition can provide long term protection.

The antigenic polypeptide encoded by the at least one nucleotide sequence is preferably foreign to the host vector.

The recombinant vector may comprise an infectious live recombinant avian adenovirus in which the virion structural proteins are unchanged from those in the native avian adenovirus from which the recombinant avian adenovirus is produced.

The invention is predicated upon the discovery that certain regions of the Fowl Adenovirus genome has unique properties. In particular, the major late promoter and leader sequences are quite dissimilar to equivalent regions in Adenoviruses previously characterized. It has surprisingly been discovered that the leader sequence is a dipartite leader sequence. It is also surprising, based on knowledge of human adenoviruses that there are nonessential regions in the fowl Adenovirus genome which do not correspond to those characterized previously in other Adenoviruses thus making this virus particularly suited to delivery of heterologous sequences.

This invention is further predicated on the discovery that the Avian adenovirus generates a prolonged response in poultry thus making it well suited as a vaccine vehicle. Furthermore, the existence of a number of serotypes of varying virulence allows the selection of a vaccine vehicle suited to the level of immune response required.

Adenoviruses are a large and diverse family, having been isolated from many living species, including man and other mammals, as well as a variety of birds, particularly chickens [Wigand, R., Gelderblom, H. and Ozell, M. (1977) Biological and biophysical characteristics of mouse adenovirus, strain FL. Arch, *Virol.* 54:131–142]. As a result, adenoviruses have been separated into two different genera, one group has a mammalian host range (Mastadenoviradae) and the other an avian host range (Aviadenoviradae). Because the avian adenovirus serotypes are only very distantly related to mammalian adenoviruses a knowledge of the latter is only partially instructive in relation to the former. The avian adenoviruses show only very limited DNA homology with human adenoviruses [Alestrom, P., Stenlund, A., Li, P., Bellet, A. J. D. and Pettersson, U. (1982) Sequence homology between avian and human adenoviruses. *J. Virol.* 42:306–310] with fowl adenovirus ("FAV") genomes being some 10 kilobases larger than the human adenovirus genome. The classification of these viruses as adenoviruses is based solely on morphological and structural similarities.

The genus Aviadenovirus is currently divided into five species groups: fowl, turkey, goose, pheasant and duck adenoviruses. Fowl adenoviruses were first recognized in the 1950s when they were isolated as a consequence of using embryonated eggs and cell cultures with FAV [Van Den Ende, M., Don, P. A. and Kipps, A. (1949) The isolation in eggs of a new filterable agent which may be the cause of bovine lumpy skin disease. *J. Gen. Micro.* 3:174–182; Yates, V. J. and Fry, D. E. (1957) Observations on a chicken embryo lethal orphan (CELO) virus (serotype 1). *Am. J. Vet. Res.* 18:657–660]. However, the only fowl adenovirus upon which some molecular study has been undertaken is the oncogenic FAV, chicken embryo lethal orphan (CELO). The CELO virus genome is almost 30% longer than that of human adenoviruses (HAV) [Laver, W. G., Bandfield-Younghusband, H. and Wrigley, N. G. (1971) Purification and properties of chick embryo lethal orphan virus (an avian adenovirus). *Virol* 45:598–614]. CELO virus is composed of at least 11–14 structural proteins [Yasue, H. and Ishibashi, M. (1977) Chick embryo lethal orphan (CELO) virus-induced early and late polypeptides. *Virol.* 78:216–233; Li, P., Bellet, A. J. D. and Parish, C. R. (1984) DNA-binding proteins of chick embryo lethal orphan virus: Lack of complementation between early proteins of avian and human adenoviruses. *J. Gen. Virol.* 65:1817–1825] and is structurally similar to HAV which is composed of 10–14 structural proteins [Maizel, J. V. (Jr.), White, D. O. and Scharff, M. (1968) The polypeptides of adenovirus. I. Evidence for multiple protein components in the virion and a comparison of types 2, 7A and 12. *Virol.* 36:115–125; Ishibashi, M. and Maizel, (Jr.), J. V. (1974) The polypeptides of adenovirus V. Young virions, structural intermediate between top components and aged virions. *Virol.* 57:409–424]. The only morphological difference apparent between them is the additional FAV fiber. Even allowing for a second fiber gene a considerable amount of 'excess' DNA remains to be accounted for in the genome of FAV when compared to the HAV.

DNA cross-hybridization studies demonstrated only very limited homology between HAV and FAV [Alestrom, P., Stenlund, A., Li, P., Bellet, A. J. D. and Pettersson, U. (1982) Sequence homology between avian and human adenoviruses. *J. Virol.* 42:306–310]. However, in spite of this and the lack of immunological relatedness, the amino acid composition of CELO virus and HAV hexons but not the gene sequence were found to be similar [Laver, W. G., Bandfield-Younghusband, H. and Wrigley, N. G. (1971) Purification and properties of chick embryo lethal orphan virus (an avian adenovirus). *Virol.* 45:598–614]. Other similarities noted include: the presence of terminal repeat sequences at either end of the genome [Alestrom, P., Stenlund, A., Li, P., Bellet, A. J. D. and Pettersson, U. (1982) Sequence homology between avian and human adenoviruses. *J. Virol.* 42:306–310; Sheppard, M. and Erny, K. M. (1989) DNA sequence analysis of the inverted terminal repeats of a non-oncogenic avian adenovirus. *Nuc. Acids Res.* 17:3995], the synthesis of low molecular weight virus associated ("VA") RNAs [Larsson, S., Bellet, A. and Akusjarvi, G. (1986) VA RNAs from avian and human adenoviruses: dramatic differences in length, sequence, and gene location. *J. Virol.* 58:600–609] and sharing of at least one non-structural protein; the DNA binding protein (DBP) [Li, P., Bellet, A. J. D. and Parish, C. R. (1984) DNA-binding proteins of chick embryo lethal orphan virus: Lack of complementation between early proteins of avian and human adenoviruses. *J. Gen. Virol.* 65:1817–1825].

At face value these findings suggest strong similarities exist between FAV and HAV. However, the terminal repeat sequences of FAV are much shorter in length and, unlike HAV, the length of terminal repeats did not differ in a comparison between one oncogenic and one nononcogenic FAV [Sheppard, M. and Erny, K. M. (1989) DNA sequence analysis of the inverted terminal repeats of a non-oncogenic avian adenovirus. *Nuc. Acids Res.* 17:3995]. Secondly, the VA RNA genes of FAV differ from their HAV counterparts in their chromosomal location, direction of transcription and primary sequence [Larsson, S., Bellet, A. and Akusjarvi, G. (1986) VA RNAs from avian and human adenoviruses: dramatic differences in length, sequence, and gene location. *J. Virol.* 58:600–609]. Finally, the DBP of FAV which initiates transcription by interacting with the E1A genes, fails to recognize the E1A genes of HAV [Li, P., Bellet, A. J. D. and Parish, C. R. (1984) DNA-binding proteins of chick embryo lethal orphan virus: Lack of complementation between early proteins of avian and human adenoviruses. *J. Gen. Virol.* 65:1817–1825].

Fowl adenoviruses are common within poultry flocks, and to date 11 distinct serotypes have been recognized [McFerran, J. B. and Connor, T. J. (1977) Further studies on the classification of fowl adenoviruses. *Av. Dis.* 21:585–595]. While all of these serotypes appear to be widely disseminated throughout the world, epidemiological surveys show that in a given geographical location certain serotypes appear to predominate. For example, in America the most common serotypes encountered are 1, 4, 5, 7 and 9 [Cowen, B., Mitchell, G. B. and Calnek, B. W. (1978) An adenovirus survey of poultry flocks during the growing and laying periods. *Av. Dis.* 22:115–121; Yates, V. J., Rhee, Y. O., Fry, D. E., El Mishad, A. M. and McCormick, K. J. (1976) The presence of avian adenoviruses and adeno-associated viruses in healthy chickens. *Av. Dis.* 20:146–152]. Surveys of clinically diseased Australian flocks have identified types 1 and 4 [Boyle, D. B. and McFerran, J. B. (1976) Avian adenoviruses isolated from poultry in Queensland, *Aus. Vet. J.* 52:587–589] and, more recently types 6, 7 and 8 [Reece, R. L., Barr, D. A., Grix, D. C., Forsyth, W. M. Condron, R. J. and Hindmarsh, M. (1986) Observations on naturally occurring inclusion body hepatitis in Victorian chickens. *Aust. Vet. J.* 63:201–202] as the most prevalent serotypes.

When choosing appropriate FAV for development as live vectors to deliver vaccines to bird flocks, it is important to take into account the natural prevalence of serotypes. Those serotypes not commonly encountered in the field have an obvious advantage over those to which flocks are frequently exposed and to which they may have developed immunity.

A further consideration is the ability of the vector to remain active in the bird beyond the period within which maternal antibodies protect the bird immediately post-hatching.

Other important considerations in choosing potential FAV vectors are pathogenicity and immunogenicity. Preferably live vector viruses should be highly infectious but non-pathogenic (or at least stably attenuated) such that they do not themselves adversely affect the target species.

The oncogenic nature of serotype-1 FAV has been demonstrated [Sarma, P. S., Huebner, R. J. and Lane, W. T. (1965) Induction of tumors in hamsters with an avian adenovirus (CELO). Science 149: 1108] and for this reason this group of FAV is not favored for vector development.

Preferred candidates for use as vaccine vectors are non-pathogenic isolates FAV CFA20 (serotype 10), CFA15 (serotype 10) and CFA 40 (serotype 8). The CFA20 virus is the more preferred vector candidate because it is clinically safe and because it represents a serotype apparently uncommon in Australian and American poultry flocks. This is an important consideration as it reduces the possible problems associated with prior exposure. However, pre-existing antibody does not preclude use of a common serotype as a vaccine candidate. FAV CFA15 and CFA19 (serotype 9) are also suitable candidates for vector development. Other serotypes may also be useful. It is notable that more virulent strains produce a greater antibody response.

Heterologous nucleotide sequences which may be incorporated into nonessential regions of the viral genome and which may encode the antigenic determinants of infectious organisms against which the generation of antibodies or cell-mediated immunity is desirable may be those expressing antigenic determinants of intestinal infections caused by parasites; for example, coccidial infections or respiratory viruses, for example, infectious bronchitis virus. Other infectious organisms against which immunity may be desirable include those that target internal organs such as the bursa of Fabricius, for example, infectious bursal disease virus (IBDV).

Identification of sites suitable for the insertion of heterologous sequences and monitoring of the expression of those sites may be made using a Thymidine Kinase (TK) selection method. This method of selection is premised on the fact that avian adenoviruses (wild type) do not have TK coding sequences. Insertion of a TK expression cassette into the FAV genome can be combined with selection for a recombinant expressing TK during transfection/homologous recombination using chemical selection methods [MTAGG: Boyle and Coupar (1986)]. Identification of a FAV 1X recombinant demonstrates that a deletion may be made at the site of insertion of the TK expression cassette. Nonessential regions using this selection method have been identified in the right hand end of the FAV genome. This method may also be used to identify other nonessential regions for example, in the left hand end of the FAV genome without undue experimentation. The method may also be used to identify essential regions of the FAV genome without the need for undue experimentation.

Other selectable marker systems can be used in an analogous manner to the TK Selection method to identify sites suitable for insertion of heterologous sequences.

Heterologous nucleotide sequences which may be incorporated include the antigenic determinants of the agents of Newcastle Disease
Marek's Disease
Egg Drop Syndrome
Inclusion Body Hepatitis
Infectious Laryngotracheitis
Mycoplasma
Chicken Anaemia Agent (aplastic anaemia)
Avian Influenza
Avian Encephalomyelitis
Infectious Bronchitis Virus Heterologous nucleotide sequences which encode the antigenic determinants of various bacterial agents such as Salmonella, Escherichia, Clostridium and Pasteurella may also be incorporated.

Heterologous nucleotide sequences more preferred for incorporation in the vectors of the invention are those expressing antigenic determinants of the causative agents of coccidiosis, Newcastle Disease, Marek's Disease, Infectious Bronchitis Virus and Infectious Laryngotracheitis.

It is also envisaged the heterologous sequences incorporated may be immunopotentiator molecules such as cytokines or growth promoters, for example insulin like growth factors (IGF) or interferons (IFN).

The type of immune response stimulated by candidate vectors may affect the selection of heterologous nucleotide sequences for insertion therein. FAV isolates CFA20, CFA15 and CFA40 may induce mucosal immunity and are thus more suitable for inventions of the intestines or respiratory system. FAV isolates such as CFA19 which induces a strong serum antibody response may be more suitable for use against diseases of the organs of poultry because of their ability to penetrate beyond the gut of the bird.

The DNA of interest which may comprise heterologous genes coding for antigenic determinants or immunopotentiator molecules may be located in at least one nonessential region of the viral genome.

Nonessential regions of the viral genome which may be suitable for the purposes of replacement with or insertion of heterologous nucleotide sequences may be non-coding regions at the right terminal end of the viral genome and/or the left terminal end of the viral genome. Preferably this region is located at the right end of the genome at map units 70 to 100. More preferably, this region is located at the right hand end at map units 60 to 100.

The heterologous gene sequence may be associated with a promoter and leader sequence in order that the nucleotide sequence may be expressed in situ as efficiently as possible. Preferably the heterologous gene sequence is associated with the avian adenoviral major late promoter and splice leader sequence.

The major late promoter lines near 16–17 map units on the adenovirus genetic map and contains a classical TATA sequence motif. [Johnson, D. C., Ghosh-Condhury, G., Smiley, F. R., Fallis, L. and Graham, F. L. (1988) Abundant expression of herpes simplex virus glycoprotein gB using an adenovirus vector. *Virology* 164:1–14].

The splice leader sequence of the avian adenovirus isolates under consideration is a dipartite sequence spliced to late genes.

The heterologous gene sequence may also be associated with a polyadenylation sequence.

Instead of the avian adenoviral major late promoter, any other suitable eukaryotic promoter can be used.

For example, those of SV40 virus, cytomegalovirus (CMV) or human adenovirus may be used.

Processing and polyadenylation signals other than those of avian adenoviruses may also be considered, for example, that of SV40.

In a further aspect of the invention there is provided a recombinant vaccine for induction of an antibody response and/or cell mediated response so as to provide or enhance protection against infection with an infectious organism in birds, the vaccine comprising at least one recombinant avian adenovirus vector incorporating at least one heterologous nucleotide sequence formulated with suitable carriers and excipients. Preferably the nucleotide sequence is capable of expression as an antigenic polypeptide.

The antigenic polypeptide encoded by the at least one nucleotide sequence is preferably foreign to the host vector. At least one nucleotide sequence may be associated with a promoter/leader and a poly A sequence.

The recombinant vaccine may include live recombinant avian adenovirus vector in which the virion structural protein are unchanged from that in the native avian adenovirus from which the recombinant avian adenovirus is produced.

Preferred vector candidates for use in the recombinant vaccine are FAV isolates CFA20 (serotype 10), CFA40 (serotype 8), CFA15 (serotype 10) and CFA19 (serotype 9). Use of other serotypes is possible, depending on the poultry type, its existing immunity and its environment.

If the vaccine is to be used to optimise protection against disease, suitable heterologous nucleotide sequences may be those of immunopotentiators such as cytokines or growth promoters.

The vaccines may comprise other constituents, such as stabilizers, excipients, other pharmaceutically acceptable compounds or any other antigen or part thereof. The vaccine may be in the form of a lyophilized preparation or as a suspension, all of which are common in the field of vaccine production.

A suitable carrier for such a vaccine may be isotonic buffered saline.

In a further aspect of the invention, there is provided a method of preparing a vaccine for induction of an antibody response and/or optimization of antibodies and/or cell-mediated immune response so as to induce or enhance protection against an infectious organism in a bird, which comprises constructing a recombinant avian adenovirus vector incorporating at least one heterologous nucleotide sequence, and placing said recombinant avian adenovirus vector in a form suitable for administration. Preferably the nucleotide sequence is capable of expression as an antigenic polypeptide although it may also be an immunopotentiator. The nucleotide sequence is conveniently foreign to the host vector.

More preferably the nucleotide sequence is associated with promoter/leader and poly A sequences.

The form of administration may be that of an enteric coated dosage unit, an inoculum for intraperitoneal, intramuscular or subcutaneous administration, an aerosol spray, by intraocular drop or intranasal application. Administration in the drinking water, in feed pellets or in ovo is also possible.

The more preferred mode of administration is as an aerosol spray.

In another aspect of the invention, there is provided a method of producing an avian adenovirus vaccine vector which comprises inserting into an avian adenovirus at least one heterologous nucleotide sequence. Said heterologous nucleotide sequence is preferably capable of expression as an antigenic polypeptide.

Preferably the antigenic polypeptide encoded by the inserted nucleotide sequence is foreign to the host vector.

More preferably the heterologous nucleotide sequence is associated with promoter/leader and poly A sequences.

In one preferred method of construction of a vaccine vector, a restriction enzyme site preferably being one that does not cleave the host virus genome selected for construction, is inserted into a nonessential and preferably non-coding region of the host virus genome. The recombinant viral genome thus is provided with a unique restriction enzyme site in a nonessential region to allow insertion of heterologous nucleotide sequences by simple restriction enzyme cleavage and ligation. This method has the added advantage of enabling, if preferred, deletion of portions of the nonessential region to allow the insertion of greater portions of DNA.

By this method a DNA expression cassette containing an appropriate FAV promoter with a foreign gene sequence as well as leader sequences and polyadenylation recognition sequences can be constructed with the unique restriction enzyme sites flanking the cassette enabling easy insertion into the FAV genome.

In an alternative method of construction of a suitable vector the nonessential region to be altered to incorporate foreign DNA could be constructed via homologous recombination. By this method the nonessential region is cloned, a portion of it is deleted, and foreign DNA together with promoter, leader and polyadenylation sequences is inserted, preferably by homologous recombination between flanking sequences. By this method also, deletion of portions of the nonessential region is possible to create extra room for larger DNA inserts that are beyond the normal packaging constraints of the virus.

In another aspect of the invention there is provided strategies for administration of the vaccines of the invention.

The vaccine is preferably administered by aerosol spray since airborne spread is a natural route of FAV dissemination.

In one strategy according to the invention, FAV vector based vaccines may be administered as 'cocktails' comprising two or more virus vectors carrying different foreign genes or immunopotentiators.

In a preferred vaccination strategy of the invention, the 'cocktail' or simultaneous strategy, a vaccine based on both FAV isolates CFA19 and CFA20 is used.

In an alternative strategy according to the invention, FAV vector based vaccines may be administered consecutively of each other to either administer booster vaccines or new vaccines at some stage subsequent to initial FAV vaccination. The vaccines used are preferably based on heterologous FAV isolates.

In a preferred version of the "consecutive" strategy, vaccines based on isolates serotypically unrelated are selected so as to achieve maximum protection against infection. In one example of such a strategy a vaccine based on FAV isolate CFA20 is administered subsequently or prior to vaccination with a vaccine based on FAV isolate CFA19.

Poultry are conveniently inoculated with vector vaccines according to the invention at any age. Where chickens are concerned, broilers may be vaccinated at one day old, breeders and layers may be vaccinated regularly up to point of lay and thereafter.

Preferably according to either the consecutive strategy or the cocktail strategy, poultry are vaccinated while still not fully immunocompetent. More conveniently, day-old birds can be vaccinated for protection against re-infection after a period of four weeks subsequent to initial vaccination.

In a further embodiment of the invention there is provided a method for producing an immune response in a bird comprising administering to the bird an effective amount of a recombinant vaccine according to the invention. An effective amount as referred to throughout the present description is an amount sufficient to elicit an immune response, preferably at least $10^4 TCID_{50}$ per dose, but within the range of $10^3$–$10^7 TCID_{50}$ per dose depending on the method of application.

The vaccine of the invention may of course be combined with vaccines against other viruses or organisms such as Marek's Disease virus, Newcastle Disease virus or infectious bronchitis prior to or at the time of its administration.

The vaccine may be directed against respiratory and intestinal infections caused by a variety of agents. In order to direct the vaccine against a specific infectious organism, heterologous gene sequences encoding the antigenic determinants of those infectious organisms may be incorporated into nonessential regions of the genome of the avian adenovirus comprising the vector.

In a preferred aspect of this embodiment of the invention, administration is by aerosol spray.

Methods for construction and testing of recombinant vectors and vaccines according to this invention are well known to those skilled in the art. Standard procedures for endonuclease digestion, ligation and electrophoresis were carried out in accordance with the manufacturer's or supplier's instructions. Standard techniques are not described in detail and will be well understood by persons skilled in the art.

BRIEF DESCRIPTION OF THE DRAWINGS

FIG. 5 shows the sequences of the upstream enhancer sequence for the major late promoter and splice leaders 1 and 2.

FIG. 7 illustrates a method of construction of a FAV vector.

FIG. 11 illustrates results of biological assays for chicken gamma interferon produced by recombinant FAV.

PREFERRED EMBODIMENTS

Aspects of preferred embodiments of the invention based on FAV isolates CFA15, 19, 20 and 40 will now be described. Whilst these four isolates have been selected because of their low pathogenicity and/or high immunogenicity, it will be appreciated that other isolates of avian adenovirus may also be suitable for construction of vaccine vectors provided that the criteria for selection described hereinbefore are met.

Table 1 illustrates the suitability of several other isolates of varying serotype. Pathogenicity was tested by administration of $10^6$ pfu of virus injected in a 0.5 ml volume via the intraperitoneal route. Surviving chickens were killed at 8–10 days and tissue samples taken for histology and virus re-isolation.

Figure 1:
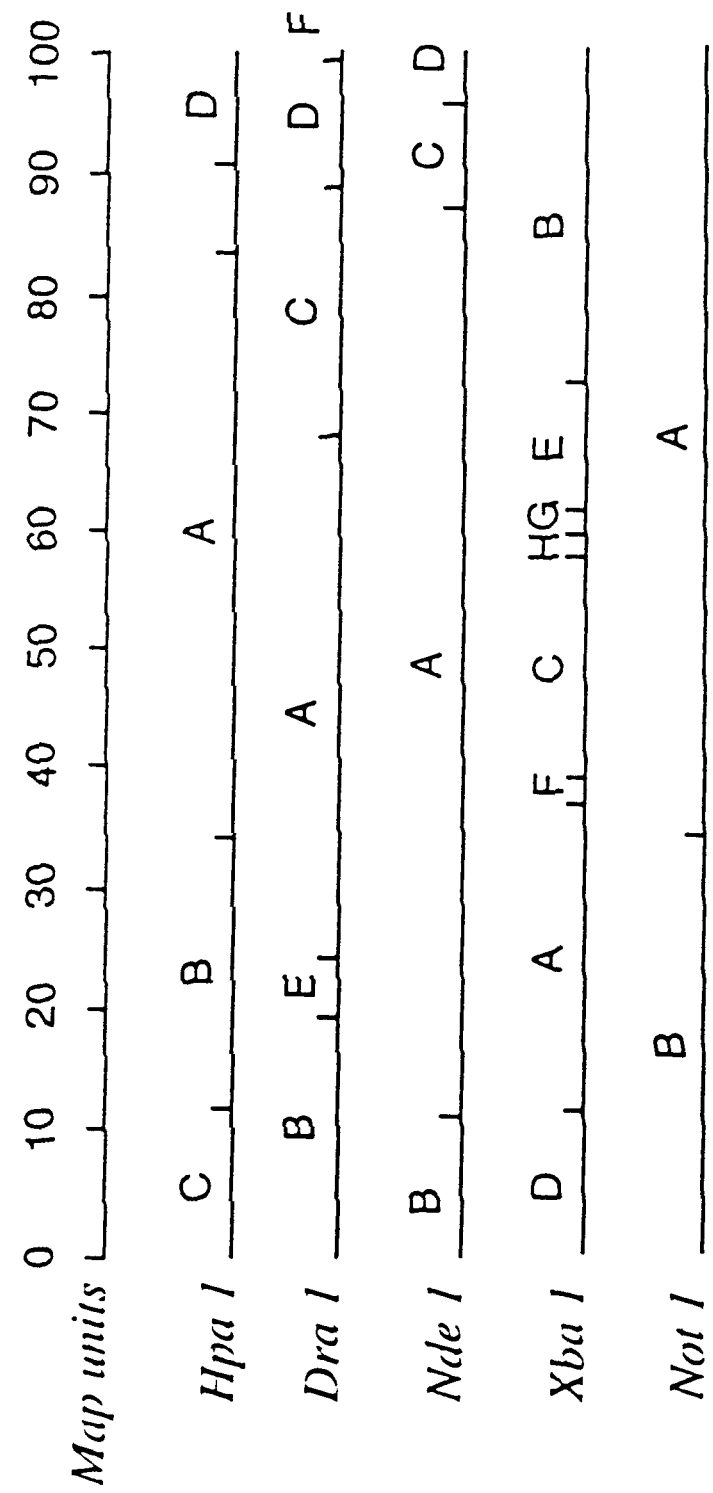
FIG. 1 illustrates the DNA restriction endonuclease map of the entire genome of FAV-CFA15.
Figure 2:
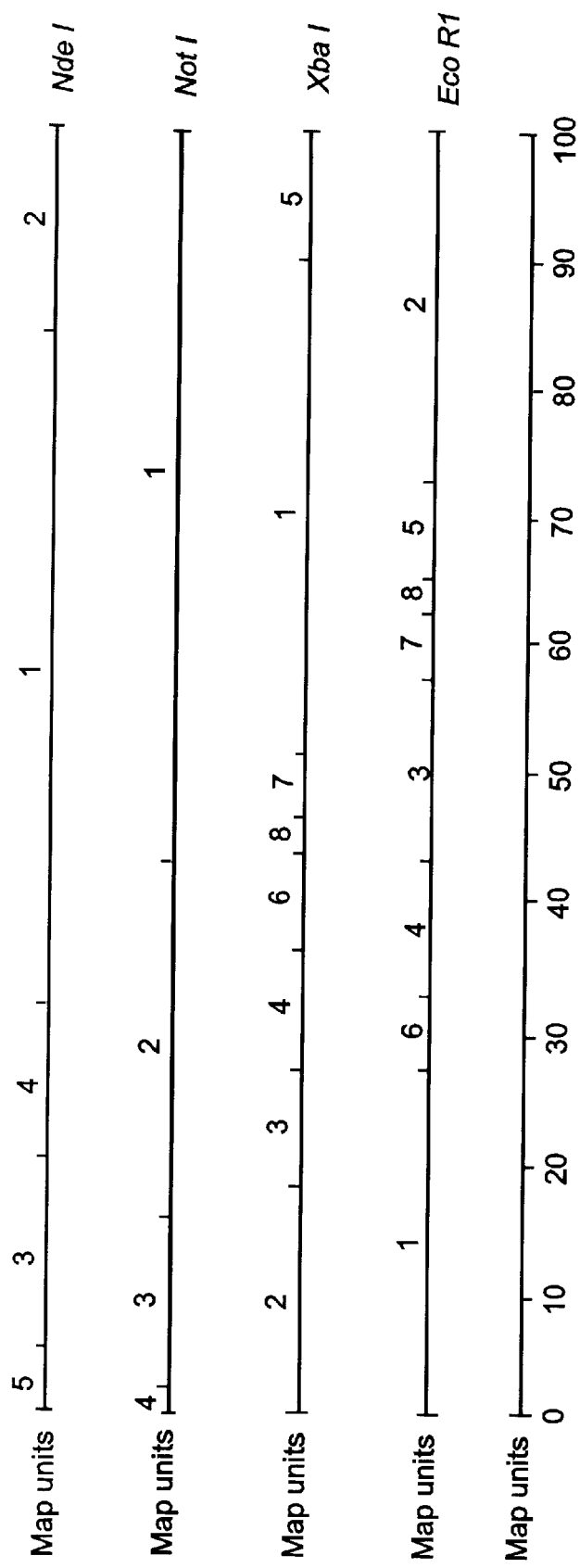
FIG. 2 illustrates the DNA restriction endonuclease map of the entire genome of FAV-CFA19.
Figure 3:
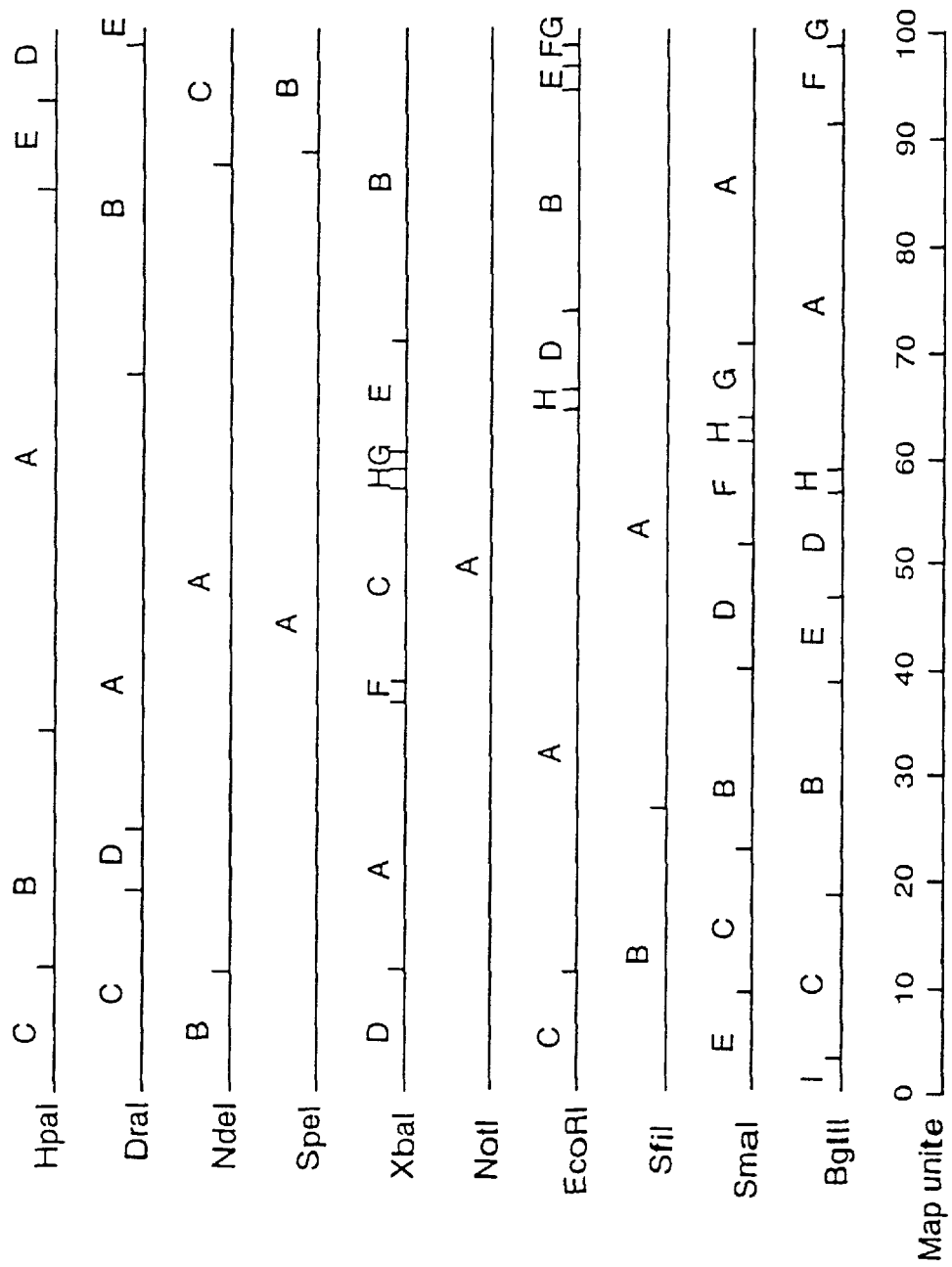
FIG. 3 illustrates the DNA restriction endonuclease map of the entire genome of FAV-CFA20.

The genomes of the selected isolates FAV CFA15, 19 and 20 were characterized by conventional methods. The DNA restriction endonuclease maps of the entire genome of each are illustrated respectively in FIGS. 1, 2 and 3. Map units are given (1 mu=0.45 Kb) and the genomes are oriented left to right. By convention adenovirus genomes are normally oriented such that the terminal region from which no late mRNA transcripts are synthesised is located at the left end. The enzyme used to generate each map is indicated at the edge of each map.

DNA restriction endonuclease maps have been published for CFA40 [Pallister and Sheppard (1996) Comparison by restriction enzyme analysis of three fowl adenoviruses of varying pathogenicity. *Veterinary Microbiology* 48:155–163].

Characterization of Viral Genomes

TABLE 1

Pathogenicity of 16 FAV representing 8 distinct and 1 intermediate serotype, for day-old Specific Pathogen Free (SPF) chickens injected via the intraperitoneal (IP) route.

| Virus | Serotype | Mortalities[a] % | Virus recovery[b] | % Weight reduction[c] |
|---|---|---|---|---|
| CFA3 | 8 | 0 | + | 0 |
| CFA13 | 6 | 0 | + | 8 |
| CFA20 | 10 | 0 | + | 8 |
| CFA15 | 10 | 0 | + | 0 |
| CFA2 | 1 | 5 | + | 0 |
| CFA7 | 1 | 5 | + | 0 |
| CFA11 | 2 | 10 | + | 9 |
| CFA17 | 8 | 15 | + | 1 |
| CFA19 | 9 | 18 | + | 17 |
| CFA10 | 7 | 20 | + | 16 |
| CFA4 | 7 | 35 | + | 25 |
| CFA9 | 1 | 50 | + | 25 |
| CFA5 | 8 | 65 | + | 25 |
| CFA22 | 7/8 | 100 | + | —[d] |
| CFA24 | 7/8 | 100 | + | —[d] |
| CFA40 | 8 | 100[e]/0[f] | + | —[d/o g] |

[a]twenty, day-old chickens each received $10^6$ pfu of virus and subsequent deaths were recorded over an 8 day period
[b]virus recovery was attempted from caecal tonsil tissue
[c]weight reduction was calculated by comparing the average weight of infected birds with that of uninfected control birds
[d]None survived long enough to determine weight reduction
[e]100% in SPF day old chickens
[f]0% commercial broilers with existing maternal antibody against serotype 8
[g]none in commercial broilers with existing maternal antibody against serotype 8

Characterization of Major Late Promoter (MLP) and Splice Leader Sequences (LS) of CFA20

Identification and cloning of the FAV MLP

By use of DNA restriction enzyme and genetic maps of the FAV serotype 10 (CFA20) genome, a region was located that was believed to contain the MLP and leader sequences. Three DNA fragments DraI fragment 4(3.0 kb), HpaI/DraI fragment (2.8 kb) and a DraI/HpaI fragment (4.5 kb) (FIG. 4) were all cloned individually into plasmid vectors. These DNAs were subcloned into M13mp18 and mp19 and sequenced. (FIG. 5).

The MLP promoter sequence was identified as containing a classical TATA sequence, the only one in the region sequenced, as well as potential upstream factors and was subsequently confirmed by the location of the leader sequence and the transcriptional start site.

Figure 4:
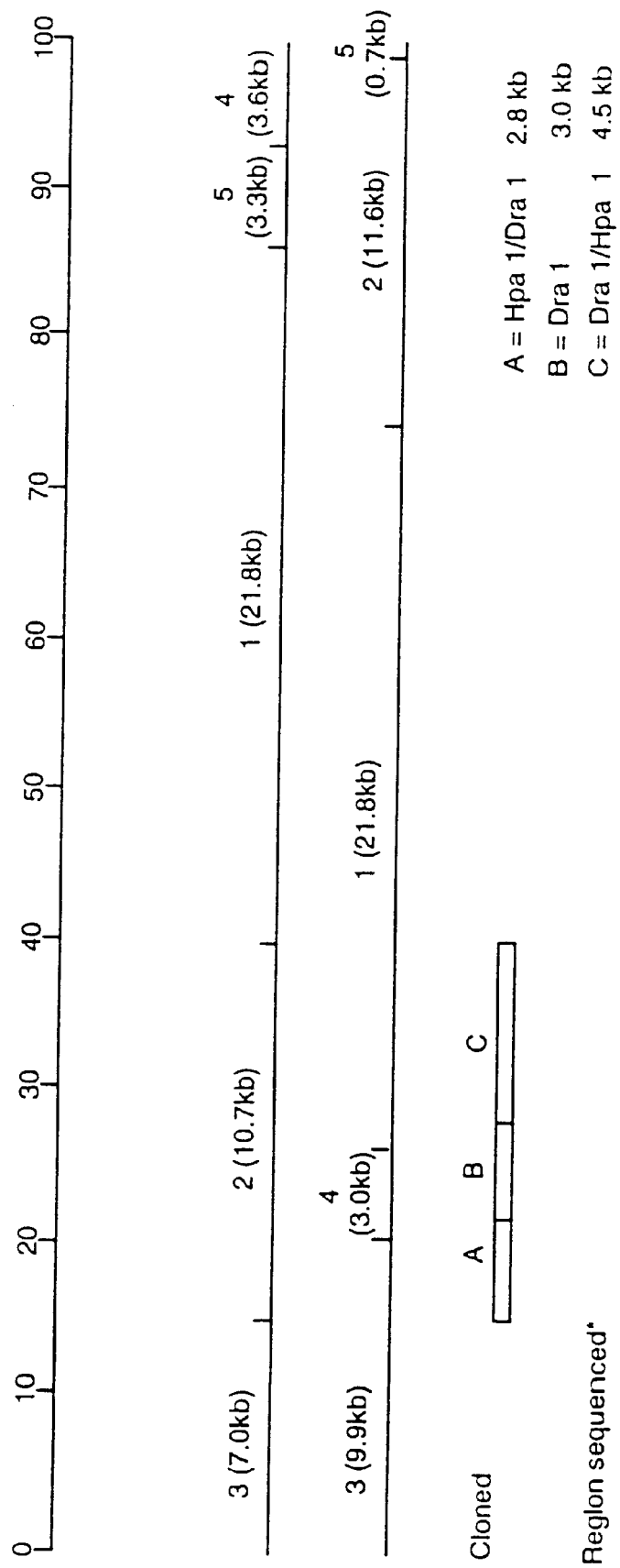
FIG. 4 illustrates the sequence characterization and cloning of the major late promoter and splice leader sequences of CFA20.

FIG. 4 illustrates the sequence characterization and cloning of the major late promoter and splice leader sequences of CFA20. Specifically, shown are the HpaI restriction endonuclease maps of FAV CFA20. The regions cloned (☐) and sequenced (—) are indicated.

In order to determine the structure and sequence of the leader sequence spliced to late mRNA, chicken kidney cells were infected with FAV and the infection was allowed to proceed until late in the infection cycle (usually 24–32 hr p.i.). At this time total RNA was purified from the infected cells using RNAzol B solution (Breseatec, Australia). The isolated RNA was precipitated with isopropanol and stored at −70° in 50 µl aliquots until required. Poly A (mRNA) was isolated from total RNA by the use of the Poly AT tract System (Promega, USA). The isolated mRNA was used in cDNA production.

For cDNA production, oligonucleotides were produced to the complementary strand of the hexon gene and the penton base gene, both being MLP transcripts. A further oligo was produced which covered the proposed cap site of the major late transcript, 24 bases downstream of the TATA box. This oligonucleotide was used in conjunction with that used in cDNA production in Taq polymerase chain reaction (PCR). The resulting DNA produced from positive clones was digested with appropriate restriction enzymes to determine the size of the inserted fragment. DNA sequencing of these inserted fragments was performed using a modification of the chain termination technique [Sanger, F., Nicklen, S. and Gulson, A. R. (1977) DNA sequencing with chain terminating inhibitors *PNAS USA* 74:5463–5467] so as to allow T7 DNA polymerase extension (Pharmacia, Sweden).

To confirm the leader sequence cap site, fresh cDNA was prepared and this time a tail of dGTP residues added to it. Briefly, cDNA was incubated with 1 mM dGTP and approximately 15 units of terminal deoxynucleotidyl transferase (Pharmacia) in 2 mM $CaCl_2$ buffer at 37° C. for 60 minutes. The reaction was stopped by heating to 70° C. for 10 minutes. The DNA was then ethanol precipitated and resuspended in a volume suitable for use in polymerase chain reaction (PCR). PCR was performed as previously described using a poly (dC) oligonucleotide with a XbaI site at the 5' end. Resulting fragments were digested with XbaI and SmaI and cloned into pUCI9 vector. DNA preparation and sequencing were performed, as described previously, on clones shown to be positive by hybridization.

FIG. 5 illustrates the DNA sequence of the major late promoter, upstream enhancer sequences and splice leaders 1 and 2 showing the arrangement of splice leader 1 from cDNA studies. SEQ ID NO:1 is the 5' upstream enhancer sequence for the major late promoter (FAVMLP) of Adenovirus CFA20; SEQ ID NO:2 is the FAVMLP TATA box plus sequence leading to the Leader sequence; SEQ ID NO:3 is the first leader sequence of Adenovirus CFA20 (FAVLS1); SEQ ID NO:4 is the second leader sequence of Adenovirus CFA20 (FAVLS2); and SEQ ID NO:5 is the total spliced sequence.

Characterization of Nonessential Regions of FAV Genome

Figure 6:
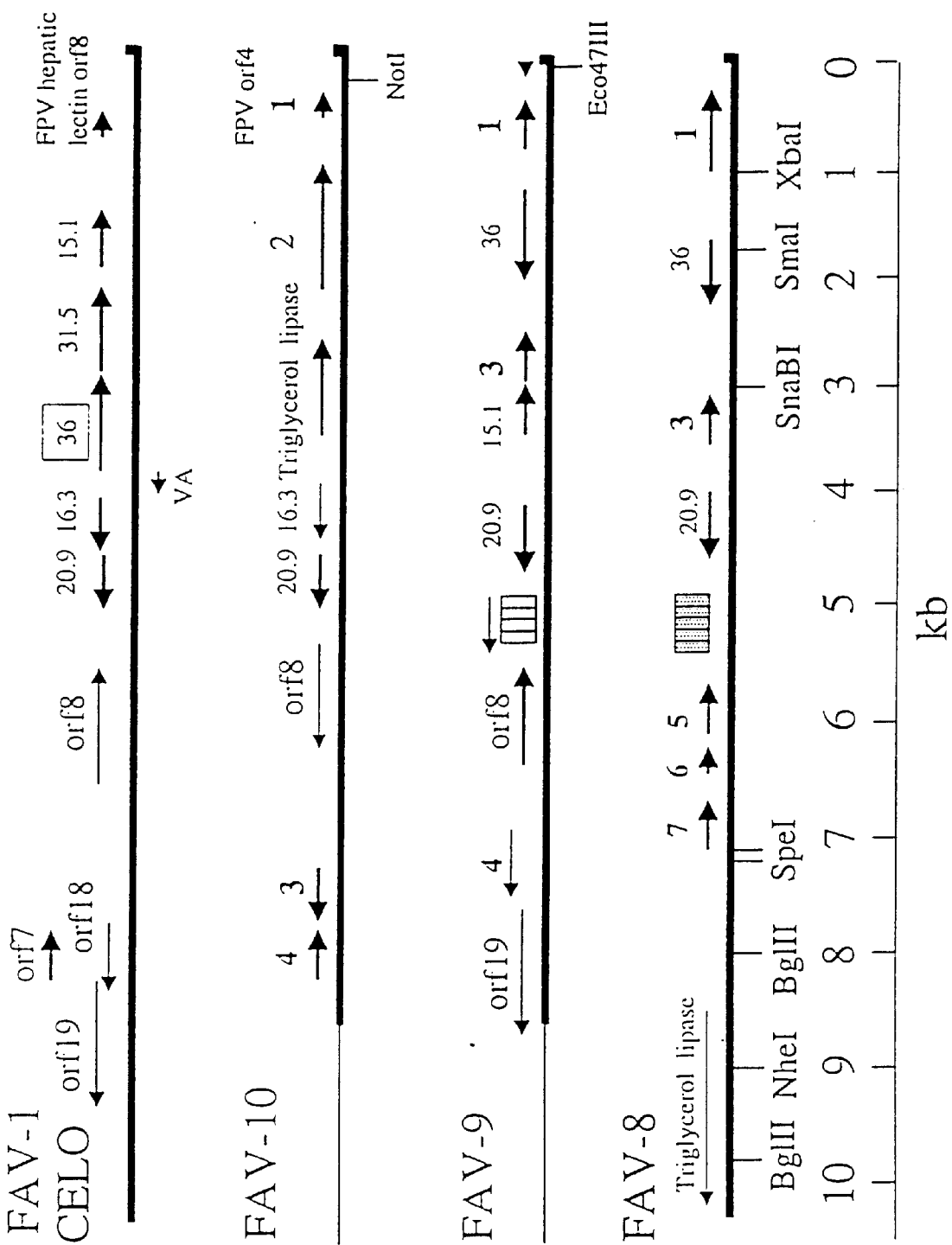
FIG. 6 illustrates the genomic organization of the right hand ends of the FAV serotypes 1, 10, 9 and 8.

FIG. 6 shows the genomic organization of the right hand ends of avian adenoviruses FAV 1, 10, 9 and 8. The regions sequenced are represented by the thick lines. Open reading flames (ORFs) are represented by arrows. Identification of ORFs in serotypes 8, 9 and 10 is based on amino acid identity with putative ORFs in serotype 1 (CELO).

The right hand ends of the FAV serotypes 8, 9 and 10 were cloned and sequenced. SEQ ID NO:6 is the right hand end sequence of FAV serotype 10; SEQ ID NO:7 is the right hand end sequence of FAV serotype 9; SEQ ID NO:8 is the right hand sequence of FAV serotype 8. For serotypes 9 and 10, the region sequenced covered approximately map units 70–100. For serotype 8, the region sequenced covered approximately map units 60–100. Sequencing revealed that there are substantial differences between the serotypes of FAVs.

1. SEROTYPE 10

The right end was identified by cloning and complete sequencing of the FAV serotype 10 (CFA 20) NdeI/3 fragment (4.3 kb), EcoRI/2 (6.2 kb). The total region sequenced was equal to 8.4 kb.

2. SEROTYPE 9

The right hand end was identified by cloning and sequencing of FAV serotype 9 (CFA19) XbaI/5 (3.9 kb), EcoRV/4, 5 and 6 (4.0, 2.3 and 2.0 kb respectively) and BamHI and BalI clones. The total region sequenced was equal to 8.5 kb.

3. SEROTYPE 8

The right hand end was identified by cloning and complete sequencing of FAV serotype 8 (CFA40) NheI/2 (8.5 kb), BglII/5 (1.7 kb) and BglII/3 (7.5 kb). The total region sequenced was equal to the 17.1 kb pairs which corresponds to approximately map units 60–100.

As shown in FIG. 6, the organization of the right hand end of FAV serotype 8 shows some differences from that of serotype 1 (CELO), with some potential ORF's having homology to those in CELO, but arranged on different strands, as well as some unique ORF's to serotype 8. For example, the putative CELO 36 kDa ORF is on the right strand in CELO but on the left (complement) strand of serotypes 8 and 9, and is not present in serotype 10. Serotype 10 open reading frame 2 (ORF2) appears to be unique to that serotype. Another example is the putative 15.1 kDa ORF in CELO which is located 5 prime (upstream) of the 36 kDa ORF, but in serotype 9 is 3 prime (downstream) of the 36 kDa ORF. Another example is the putative 16.3 kDa ORF in CELO which is located on the right strand, but is on the left strand of serotype 10, but not yet located for serotypes 8 and 9. Other features are the existence of repeats in serotypes 8 and 9, which are not found in serotype 10 or CELO.

Construction of FAV Vector

FIG. 7 illustrates a method of construction of a FAV vector. The right hand end NdeI fragment 3 of the FAV CFA20 is cloned and a unique restriction endonuclease (NotI) site is inserted. CK cells were transfected with purified altered NdeI fragment 3 and purified SpeI fragment 1 to produce a functional virus by homologous recombination with a unique restriction endonuclease (NotI) site in the genome. One particularly preferred FAV isolate is that identified as FAV M11 NotI which was deposited at the Australian Government Analytical Laboratories on Mar. 11, 1994 and given the accession number N94/8879.

Construction of Expression Cassettes

The major late promoter and leader sequences were cloned into a plasmid vector with the polyadenylation signal (polyA) of SV40 as well as suitable cloning sites for the insertion of heterologous sequences. The ORF's from a number of antigens and cytokines were cloned into the expression cassette. These included the cytokines chicken gamma interferon (Ch IFNγ), chicken myelomonocytic growth factor (ch MGF) and the antigens S1 from infectious bronchitis virus (IBV), the hemagglutinin-neuraminidase (HN) from Newcastle's disease virus (NDV), glycoprotein B (gB) from Marek's disease virus (MDV) and VP2 from infectious bursal disease virus.

Figure 8:
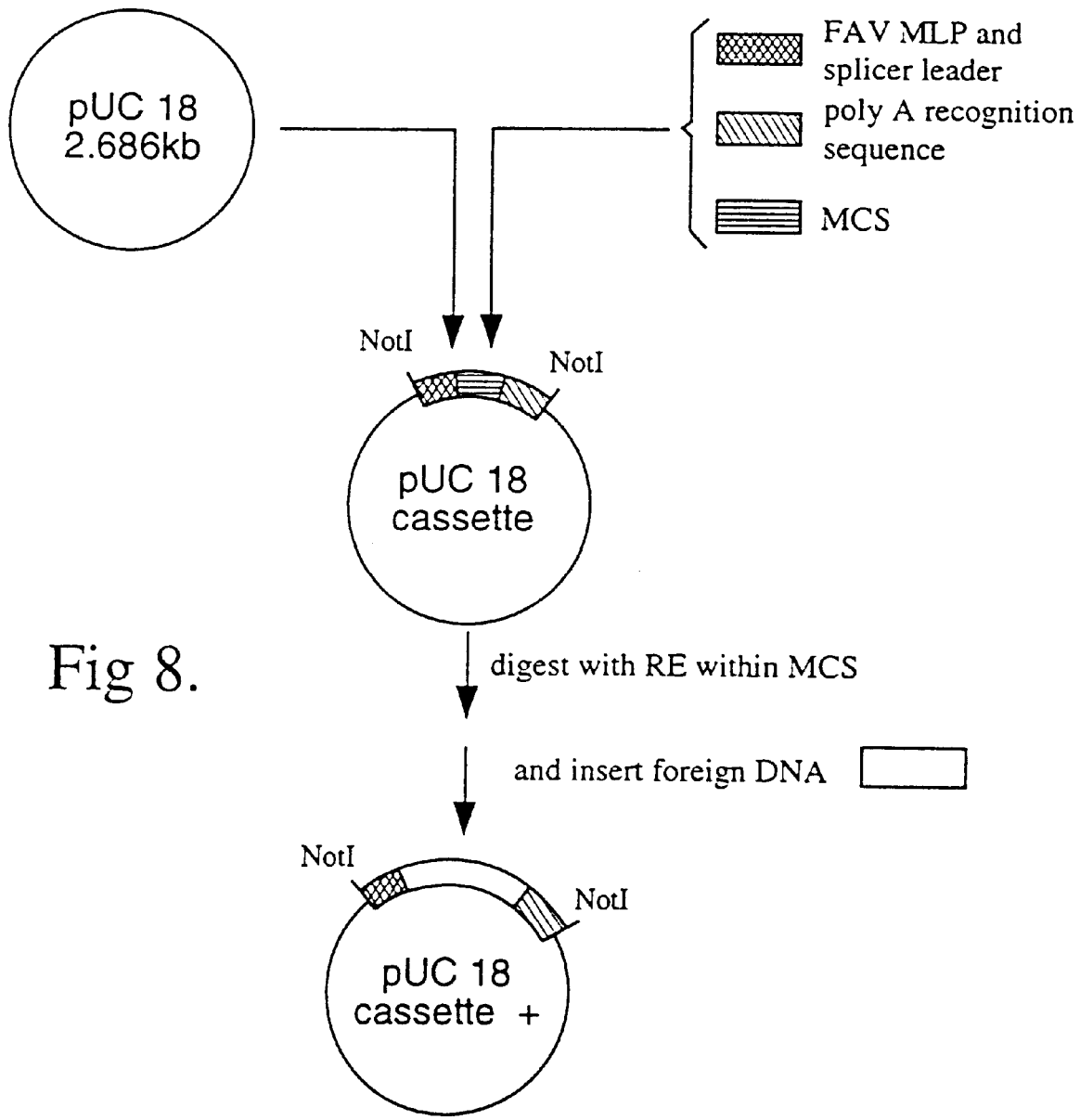
FIG. 8 illustrates the construction of an expression cassette for FAV.

FIG. 8 illustrates construction of an expression cassette for FAV (serotype 10). The major late promoter and splice leader sequences 1 and 2 are inserted into a plasmid vector as well as multiple cloning sites for insertion of foreign DNA and a poly A recognition site. All these are flanked by unique restriction endonuclease recognition sequences (NotI) for insertion into the unique restriction endonuclease site in the FAV genome or blunt ended into any referred site of the FAV genome.

Construction of Recombinant FAV'S

1. Construction of FAV10-VP2 recombinant

The Infectious Bursal Disease Virus (IBDV) VP2 gene was inserted into the expression cassette as described in FIG. 8. The expression cassette was isolated as a NotI fragment and cloned into the unique NotI site previously engineered into the FAV NdeI/3 fragment. The plasmid containing the VP2 gene was linearized and transfected together with FAV SpeI/1 DNA into CK cells. This plasmid was deposited at the Australian Government Analytical Laboratories on Mar. 11, 1995 and can be identified in the bacterium E.coli DH52 pFMLP 234. This bacterium has been given the accession number N94/8878.

2. Construction of FAV(10) thymidine kinase recombinant

The Infectious Laryngotracheitis Virus (ILTV) thymidine kinase (IK) gene (1089 bp) was inserted into an expression cassette, as described in FIG. 8, utilizing the CMVIE promoter and SV40 poly A sequence signal to regulate expression. The TK expression cassette was isolated as a NotI fragment (FIG. 8) and cloned into the unique NotI site previously engineered into the FAV NdeI/3 right hand end fragment of serotype (10) (FIG. 7). Specifically, a 753 base pair deletion was made between the ClaI and SacI restriction sites. The 753 bp deletion removes a potential open reading frame. This ORF has been identified as being unique to serotype 10 with identity at the amino acid level to a hypothetical fowlpox ORF. The plasmid containing the TK expression cassette, flanked by the FAV NdeI/3 fragment, was linearized by digestion with NdeI and transfected, together with FAV genomic DNA, into CK cells. A recombinant FAV 10-TK was selected by passage through methotrexate, a metabolic inhibitor that blocks the replication of TK deficient (wild type) viruses and plaque purified. Southern blot hybridization and probing with ILTV TK confirmed the insertion of the TK gene within the NdeI/3 fragment. The ability to isolate a FAV-TK recombinant by passage through methotrexate, demonstrates that a deletion could be made in the right hand end of the FAV genome and the potential to insert, and express, foreign genes within the right hand end of the FAV genome.

Selection based on expression of TK gene can be used to identify other nonessential sites of the genome.

The method described above can also be used to demonstrate essential regions of the FAV-10 genome. For example, the TK expression cassette was inserted in to the BglII sites of NdeI/3 right hand end fragment of FAV serotype 10. This insertion resulted in the deletion of 2791 base pairs, including two potential ORF's and a transcriptional termination sequence (AATAAA) after the second ORF. When this fragment was used in transfection experiments under MTAGG selection, no recombinant could be rescued, demonstrating that either one or both of these ORFs were essential.

The construction of these recombinants can be used to identify nonessential or essential regions of any FAV genome.

3. Construction of FAV8-Ch IFNγ recombinant

Figure 9:
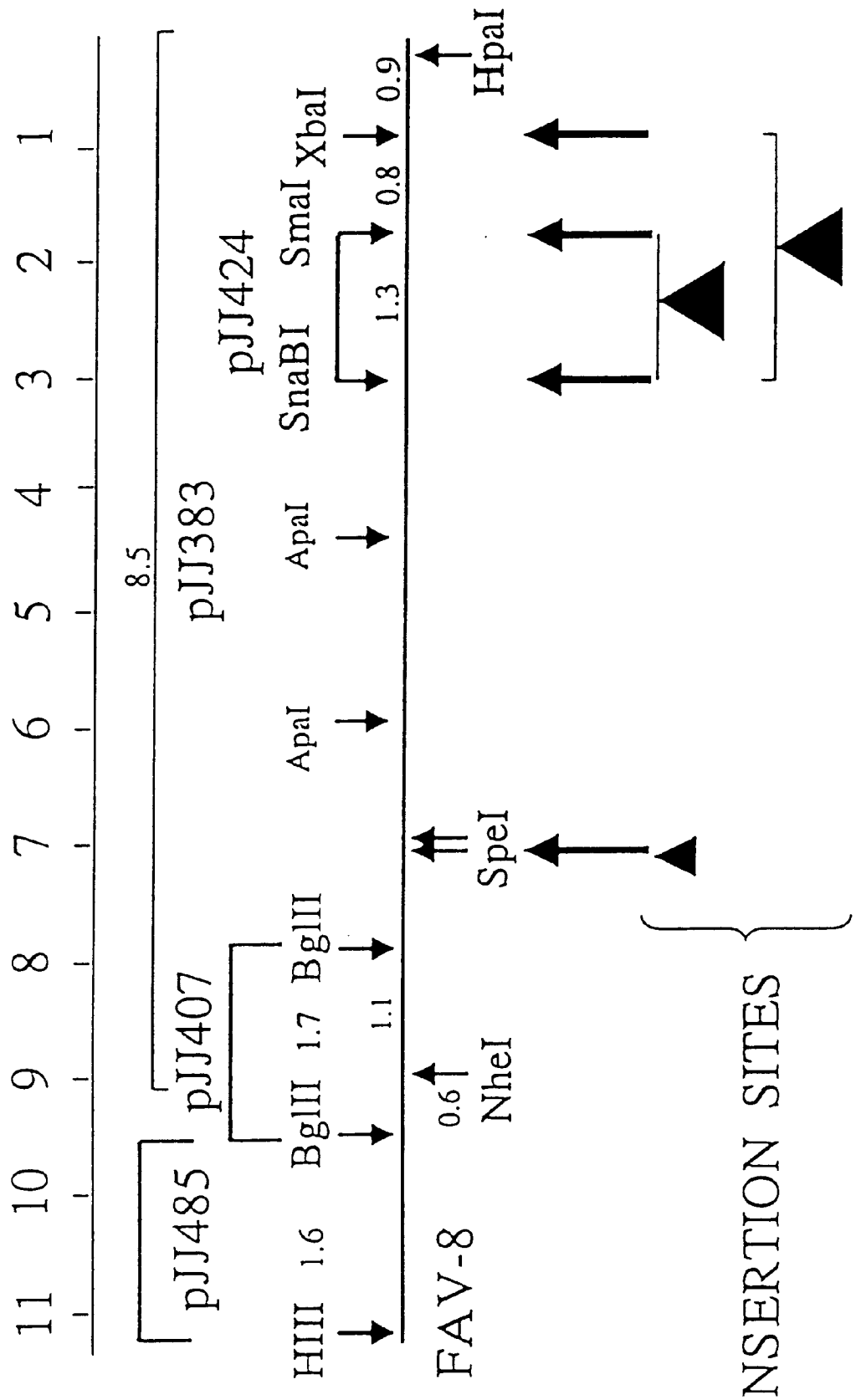
FIG. 9 illustrates the restriction endonuclease map of the right hand end of FAV serotype 8.

Insertions were made into sites between 70–100 map units of FAV serotype 8. An ORF was identified with homology to one in serotype 1 (CELO) (putative 36 kDa). Unique SnaBI and SmaI sites in the NheI/2 fragment (8.5 kb) were chosen for insertion of an expression cassette and the entire 1.3 kb sequence between these sites was deleted. This deletion removed most of the putative 36 kDa ORF and the potential polyadenylation signal (AATAAA) 3' of the stop codon. FIG. 9 shows a detailed restriction map of the right hand end of FAV serotype 8. Unique restriction sites used for the insertion of an expression cassette are indicated by vertical dashed arrows. The 1.3 kb SnaBI-SmaI deletion region is shown by the solid triangle. The scale in kilobases and map units is shown at the top of the diagram. In a further construct a SnaBI-XbaI deletion (2.2 kb) was made which removed the remaining 5' sequence of the putative 36 kDa homologue to 17 bp 5' of a putative terminal ORF-1 which included a putative TATA transcription initiation site. In a further construct a SpeI deletion (50 base pairs) was made.

Figure 10:
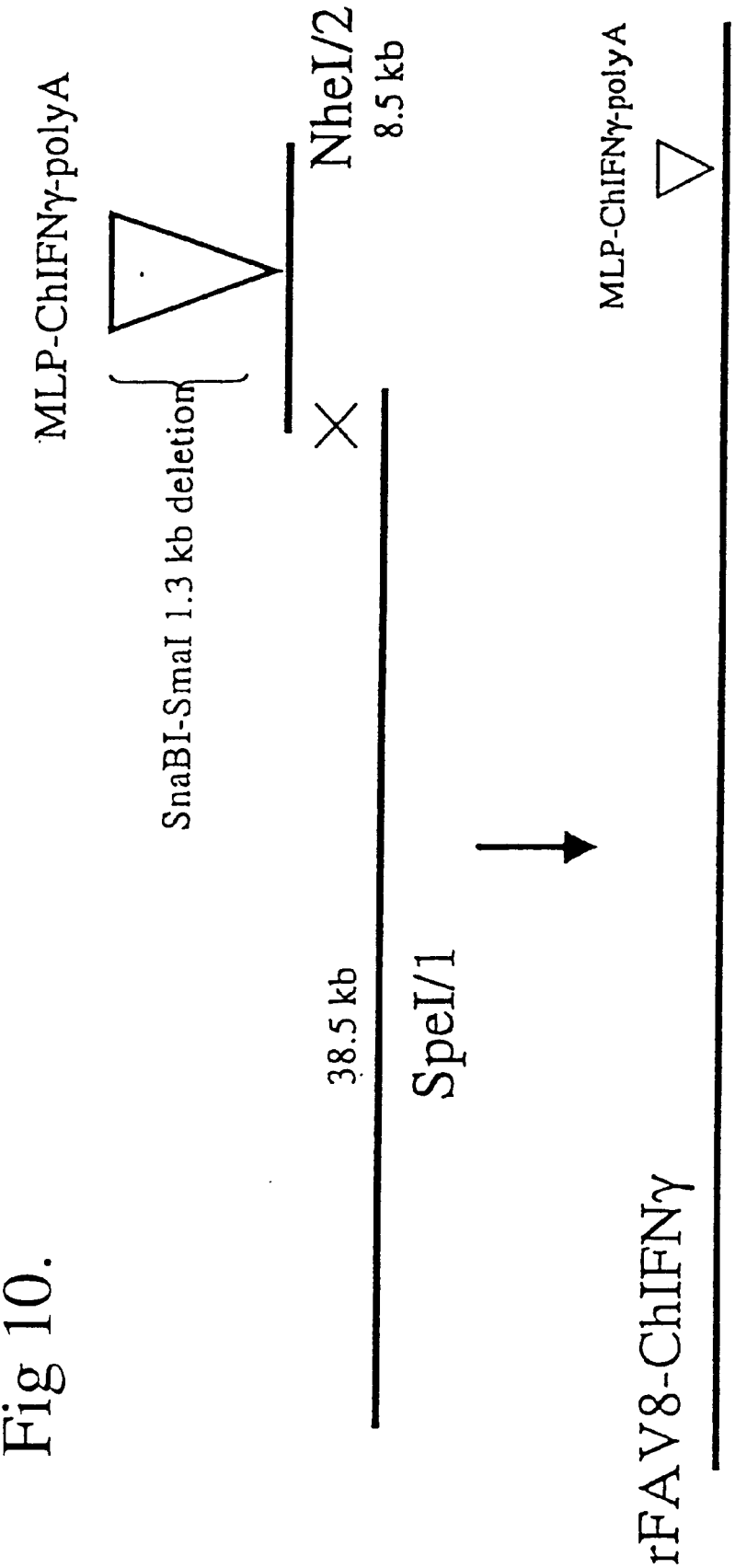
FIG. 10 illustrates a method of construction of FAV(8)-ChIFNγ recombinant.

FIG. 10 illustrates the construction of a recombinant FAV with insertions made into a SnaBI-SmaI 1.3 kb deletion site. The chicken gamma interferon (Ch IFNγ) gene was cloned into the major late promoter splice leaders expression cassette. This cassette was inserted into the SnaBI-SmaI deleted region the SnaBI-XbaI deleted region or the SpeI deleted region of NheI fragment 2. The RHE cassettes containing Ch IFNγ were transfected with SpeI digested viral genomic DNA. The resulting FAV8-ChIFNγ recombinants were plaque purified and characterized by Southern hybridization and PCR.

4. Construction of FAV8-S1 IBV recombinant

The S1 gene from infectious bronchitis virus (IBV) was cloned into the major late promoter splice leaders expression cassette. This cassette was inserted into the SnaBI-SmaI deleted region of NheI fragment 2 of FAV8. The cassette containing IBV S1 gene was transfected with SpeI digested viral genomic DNA. The resulting recombinant virus was plaque purified and characterized by Southern hybridization and PCR. Reverse transcription-PCR analysis verified that the recombinant produced S1 specific message RNA. Recombinants containing the S1 gene in the SpeI deletion site and the SnaBI-Xba deletion site were also constructed.

5. Construction of FAV-HN:NDV recombinant

The HN gene from Newcastle's disease virus (NDV) was cloned into the major late promoter splice leader expression cassette. This cassette was inserted into the SnaBI-XbaI deleted region of NheI fragment 2 of FAV8. The cassette containing the NDV-HN gene was transfected with SpeI digested viral genomic DNA. The resulting recombinant was plaque purified and characterized by PCR. Earlier work demonstrated that expressed HN product could be detected in the tissue culture supernatant of transfected chicken kidney cells when tested against a ND virus antigen by ELISA.

6. Construction of FAV-Ch MGF recombinant

The chicken myelomonocytic growth factor gene was cloned into the major late promoter splice leader expression cassette. This cassette was inserted into the SnaBI-SmaI deleted region of NheI fragment 2 of FAV8. The cassette containing the Ch MGF gene was transfected with SpeI digested viral genomic DNA. The resulting recombinant was plaque purified and characterized by PCR. Reverse transcription PCR verified that the recombinant produced Ch MGF specific message RNA.

Transcriptional Mapping

Message RNA (mRNA) was isolated from infected cell cultures at 6 hours or 20 hours post infection with either wild type serotype 8 or recombinant serotype 8 expressing ChIFNγ. Message RNA was purified using a Qiagen Direct mRNA Maxi kit and either transferred to nylon filters using the Ambion Northern Max-Gly kit or used in RT-PCT reactions using a Promega Reverse Transcription System. Fragments from the right hand end of the FAV genome were labelled with $^{32}$P and probed. The ChIFNγ ORF was used as a probe against recombinant induced mRNAs. Analysis showed that transcripts could be detected from wild type infection for the 36 kDa homologue at approximately 20 hours post-infection. When recombinant induced mRNAs were probed with the 36 kDa gene, of the FAV8 ORF3, no transcripts were detected. A transcript was detected to ChIFNγ. These results show that the FAV-8 36 kDa and FAV-8 ORF3 were both interrupted by the insertion of the ChIFNγ expression cassette and that both these putative ORFs were nonessential. RT-PCR analysis was performed using primers designed to all putative ORF's in the right hand end of FAV 8. The analysis showed that mRNAs were detected at 6 hours post infection and that the 36 kDa ORF of FAV-8 was a late transcript. Using primers specific to ChIFNγ, a transcript was detected from the mRNA made using RT-PCR from recombinant FAV-ChIFNγ infected cells at 20 hrs post infection. The PCR product was cut from the gel, cleaned using a Qiagen gel purification kit, and cloned into the plasmid pGEM-T (Promega). The subsequent clone was sequenced and confirmed as ChIFNγ.

Biological Assay for ChIMNγ

Interferons (IFN) represent a family of cytokines that share the capacity to inhibit viral replication and to exert effects on immune function. IFN-γ is distinguished from IFN-α and β by its binding to different cell surface receptors and its high sensitivity to heat and low pH treatment [Weissmann and Weber (1986)]. Another distinction is the ability of IFN-γ, but not IFN-α or β, to stimulate macrophages to produce reactive nitrogen intermediates such as nitric oxide, nitrate and nitrite [Fast et al. (1993); Huang et al. (1 993)]. The biological activity of recombinant chicken gamma interferon (ChIFNγ) was measured by a nitrite release assay. Production of nitric oxide by HD11 chicken macrophages was quantitated by accumulation of nitrite in the culture medium as described [Lowentbal et al. (1995)]. Two-fold serial dilutions of test supernatants from cultures of CK cells that were infected with wildtype FAV8 or with rFAV-ChIFNγ were made in duplicate wells of 96 well plates. HD 11 cells were added to each well and the plates were incubated at 37° C. After 24 hrs, 50 μl of culture supernatant was added to 100 μl of Griess reagent and absorbance was read at 540 nm. Duplicate cultures were incubated in the presence or absence of 1% (v/v) rabbit anti-ChIFNγ serum [Lowenthal et al. (1997)] which blocks the bioactivity of ChiFNγ but not ChIFN type I. Normal rabbit sera or sera raised against an irrelevant antigen did not inhibit the activity of ChIFNγ. (FIG. 11). The results of this assay demonstrate that the recombinant ChIFNγ is expressed and is biologically active.

Vaccination Strategy

1. Vaccination with FAV-CFA 20

In these experiments day old chicks were used to represent immunoincompetent birds and 3 week old chickens as representative of chickens approaching immunocompetency. Day-old chicks were infected with CFA20 by aerosol spray. Virus was suspended in sterile isotonic saline at a dose of 5×10$^7$/chicken. The birds were placed into a confined area and the virus sprayed into the air at the head height of the birds such that the spray contacted the eyes and beaks of the chickens. The coarse spray was delivered using a pump-action plastic spray bottle. The onset of serum antibody responses were monitored by ELISA and virus neutralization assays. The detailed results are shown in Table 2.

TABLE 2

Serum antibody response and virus clearance in day-old chickens inoculated by aerosol with the FAV CFA20

| Days post-inoculation | Neutralization titer (CFA20)[a] | ELISA titer recovery[b] | Virus recovery[c] |
|---|---|---|---|
| 0 | 0 | 0 | + |
| 7 | 0 | 0 | + |
| 14 | 0 | 0 | + |
| 21 | 0 | 0 | + |
| 28 | 0 | 125 | + |
|  | 0 | 70 | − |
|  | 0 | 240 | − |
| 35 | 0 | 160 | − |
|  | 0 | 300 | − |
|  | 0 | 400 | − |
| 42[d] | 0 | 160 | − |
|  | 0 | 100 | − |
|  | 0 | 200 | − |
| 47 | 0 | 220 | − |
|  | 0 | 110 | − |
|  | 0 | 280 | − |
| 54 | 0 | 100 | − |
|  | 0 | 70 | − |

[a]reciprocal of virus neutralization titer in serum against CFA20
[b]reciprocal of ELISA titer against CFA20
[c]virus recovery from the caecal tonsils of 3 chickens at each time point
[d]re-inoculate with CFA20

Virus was recovered from caecal tonsils for 4 weeks post-infection, the disappearance of virus coinciding with the development of circulating antibody which could be detected by ELISA but not by the virus neutralization assay. No virus neutralizing antibodies were detected over the 7 week period of this experiment. However, attempts to re-infect these chicks with CFA20 at 6 weeks after the primary infection were unsuccessful as reflected by the failure to recover virus and the absence of an anamnestic ELISA antibody response in the serum.

When chicks were infected at 3 weeks of age virus could be recovered for only 1–2 weeks postinfection, and again the clearance of virus coincided with development of antibodies delectable by ELISA (Table 3).

TABLE 3

Serum antibody response and virus clearance in chickens inoculated by aerosol at 3 weeks of age with the FAV CFA20

| Days post-inoculation | Neutralization titer (CFA20)[a] | ELISA titer[b] CFA20 | Virus recovery[c] |
|---|---|---|---|
| 0 | 0 | 0 | − |
| 7 | 0 | 0 | + |
| 14 | 0 | 260 | − |
|  | 0 | 400 | − |
|  | 0 | 440 | − |
| 21 | 0 | 120 | − |
|  | 0 | 220 | − |
|  | 0 | 200 | − |
|  | 0 | 140 | − |
|  | 40 | 240 | − |
| 35 | 40 | 100 | − |
|  | 80 | 280 | − |
|  | 160 | 280 | − |
| 42 | 640 | 560 | − |
|  | 80 | 140 | − |
|  | 160 | 240 | − |

[a]reciprocal of virus neutralization titer in serum against CFA20

TABLE 3-continued

Serum antibody response and virus clearance in chickens inoculated by aerosol at 3 weeks of age with the FAV CFA20

| Days post-inoculation | Neutralization titer (CFA20)[a] | ELISA titer[b] CFA20 | Virus recovery[c] |
| --- | --- | --- | --- |

[b]reciprocal of ELISA titer against CFA20
[c]virus recovery from the caecal tonsils of 3 chickens at each time point Virus neutralizing antibodies could also be detected in the serum of these chickens but not before 4 weeks post-infection (7 weeks of age). This was 2 weeks after the clearance of virus from the caecal tonsils.

2. Vaccination with recombinant FAV-ChIFNγ

Commercial broiler chickens were vaccinated by eye-drop with either recombinant FAV expressing chicken gamma interferon ChIFNγ in the SnaBI-SmaI deletion at either day 1, day 3, day 6 or day 10 post hatch. Birds were housed in positive pressure isolators and maintained on a constant feed regime. Birds were weighed weekly for a period of 7 weeks. All birds vaccinated with the recombinant FAV-ChIFNγ showed increased weight gains which were significantly different from unvaccinated controls (Table 4).

TABLE 4 rFAV ChIFNγ vaccination of commercial broilers; t-test analysis day 34 and day 42 post vaccination

| | Day 34 p value | Day 42 p value |
|---|---|---|
| Unvaccinated vs day 1 vaccinated | <0.001 | >0.05 |
| Unvaccinated vs day 3 vaccinated | <0.002 | <0.05 |
| Unvaccinated vs day 6 vaccinated | <0.001 | <0.05 |
| Day 1 vaccinated vs day 3 vaccinated | >0.2 | >0.2 |
| Day 1 vaccinated vs day 6 vaccinated | >0.2 | >0.2 |

In a further experiment commercial broiler chickens were vaccinated by eye-drop at day 1 post hatch with recombinant FAV expressing gamma interferon (rFAV IFNγ) or a recombinant expressing Ch MGF (rFAV-Ch MGF) or both recombinants simultaneously. Three other groups were vaccinated at day 6 post hatch with rFAV-IFN, rFAV-Ch MGF or both recombinants simultaneously. Other groups were unvaccinated. At day 7 post hatch groups were challenged with 5000 sporulated oocysts of the coccidiosis parasite *Eimeria acervulina*. One group was unchallenged. Weights were monitored daily post challenge. Birds vaccinated with rFAV-IFN or rFAV-Ch MGF had enhanced weight gains and maintained these under coccidiosis challenge.

3. Vaccination with recombinant FAV-S1

Commercial broilers were vaccinated by eye-drop with recombinant FAV S1 at day 6 post hatch (group 1) or unvaccinated (groups 2 and 3). At day 28 post vaccination, birds in groups 1 and 2 were challenged with IBV Vic S strain. Group 3 was unchallenged. At 6 days post challenge the tracheas from vaccinated, control challenged and control birds were scraped and the material used to inject into day 11 embryos. After 2 to 3 days allantoic fluid was collected. Day 11 SPF embryos were inoculated with first passage material (containing viral particles) and after 2 to 3 days allantoic fluid collected. The second passaged virus collected was analysed in an infectious bronchitis antigen ELISA using a monoclonal antibody specific to the N-gene (capsid) of IBV. All unvaccinated and unchallenged birds were negative. Unvaccinated and challenged birds were positive and therefore not protected from challenge with IBV. Birds vaccinated (12/13) with rFAV-S1 were negative, and therefore protected from challenge with IBV.

Sera from birds vaccinated with rFAV-S 1 were tested in an S1 antibody ELISA prior to challenge. No IBV antibody titers were detected. However, at day 6 post-challenge, IBV antibody titers could be detected in 13/15 birds vaccinated with rFAV-S1 and in 4/4 unvaccinated challenged birds. The results demonstrating that rFAV S1 provides protection at the respiratory mucosal surface when administered via the gut.

4. Vaccination with recombinant FAV10-VP2

Chickens were vaccinated with a recombinant fowl adenovirus carrying the gene for VP2 of infectious bursal disease virus (IBDV) or with CFA20. Birds were bled at 0 and 14 days and then weekly after the intraperitoneal administration of the vaccine at one day old. Sera were collected and tested for the presence of antibody against VP2 of IBDV and adenovirus by ELISA. The results in Table 5 show that antibody against VP2 was first detected in the group vaccinated with the recombinant, 14 days after vaccination and peaked at 28 days post-vaccination.

TABLE 5

Serum antibody response (reciprocal titer) in chickens given an FAV-VP2 recombinant or CFA20.

| | | Time post-vaccination (days) | | | | | |
|---|---|---|---|---|---|---|---|
| Vaccine | Antibody | 0 | 14 | 21 | 28 | 35 | 42 |
| FAV-VP2 | VP2 | <100 | >400 | 400 | 1600 | 400 | ND |
| FAV-VP2 | FAV | <100 | 100 | 100 | 400 | 400 | 200 |
| CFA20 | VP2 | <100 | <100 | <100 | <100 | <100 | <100 |
| CFA20 | FAV | <100 | 100 | 100 | 200 | 800 | 800 |

ND = not done

The birds vaccinated with CFA20 did not have detectable antibody against VP2. Anti-adenovirus antibody was detected at 14 days post vaccination in both groups.

In a further experiment, chickens were vaccinated intravenously either with the recombinant adenovirus carrying the IBDV VP2 gene or with the CFA20. Both groups were challenged with virulent infectious bursal disease virus 21 days after vaccination. All birds were killed 4 days later and IBDV in the bursa of Fabricius determined by ELISA. The results in Table 6 show that birds which received the recombinant vaccine were all protected against the infection with viral antigen titers in the bursa of less than 1/4. In contrast all the birds immunized with the parental adenovirus had antigen titers of greater than 1/128.

TABLE 6

Protection against IBDV induced by the administration of rFAV-VP2 or CFA20.

| Vaccine | Infected (10) | Titer |
|---|---|---|
| rFAV-VP2 | 0 | <1/4 |
| CFA20 | 10 | >1/128 |

5. Administration of Consecutive Vaccines

Two combinations were employed for investigating the feasibility of consecutive vaccine by aerosol. In the trial the initial vaccination was with CFA19 (serotype 9) and this was followed later with CFA20. The results are shown in Table 7.

Vaccination with CFAI9 did not protect against infection with CFA20, (Table 7). Challenge with CFA20 4 weeks after vaccination with CFA19 resulted in the production of CFA20 specific virus neutralizing antibodies and CFA20 virus could be recovered for at least 7 days after challenge. No cross-neutralization between CFA19 and CFA20 was found by the in vitro neutralization assays.

TABLE 7

Consecutive vaccination: Serum antibody response of 3 week old chicks infected by aerosol with the FAV CFA19, and re-inoculated with FAV CFA20.

| Days post-inoculation | Neutralization titer[a] CFA19 | CFA20 | Virus[b] re-isolation |
|---|---|---|---|
| 0[c] | 0 | 0 | − |
| 3 | 0 | 0 | − |
| 7 | 20 | 0 | + |
|   | 20 | 0 | + |
|   | 20 | 0 | + |
| 14 | 640 | 0 | − |
|   | >1280 | 0 | − |
|   | >1280 | 0 | − |
| 28[d] | >1280 | 0 | − |
|   | >1280 | 0 | − |
|   | >1280 | 0 | − |
| 31 | 2400 | 80 | + |
|   | 2400 | 40 | + |
|   | 2400 | 80 | + |
| 35 | 2400 | 160 | + |
|   | 1200 | 60 | + |
| 42 | >2400 | 320 | − |
|   | >2400 | 320 | − |

[a]reciprocal virus neutralization titer against either CFA20 or CFA19
[b]virus re-isolation from caecal tonsils
[c]inoculate by aerosol with CFA19
[d]inoculate by aerosol with CFA20

The identity of viruses recovered from these chickens was confirmed by restriction endonuclease analysis of their DNA. This demonstrated that only CFA20 was recovered after challenge of CFA19 vaccinated chickens.

6. Administration of Simultaneous Vaccines

Simultaneous vaccination of chickens with CFA20 and CFA19 by aerosol was also investigated. The results given in Table 8 show that neither the timing or magnitude of the antibody responses to either of these viruses was compromised by the presence of a second FAV infection.

TABLE 8

Simultaneous vaccinations: Serum antibody response of 3 week old chickens inoculated simultaneously by aerosol with the two FAV CFA10 and CFA19.

| Days post-inoculation | Neutralization titer[a] CFA19 | CFA20 | Virus[b] re-isolation |
|---|---|---|---|
| 0[c] | 0 | 0 | − |
| 3 | 0 | 0 | + |
| 7 | 0 | 0 | + |
|   | 0 | 0 | + |
|   | 0 | 0 | + |
| 14 | 1280 | 0 | − |
|   | 1280 | 0 | − |
|   | 1280 | 0 | − |
| 28 | 2400 | 20 | − |
|   | 1280 | 40 | − |
|   | 2400 | 20 | − |
| 35 | 4800 | 1280 | − |
|   | 4800 | 320 | − |
|   | 9600 | 320 | − |
| 42 | >20000 | 1280 | − |
|   | >20000 | 320 | − |

[a]reciprocal of virus neutralization titer against either CFA19 or CFA20
[b]virus re-isolated from caecal tonsils
[c]chickens inoculated with CFA19 and CFA20

The virus neutralizing antibody response to CFA19 was first detected at 14 days post-infection and that to CFA20 at 28 days as found when these viruses were administered alone (Table 3). Restriction enzyme analysis of the recovered viruses showed that at 3 days post-infection only CFA20 could be isolated from the caecal tonsils, however by 7 days both viruses were recovered.

Although the foregoing specification refers specifically to fowl adenovirus vectors of certain serotype (4, 8, 9 and 10), it will be understood that live infectious avian adenovirus of any type may be employed in this invention. Similarly for the purposes of construction of a FAV vector eukaryotic promoter and leader sequences may be substituted, as well as mutants and variants of the specific sequences mentioned herein. It will be understood that immunization against a variety of diseases, and of a variety of different bird species is encompassed within the scope of this invention despite the fact that the invention has been exemplified only with respect to fowl and a heterologous sequence derived from infectious bursal disease virus. Other birds in which the vector is effective include, but are not limited to, turkeys, ducks, pheasants, quail and geese.

All of the references referred to herein are incorporated to the extent that they are not inconsistent with the present disclosure.

TABLE 9

Nucleotide Sequence of the right hand end of fowl adenovirus serotype 10 (CFA20) genome

```
GAATTCTCCGCGGTCGTACCATCTCAGAACAGCCAATTCATCGCTCAAATCGTCTGTCTTCCTGGGAGGACCCTCCTCTC

EcoRI

TCCACTCCGCTACCGAGCAGGGTTCGGAGCCGTTAAAGGCACACTTCCAACGGGAACCATCTTCAAAAGTTGATCCGGGA

GGAAGACCGCACAAGGCGATCAAAACAAACTAAAAAACACGCACGATAAGGTCACATGCAATCGACCCTAACCTATTCTC

CCAAAATGATACTCACCACAATCACGCAATGCATAGAGTACGGCTCAGAGGCTCCTTCTCGAGTGGAGTACTAGCCGGGC

GAATAAACTCCGATCCGAACATCCGCCATATAAACACAGCTTTCGTAAAATATTAACAGACACTAACTTCCTCATTGACC

CGCTTAATTGCCGTGTCAGCAGGTGGCTGACAATGAGTCATCGATGAGTCATCGCTAAGTCAACAATGGAACTTTCCACT
```

TABLE 9-continued

Nucleotide Sequence of the right hand end of fowl adenovirus serotype 10 (CFA20) genome

```
TGCTAACAAAGCGAAACCAAAAGTTAATCATTAACGCCACACCCATGATGAGTCATCGCCAGTAAACCTTAAAAGGACGG
CTCCAGCCCGCAGCGAAAAGCAACCTTACTTCCAACACGAGGGCTCTGCGGAACCATGGCCGAAGAGTGGCTCGACTTTT
CACCCCTCCACTTCGCCGAATCCAGAAGGAGAAGGTGAGGACATGTCCCTCGAGACCGAGTGCCATGCCCCTCTTCACTA
TATTTACCATGCTGTCTTTTGATGACCTCCTGGCGGCTGCCGGTCCCCCCGGAATACTCTCCGGAAGAGAACCTGTAAAC
TCCGTCGCTCGACACCATACAGGTAGGAGACATCATGGCCCAACTCGCGTATTCCGATAGAGGGACCTCCGACCAACCCT
TCCGACTCTTCCTCCAGTTGGGATTCAGTACTTTTCTGCGCTGTCAACTCGTATGACTTAAACTATACCATTGTCTTTTC
CAGACTCCGAGAGTCTTGGCAATCGCACGGCGCATACTTGAAAACCGTACCTTCGCTCGAGTGCGTGCAAAACGACGGGA
AATTCCAGGAAGCATACTGCTCACTGGTGAGAATGCACGCCGTTTCCGAAGATGCCACTGAGCATCTCAATGAACTCTTA
CTAGACGAAACCCACTACCAACATTGCGAACCCCTCAATGACATGTTGGACTTGGGATTCCGGTGGCTCAATGACCTAAA
AGGAGGAATGGAGTGGTGCATGGACACTGCCCTGGATCGCGCATCAAAAGTCATGCCTCTGACTGACTATCAACCACAAT
AAATAAATTTTACATTAAAAACTTTCTGAGTAAGATTTTTCGAACCTGAAAAATTCTAAGTGCGGTTAATCATTAATCAA
GTTAAATATTAAACTCTAGTTAATTATTAAACTCTAGTTAAATATTAAACGCTAGTTAAATATTAAGCTGAAGTTAATGA
TTCATCCGAGTTAATGGATAACCTTGAGTCAATGATTAACTCTGGTTAATATGTAACTCGGCTAATGATTAACATGGGTT
AACCATTAACATGGTTTAACCATTAACTATAGTTAATAAATAACTCTAAGTTAATAAGTAGCTAGTGACCGTACGATTGA
CGTCACGGTGACCGTCGGTGTTGCCATGGAGATGTAACCATGGTGATGTTAAACATTAAACTGCTGACACCAGTGGAATT
TTCCATGTTAACCATTAACATGGACCTTGTCCTGTTTGTTTATTCACCATGGCAACATACCATATATGGACATCCGACTC
CGCCTCCCCCGTTATACATTAACGATGGCGTGATAGGCGGAGCTCTCTCCCATTGGCTCTCAATGATGTCATGTAGTTAC
ACATTAGCCCGTTCAACCTATATAGGTAGACCAGGTAGGCAGGTTCAGACAGACAGACCGGGACCAGCAGACTGAACGG
AGCTCTCCACTAAACCGGTAGGCCTCTATATTGAATCGATGAATAAATACCGAATCACTCAATATTATGATTTTCCATTG
AAATTAATGGTGATTTTCTTCAATCAAACTCCCACCCCCCTTGGCACCCCCCTGTACACCCCCTGTACAGGCGACCACC
CCCTATGATCACCCCCCTGTACAGCCGACCACCCCCCATGACCACCCCCTGTACCATTACAGCCAATGGGATCCCATCC
ATTGACATCACATGATCCCCGCTGGCCCTATGAGGTGGCTACCATATCCTTCACCCTATTGGATCCCATGCCGAGGGCG
GAAAAGATGGGAGGCGCCCGTACCTCGACAACCAATTGGCTGAGGCCCTTCAGTTCAGTTCCGCCCTCACTTCCGACCAA
TTCAATGCATTGGAGTTCACCACGTGGGTTGTNAAGGGGCGGAGACTCCTCCATAAGGGAAAGCAGTACCGCCTTTACAA
CAGGGCGGCCGGGATATGCAGTATCCACCAATGGAGAGAAGTGAGGCCCAGCTGACCATGGAGGCCGTAGCCAATGGGCT
GTGGGATCTGCCGGATGAAATACTCGGGAGCCCCCTACTGCACAATACTGGTATACACACCTGGGGCTGGGGGGTCCCCG
TCACTACCGAGATCAGCCTGAGGATGGTGGTAAAGACCCTCCGTGTCAATACTCCATTCCACCGCCAGGGGAGATGCCT
ATACCGGTATCCAAGGAGGTCCATGTAGAAGCCCCCCAACATTTTGAAGACATGCTCCAGGGGGTCCTGACGACCACCGA
TCTAAAAAAGCATATTCCTAGACCCATCTTTTCCCGATTTTTTAACGAAAAACCCTCGGTTTGGGCCTATAAGACTTTCA
AATATTCGGCCGGTGAAGAAAAATGGCGAGTGGTGGTCCCTACCGAGGGTCCCTATGGGGGTCCTAAGAACCCTGTTTCT
TTGCAAAACCTCGCGAAAAGGGTGTGTTGAAAATTGTCTAAAAATGAAAAGGGCGGGGCTACGGTTCATGCCATATTAAT
AAACCAATCAGAAAACAGAAATACGACTCCTCCTCTTTGTGGGCGGTCCTGGGGAACACCAATAGAAATAGAGACTCCGC
CTATGAGGCGGAGACTTAGTTACTGAATAACTTTTCGGACTTAGAAAAATTTTCACCTGCTTAATCATTTACCAATGGGC
CTACGTCACTATGCTCCGCCTTTAACTCCGCCTATAGCTCCACCTCTCTCTCCGCCCCGATGGACTTTGGACTTTAGATC
ACATGACTGCTACGTCACGGAGGGAGGAGCTTCGGACTTAGAAATTTTTCGCTCTATCAATCATTAACTTGACGATGGAC
TTTGAACCCCACGTAAGCGACGGGAGGAGCTAACGTTAATCTTCAACTCGGACTTTGCCCGGAAGCGGAGCTTCGGACT
TAAACTTTAACTCGAACTTTGTCCGGAGGCGGAGCTCCGGACTTAAAAAATTTTTCACCGCTATAATCATTATCCAACT
GAATCACATGACACAAAGGAAGAGACTGTAATCAAATTTAATTATTAACAACTCAGTCAACATTTACATCATCAGCGGTA
```

TABLE 9-continued

Nucleotide Sequence of the right hand end of fowl adenovirus serotype 10 (CFA20) genome

CAAAGTCCAGTACATACACGCCACGCCCCAAGACATTGAAATGCTTCCTCCGTCACGCCCCAGCGCCCCATGCGGTACTG

CTCGGGACACCACTGATTATCATAGAGCTTCAACCACACCTGGCACGAAGAGCCGGTATCTCTATAAAAAACCAAATGCA

GGGCCGTCGCATATCACTCCGACACTTCTCCAACTTTCCCTTAGTCTGATCGGAACAATGGATACAAATTAACAAAGTTG

CATGACATTCGCACACGGAAAACTCTTGCAACCCGAACATGTACTTCAGAGGACTGCATTCGGGACTGTACTTCTCAACA

AGTTTAGTC<u>CATATG</u>AACTTCAATCCGCGATGAACATATCTGAAAACCTCAGGCCTCTGACACCATTCCGGAACTGCCGC
        NdeI

TCCGAACACAAGGTACATTGTCATCTGAAATTTAAGCCATTTATTCATACACGCACTCGTAAATACATCCCTCTCTACTG

CCAACCGCTTCTGATGTTATGCAATATTCACCCAAGCGGTACTCTTGCGCGTATCCCTCGTTACGCAAAAGGCATACACC

CTTAATCCACTTCTCACTGT<u>CATATG</u>GATATTTCCCAAAAAACAAACACTTAACAGCCAAACCAACCCCCTCCAGATACG
            NdeI

CGCTTCCAAAATCCGAACCAAGGCAAAAACAATCGATACAAAATCCTCCATCTTGCAAAGCATAGAGATAAAAGAAACC

CGTTACTAGTCCAGGAAACACTTTTCCTAAATCCAATTTCTCCCAAGCATTAATTATATCACACGCGCGAAAATCGTGAA

ACATAGCCAGGTTCAATTCCCATAAGGGCGCCAACATAAGTAACCCAACATTAAGTAACCCAACATTACCCACCGCACAC

TGGGCTGTCAAATGAGCGCTCTGCAGTCCTCCAAACTCTGTAGTACTTATACAGTCTACCTCTTTAATCATTAACCATAG

ACGTCATGGAAAATTTCCAACCCCACCCAGAATGAATCACCGGTCAAAGGTCACTTCCTCATTACCTAGATAAGGATCAC

AAAGTACTTCCTCATTACCTAGATAAGGTATCACAAGGTACATGAGTCACCCATAATGATACTGAATCAGCGGTTTCGGT

CACGTCAGTATCAGACAATCATTAACCAGAGATTCCTATAAACTTTCCGCAGACTCGCACCACGGTATTCCATCCGAAGA

CTGATCCAGTCTGAAGACAATCTTCTCTTCGGTGAACAGTCCTGAGGAAAAACACCATGCGGGTAAGCATCATTCATCCA

TTATACCCCTTTTTACTCTTTCACCTAACCTCGCTAACA<u>TAGATC</u>CCTACCTCTCGGTCCACAGCTGTTAACTCCATAC
                                      BglII

AGAACAAACCCACGGTCCCTACCAAAGGACCCATGGCCAACTTCACCTCTGTTCGCCATGAAGGTCACATCAATTACTTT

TGGTATGGGCAACACGGAATGGCACCCTCGAAAATCCACGGTCCTCTCCATGATGATGACATGATATACTGGAGACTCCG

TGACCGTGGGTTCCTGAGAGGAGGCAGAGAAAAGAACCTGATCCTACTCGTCCATGGATGGCACGGCCTCCACCGCACCT

TTGATATCTTCTTCAGCTTCCTCCGCTTCCACCAGAAGATGACACCAGACGTAGGTGTGCTCTTAGTAGATTGGGGGTA

CAAGGTGCTGACAAACTAATTCTAGGAGATGCTGCCTACCACGCCGTCACCATCAATATTGATGGCCTACTCAAGAACCT

GAACCGCACCAACTTACACTGCATAGGACACTCCTTGGGGGCTCATGCATGCGGTGCTATTTGTCGAAGATTCAACCAGC

TCCAAAAGAAGAAATGCACTAGAATTGTTGGACTCGACCCAGCAGGGCCTCTCTTCAAAACCAACTCTCCCTATCCTTAC

CTCACCAAAGCCCGTCTGTCTAAAGAAGATGCTGACTATGTAGCTCTCTTTATGACGAACCGACGGATGATGGGACTCCA

CGAATTGGAAGGAGATGAGTACATTACCCCCTATATAGACGGAACCTATCTGAACCATTGTCCTTTCGTCGGTAAATGGA

CAGGCACCATCACGGCAGAAAACTACCAAGGAAGAAAGGTCACTGAATACATCGATTTAGGAACGGTGGCCAAATCGGGA

ATAATCCCACACACCATGGAATGCATGCTCACACCTCATGGCCCCTGTTCTTTTCATGGTGTCCCTAGACACCCGCCAAG

GCCTACCTGCATTCCGGTATGTTGACAACCCTCCCAAAGATGAAGGTGCCATGCATACGGTTTGGAATGGGTATACCATA

GGGAAAGACTACCTATGACCAGCCTATTTCAAACACGAAACTATCTGGCTTAGTACGCTCACGACAGATGGAAACCAGCT

AGCTAGCACCCTTC<u>GAATTC</u>CAACACGAAGATTCCATAGATCCGTCTTTCATGGCAATGGCAATTAGCGACAAAGGTTGC
              EcoRI

ATCTGGTCCGGCTCCCATCTGAGCTACCACTACAGTATCATCCCTTACGGAAACAAATACGATCTGGTAACATCCTTCAG

TGCACTCTCCCCTGGAATGGTAGACGCACACTTCCTCGAAGTCTACATGAACTACGAACACTGCCCCGTCTATCTAGCCC

GATTTCTGATTCCCAAACCGTACCAACTGAAGTTACCTAGACCCACCACAGCCGGTCTCTCTTCCGAAATCTTAAGATGC

AATAAACAAACCACATATACCTGGAACTGCTACAGAACATGGCAGCAAGCTGTCCTACCCGTGTACCGCCAGCAACTCGA

TCTTACGGGTGACGGAAAATACAACATCCAGGTCCCTCCCAAACATGGATGCCTGAAAGAACAATCCAACTTTACCGATA

TABLE 9-continued

Nucleotide Sequence of the right hand end of fowl adenovirus serotype 10 (CFA20) genome

TGTTCCGTACATACATGGGTGAATATGAAGTCTTGTCTGAGCAGACTGTCATAGTAACCAGCTTGCCGTCACCGTTCGAA

CTCATCCGTATTGCTCTGAGAGATCCTGCCTCACCCGCCATTCAAAACATCATGACCTATTGGGACATGTGCGTACCCGT

AGCTAGCACTTGTAGCTTCAAAGTAAATCGAGCAACGAGAACTCTCAGCATAACCTGCCCCGAACCGAATACCTACTGGA

TCTCCTTCTTTTACCAATGGGAAGAAGTCTTGCTCAAGATTAATGTCCATCCTAAACCCACTACCACTACCACCACTACC

ACTACAACCACTACTCCCACTACCACTACAACCACTACTCCCACTACCACTACAACCACTACAACCACTACTCCCACTAC

CACTACAACCACTACTCCCACTACCACTACAACCACTACAACCACTACTCCCACTACCACTACAACCACTACTCCCACTA

CGACCTCCACCGAATCAATCACAGAACCGAGCTCCGCTTGTGATGAAGAAGAAGATGAAGATTGTTGGTTCGAAAATATC

GCGATCAGAATGAAGTTCCTCAAAAAGGTACAACTCCCGTTCAAAGTAGCGAACAATGAAATGTCAGAACCAACTACTGC

TGCTACTACTCCTTCCAGCCCTGCCGCCATAGAGGAAGAAAGCAACAGCAGAGCATCTACACCACCCCCTCTTCAACTCA

CCGTATCCCCAGGTACTAACCCCCCTCTTCAAGAATTCCTCAAAGCGGAACCATCATCTAAAGATTCCCTCCACAAGGAC

CAAGACGCCACGGTCACCATTCCTGCCACCATTGGACTCTTAGCCCTAGTCTGTCTCAGTGTCATCGTTGCCGTATTCAT

TGCCCTTAGAAGGAGAGGGAGAGGTCAAGGCCAACCTTATTGTTGTTCCTGGAAGAGCAATAATACTGTATACCAGGAAA

CTACTGAAATGTTGTAAAATTTATAACGCTATAAAAGTGTCTGACTACAATAAAGATAAGAGCATAATCAACTCGGGTGT

CCGCCCATTCCTTTCTCTATATATTCTGTCACGAACAGATTTCAGACAGAAGGCGACATGGGAGGCGAGAA<u>GAGCTC</u>CGT
                                                                                                                                                              SacI

AAAGCTAGACAGGTTCCCCTACTGGGTACCCTAGAAGAAATAGATAGGTATGCTAAGCTAATCGCGGAACAGTGGCCCCA

TCGGGTCCGGCAAACACTTTCTAGTTATAGG<u>AGATCT</u>GGAAGGTACCTTACATGCGGGGCAACATTTAAAGGAATACTGC
                                BglII

GAAGTGCTATATCTACCTTCCCCAAAAAGAATGACCGTCATTGGCATAGTGGACAACGTCATCTCATTCGCGGATGGATT

GCAAGTAGTCATTTTGGTGGCGGAAGATAAAACCGTCTATGGCTACGAAGAAGACACTCTCCATAAATTAGCATCCACCA

TACCAGAATTCTTTCGTATCGGAATGCAGAACTTTGGAACCGAAGTATTTCACTGCGGTTCCCACATCCCCCCATTGGTA

AGTGCAGATCCCACACCCTCTCATTACTTACCTGATAGATACTAACACACTATATTCCAGTCCGAGGAGGAGCGTCAGCG

TGATCCCGAGATAAGGCGGCTCCGAGAAGAAGCTCGAAACTTCATATCAGCCGGCGAAAGAAAAACAGACTAACCAACCG

CAATCCGATCCGAACATAGCCACGCAATGGTGTGC<u>GGATCC</u>ACTTAAAATAGATTACGCGTATTCCCAGAAATAAACTGA
                                        BamHI

TTGAAATGAGAGGCAAGAGCTGTGTCATTATTTCGCGTTCGTTCGCAAATACGGAAGTCCATCACGGATATCCGTAATCG

TCATTTGGGTGGAGACCATGAGTC<u>ATCGAT</u>GACTCACTTAAACGGTTTCGGTTTCGGCTATCACGACGTGCGCGCGGCGG
                         ClaI

TTGTAAGTGTGTCAAAAGACGCGGTTATATAAGATGATG-

TABLE 10

Nucleotide Sequence of the right hand end of fowl adenovirus serotype 9 (CFA19) genome <u>GGATCC</u>ACAGAGAACCTTCCGCCAACTCGGTATACGCTATCTCGGTGGTTACATCGTATTTCCCATATCTTAAAGTCTGC
BamHI

ACACTATAGCCTCCCATATATACGCTGCTATCATGTGAAGCAACTACTATAATCATAATAGAAGAAACAAAGTCCTTCTT

AAAATTTGGGGAATACGACATTTCCGTCATATACTTTATGCTGTAATGGTTGAAGTAACTGTCATATCTATAATCACGAC

TAAGTGTATACCCATTCCAAGTACTCCTTACCGGTCCTACCCTCGACCCTTCCTGTAATACATGGAACACAGGCAAACCT

GTCTTTACATCCAGGGTTTTCAAAAACTTTGGAACAATCATTCGATGATAGCATCCACTTAAACTAAACGTATTACCCCA

GGAAAATTCCTCACATACTGTCGCTCCCCAAACATTTTCTCCGCATACTCTTCCGGACCATCCACCGTGTATACCACAGC

TTCTACCGCCCTTATCTTCCACCATTAAATCTTCCGAAGCCGTGTACCCACCAGTGATCCACGAATACTGAGTCTTTAGA

TABLE 10-continued

Nucleotide Sequence of the right hand end of fowl adenovirus serotype 9 (CFA19) genome

```
ACGACCACATAATCCGCATCCAACTTATCTAATCCACCGCTTACAAATGTCGGTTCTAGCCCGACTATTCTGATACACCG
ATGGCCCTTGCTCATTTGTGAATACTGTCTACATATCGTCGAGCAAGCATGAGCTCCTGCCGAGTGACCTATACAGTGCA
ATTTTTTAGCGTCGGGGATATCTACCAGAAACTTCCTAAAATCCGCATGTAAACCATCCGTATCATAGTACAACCGATAG
TCCACCAACACAACACCTACGGCGGGAGTCATCTTCTGATGAAATCGCAACACCTTCCTAAAATCGTCATATCCCAGATA
CCATCCTGGTATAAGCAGCACTATGTCTGATTTCCCGGCGAAGGCATTGTGCATTTTATGGTATACACCATACTCGTATC
TCGCATCGTGGAACTTCGGTACACCACCATGCGATCCATACCACGTGATTCTCGAAGGAAGTCTGTTCGGATTTCCGGCG
CTTTTCGGAGCTTCCAGTTTAGTAGCCGGAGGCATTGCCACACAGGACCGATTGACCAAATCATGGCAACCTTCTGATTT
CGTACCCGAAAATGCGGAGGCCCCGAGGAGCACCCCGAATAACTGAAACAGAACGCAAAATTTAGACCGGTACCCTCCCA
TACGATTATCACGTCCCAAAGCCAAATATCACGGTACTCACCAGCGCAAAAATCTTCATGAAGATCTGGGGCAAGAGCCG
CACAACAGTCCACCTGAATCTGAGACAGCTTACCGGCGACTGTACCAAACCGGTGTGCCACCGCCGAATTTATTCTCTCA
ATCTATTAATGTTTAACTAAACAAACTTGCTGACACTTGATAAATATTTACTGACCTAGACAATTCCGAGAACTTCCTTA
TTACCGTGACTATGCAGTATCAAGATAAACCCTTCCAAAGTTCGACTGAGTACACGGTGTACTTCCTGTCATAAAATATC
ACTTCTAAATATAGTCCTAGGTAGAAACTATAAATGGTAAGAGACAACACACTGATTCTTAGAAAAACCTCACAGAACAA
GATGAACCTCACATTATCCTGACTCTTCCTTACGAACTGAAATAACCGGTAAGTCATAAAAATGATTTTCCTTTTGACAT
TGCGTACGCGGAAGCAAACTAGAAAAATCGAACTTGGAATTTTCCAAGTCGAGTTAACTATTAACTTGATGACGTCAATT
GGATTAATCATTAACTCGAATTAGTTAATGATTAACTAGATCTGGTTAATGATTAACTAGTCTCAGTTAATGATTAACTA
ACCTGGTTAATGATTAACTAACCTGGTTAATGATTAACTAATAGTTAAACATTAACTAGTAGTTACTTATTAACTTATGA
CTCATGGATTAATTATTAACTAGTGACGTCACTAGTTAATCATTAAGCTTTCTATGCGTATGCATGAGAGATTCATGCGT
CAAATCAACAGCGTCAAATGACAAGCACAAGAACCGCCCGGCTGAAGCCCGACGCAGTAACCCATAGGATGTCCGACACC
GATGTTAGCTTCTTCGTGGTACGGATACCACAGCTCCTTGATGTCTTGAACTAGCTTCCAGAAGATGGCATCGTGCATAC
ACCACGGAGGTACGGCAACACCAAACACCACGTACAAAGGCATCTCCCGACACTCTGCAATTACAACTAGCATCAGAAAT
ACATCCAGCCGCTATTTGAAAAAAACAACAGGATCTCACCCAAAAAGAAAAAGTACTTACCCCGAAACCACCAGGAAATC
CCCCTTACGTGATAATCCGGATCTCGCTGACGCTCAAAGAAGCCGCCTTAAATACCGCTCCTTATCTCTCTTCGATTACC
TCAGTTACGCCCATTTCTTATCAGGTAAGATACGCAGGTAAGATACGCCCTTCCACATCAGCACGGAATGTGCTGACCAG
CTTACCGCGCCCGTTTTTAATATCCGTTAATTAGTAACTTAGGTGAATCACCAAACCACCTGCCGGCATATATCTACACC
CTTGATACGGCGGCATCCATTGAAGTCGAGCGCCACCATGGAGTCAACTACCGTATCCTCGATTCTGCTCCTATCCTTCT
TCGTATCTTCCATCGAATCCTATCCGCTCCTGCATAACTTCACGGCGCTCACGGGATCCGTGCTTACTCTTCCCTACAAA
                                                            BamHI
GGACATGACCGACCCTTTAAATTCGAATGGCGGCTGACAGATCAGACCAAAGTAGCAATCTCGGATCCTAGCACCGGCAT
                                                                  BamHI
CAACTACCCGTCGGTCCACTCAAAGGAAGAGTACATCTAAACGGCAGCGCCCTCATCGTTACATCCCTACGACTTAGTG
ACGCCGGTACCTATACAATCCTCTCAGAGGACAACACAGGAACTGAAATCGGATACTCCTATTACGTCGAAGTCAGAGGT
ATAGAACTTCCCCTCCTTTTTCTACATGATATCCCGTTCCCTCTTTTTTCTTACCCCTAGCTTATTCTTCCTAGAACCG
ATGCAAGCTCCCACCCTCTATACGGATCGCTACAATGACTCATCTCCCATACGCCTCACATGCCAAGCTTCCAACAATCT
CCACCGTAATATCACATACCACTGGAAAACAGATTTAATACAGCCAACTAACTCGACTCGATCTATCACCTTAAACATCG
AAGACTATATATCCGTTACCTGCACAGTCACTGATGGAGTCAGCAAAAACAGCATCACGATTATGGTTCCGTTGAGAGGT
AGTATTCGGTTTCCCGTTATCTCCCTATACTACGTAATCATGCCCACCCTTTTAACCCGTATCTTTACAACAGATCCTTC
TCCACCTACGCCTTACGGTTTGCATCCCACTATCATTTTCCTGAGTGTCCTCTGCATGATCCTCATCACCGCAATTACCG
TCTACTTTGTGAAGAAGCATTGCTGCGATAAGCAATATAAAATAACTTGCATTAACCCTTACCGAGAATGCTTCGGTGGC
```

TABLE 10-continued

Nucleotide Sequence of the right hand end of fowl adenovirus serotype 9 (CFA19) genome

GCCGGTCTCGTTTAATCTCGTTTAAATAAAAACCACTATAATCCCCGCTTCCTATAATCTCTACTTCCTATGATTAAATG

GGTAATTAAATGATGGGTAATTAAGTGGTGTCAATGATCAAATAATGATTCGGAAACGATTTCGGGAAAAATGATTTTAG

GAATCAATGATCATTATCAAAAATAAATGATTTATTTATAAGACGTGTTTTTGATGATTGATACGATTAGTAAATCACAT

GATTAGAAACACATGATTAGAAACACAGTTTAATCATCAATCGAAATCACCGCGCAAGATATGGACAGTCACGTTCTCCT

CTGATGTCCTATCCATAGATTCGCTGTCCGTAGAATCAGAGGCGCAGAGCATCCGCCGAAACCAGAAAGTTATCGCTACC

ATCAGCAATAACAACATAATTAACGCGATCGGCAGCCACACTGGAAACTCGCCGGTCTGATTGGATACCAGTCCTCCGCC

GGTCTTATAAGTGGTCTCCTCGATCTTCTGATCCTCCTGAGTCAAACCAGGAATTACCACTACGTAAAATCCGGTCTTTG

AATCCTGTTGTAAGTCTAGCGTATTAGTATACAGTCCCGAATCGGCAGGTGTTACGTCTCTAATAGTAACGCAATTGGAT

GTGGCATTGTAATGCGTGCGGCTCTTATAGTTAGCATACACTATGGGGTTACCCAGAGCTTTATAAAGCTGTAATACGAA

CACGGTAGACGCGTGCTCGTTAGAGGACTGAAACTCCCACTCCGTTATAGAAGCGGAGCTAGCATCCTTCCCACACATGC

GTAACTCTCCACCTTCCAAAACTAATATACGGCTCATGTTATGCACCTCAACCGTCGCATTGCCCGTAATATCCTTCACG

GTATACTGTATGGCATACGGTTTCCCACCGACAAAGGAACCGTAAGTCAACCAGCACCCGTTATTAGCCTTCAGCTTACT

CAGGTAAATAGTATTGCAACCACTATCTACCCTCGTTCTACCCATGTACCCGCTTTCAAGTCCAGGTTCTTTAACCCTCG

GAATCACAAATGCCGCCCTCTCCATCTTATTGCAATTGGGGGACGGGGAATGATACCAGAGGATCATAGTATGGTCCCTG

CACTCTCCTGTCCGTAGAGCCAGCTCCGGGTCCCGGGGAGCGCCAAAGCAGAGTCCCAGGACAGCAGCCAGCAGCAGGGC

AACGGACTTCATGATGAATGCGGGAACCAGCCAGCAGCAGCAGGTAGAAGGTGCGAGTACTCGAGGCAGGCGGGAATAAC

ACCGCACGCTTTCCACCCCGCTTAAATACACAACCCACACCGGTCATGGTCAAACATTACCTAGCCTACTCAGCACGGAA

AAGTACTCACCCTTAACACAGTTCGACTTATCAGGTACACACCCGTAACCTTCGCACCCCAAAGCGCACAGTCAGCACCA

TAAGGAAGTCGTAAAGTTACCCTTTGATTGCATTGTCATCATAAAAAACGCTGAGCAAACGGAAACGCCCCAAGTACAAA

TCTCTCTTCCGCCACGCCCTCGTTAATCAATAACTAGTCGCCGATACATATATACCCCCTCCGTTCCATCACACCTACAC

TACCTTCTCTCCGCACAGGCAACATCTCAATCCTTACTCTTCCGAATCCACTTCGCCGCCTTCGACATGAATCCGGTAAG

TATCAACTTTTTTCTAAGCTTATGCTTCTGACACCTCTGATCTTAATACCGCACCCCTTTTTTCTCAAAAAAGGTTTCGT

GCTTAACGCTTCTTCTATGCGTCATCATCCCGAGAGCCGATCCGCTTCCAATCACCCCCGCCTCTAAACCCGCTACCGAC

TCCGCCCGGACCGGCGCCTCCGTCATCACGACCCACTTACCCGCATCTCCGAGCGCCACCCCGTGCGACGAAATCTTGAG

CGAGGACTGTTGGTTCGAAAATGCCAGCGGTGATTACCAACCCCTACCCTGGGAACCGAAAGAGGAAACGGTTTCAGATC

AAAACCCTCTCACCGCAACCGACCCCATCGGTGACCGAATCCCCGCTATCATCCAGTCCCAGTCCCGCGCTTCTAACCGT

CCGACCAGTAAGGAACACACTTCTACTATCGCATCCATCTCGACCGTAGTCGGCATCGCGGTCCTCGTCATCCTGACCCT

CGTAGCCTACTTTACCAAGTACCCCAAACCGAGACCGCCCAGATCCATCTACATAGGAGTAGCTCCACCCGATATGGAAC

TCAAGGAAATATAATTCCAGCCCCACCCTTAACCCTACCTTTCCATGAGTCAGTATTTTCAATAAAGTTATATTGCAGTA

TTAATTCCGTTGTTTCCGCGTTCTTTCTCTCGCGCGGACAAAGTCCCTTCGACCAGGAAGTCCGGTATACGTCATTCCGC

GGTGTCATGATGACGCGCATAACTCACGACTGCCATCTGCCGGACAAACGCGGTACTACACTTAACACATAAACACCCGC

CTTTTTTCGATTCCCACCATAATCAGGCTTTGGTAAAAATTCGCAGATTCTAAAATCCGTATTCCTGCGCCCGCGATAAT

AGATCACGCCCACGACACGCCCT<u>AGCGCT</u>CTTATCACACGCTCTCTGCTGCCATCTAGCGGGCGGGAGCGGTAGTGCGAG
                      Eco47III

GTGACAGCAGCGTCATTCATGTAGGTATATATAGATGATG-

TABLE 11

Nucleotide Sequence of the right hand end of fowl adenovirus serotype 8 (CFA40) genome

```
AGACCTCGTCTTCGCCACGGTCAAGGAGAAGATCGGCTGGCGGCGGTTCGTGGAAGCTATCCAACGGTACGTGGCTGACG
CCTACGGTGCTTTCCTGACACTCAATGCGGAAACCGCACCCGTCGGGGGTGACGAAGATAACGCCGTCAGTGTGCTCATT
GACACTTTAGGCGAAGAAAGGGCTATTTTAGCAGCTTATCGGGTGGCGGAAAAGCTATTAGACGATAAGCCGCTGCCAAA
CGACGGCGAGAACAATGGGTCCGAAAATCCCCGGGACGCCGCGCATACTTTTGCGGAGAGTCCCGAATCGGACGAGGACG
TACAAAAGGCGTCCGCCGAGAGCTCTCCCGACACACCAGCTCGAGACTTTACCGCGGAAGCCGTAACCGTGTACATCGAC
TCGGACGGCGGTTGCGAGGACAGCAGCGAAGAAGATCAGGAGGAAGAGGAGGAGGACGATGAAGAAGAAGACGAAGAAGA
AGAAGACGAAGAGGAGGAGGAGGAAGAGGAGGAGGAGGAGGACGACGGAACACCCGAGTCTACCCCTTCTACCGTCATCG
AAGCGGCGAATCTCTCGCCGGTCGGCACCGACGAAAAGCACGGGGAACCCGACGGCGAGCCCGATGATGGTGACAATGAC
GACGGAGAGGACGAGGGAAGAAATTCTGACGAGGATAGCGGATACTATTGGGGGGATGACACCCCCCTGGAATTGGTTCG
CGATCGCGGGACAGGCGATCACGGTGAGCCAGATAGCACCGCTCCTTCCGACGGTCCTGGGGAAGCTCCGTCGGCCGACG
GGGTAGACGAGGAGCAGGAGCAAGACGAACAAGAGGGAGAGACCGCCGTCCCCGCCGCCACCGCTCAGCCCGCTTTCGAC
AAATGCCTCCAACGGCAAGCCATGATGCTCACCGGCGCTTTGAAAGACGCCTTACCCGAGCAGGAACGCGACGTGCCCCT
CTGCGTCGATAGCGTGCAATACCAGCTCGAGCGCTACATCTTTAACCCCGATATGCGTGTCCCTCCGGAATACCGCGAAG
TGCGCTTTAACTTCTATCCGCCCTTCATGCGCCCCAAAGCGATCGCGAACTACCACATTTTCGCCGTCACGGCGCCCATT
CCGGCAAGTTGCAAAGCCAACCGCAGCGGGAGCCAGCTCTTAGAAGCTTGTCGCGACATGAAAGTGTTCAAGCGCTTACC
TCGTTGGCGCCTCAACGTCCAATCCGACGACGGGCTCGGGGACGAAGTGGTACCTGTAACAGAGCTGACAGATGCCAAAT
TAGTCCCTCTCAAGGACGACATCTCGCGGTTGCAGTGGGCTAAAATGCGCGGTGAACACATCCGCTTTTTTAGCTACCCT
TCCCTGCACATGCCTCCCAAGATCTCACGTATGCTCATGGAGTGTCTGCTCCAACCTTTCGCAAACGAAAACGACAAGGC
GGAACAGGTCGCCCCCTGCGTGAGCGAAGAGGAAATGCGTTTTATTGTAGATCCGGAGCAGAGAATGAGAGGCGAGGAAC
TCTACAAGGCCATGCTCAAAAGGAGGGCCGTCGTTACCATGGCCGTGCGGTACACCGCTTTGCTCGAGCTCATGGAACGC
GTCTTCCGAGAGCCTTCCTCCGTCAAAAAAGCCCAAGAAGTGCTCCATCACACCCTTCATCACGGCTTCGTGGCCCAAGT
GCGCGAAACGGCCAAAGTGAACCTGAGCAACTACGCCACCTACCACGGCGTCACCTACAACGACCCGCTCAACAACTGCA
CGTCAGCCAAGCTTTTCGAAGGCAGGGACAAGGAGGATTACGTGCTCGACACCGTCTACCTTTTCTTGGTCCTCAATTGG
CAAACCGCGATGGGTATGTGGCAGCAAGCCATCGATGATACCACCCTGGACATCTACGCGAAAGCCTTTACGCGCCAGCG
ACGCGCCATTTACGGCCTCGGAAGCGTCACCGAGGTCAGCAAGGCCATCGTCGACATCCTGATGGACGGGGACAGGCTCA
CGGAGGAAATGCGGAAAGCCCTCCCCAACTTCGTGACGCAGAGCCAGATCTCCGATTTTCGGCACTTTGTCACCGAAAGG
TCGAACGTCCCCTCCATGGCCGCCCCGTTCTACCCCTCCGATTTCGTCCCGTTGGCTTTCCGGCAAAGCGCCCCTCTGCT
CTGGGACCAGGTCTACCTCCTCCAGATCGCCTTTTTCCTCACCAACCACGGAGGATACCTGTGGGAACCGCCCGAGAGCG
AAGCGCAGGTGCCGCAGCACCGCACTTACTGCCCCTGCAATCTCTGCAGCCCGCACCGCATGCCGGCGGATAACGTCGCT
CTGCACAACGAAGTGCTCGCCATCGGCACTTTCGAGATTCGCAGCGCCGAAGGCAAATCTTTCAGGCTCACGCCCGAACT
CTGGGCCAACGCCTATCTCGATAAATTCGTGCCCGAGGACTTCCATCCTTTCACCGTGTTCCACTTTCCCGAAAACCGCT
CTTCCTTCACCAAAAATCACACCGGTTGCGTCACGGAAAGTCCGGAAATCCTCTCTCTGATTCGTCAGATCCAGGCCTCC
AGGGAGGAGTTTCTCCTCCCCGAGCAAGGGGCTCTACAAAGACCCGCAGACCGGCGAAACGCTCACCACTTCGGTCGGGG
CAGAGAACCGTCCTGGAGCCTCCGGCGGAGCGCCTCTACCGCCCGCTGCCGCCAGTACCTGCGGAGGAGCTCGAGCGCCG
CCGAAACCTCCTAGGGCTCTACGGTCTGCCTGCCCTGCTGCAGACCCGGACTCCCAGAGCGACTACGGGAAGCTGCTCT
CGCGTCCAACTACGGCCGATATGGCTCAGAGGATGCTGGACGAGAAAATCAGAGTTACCGAAGACCCTCCGGAACCCGAG
AACGCCGTTCCCTTCCCTACGGACGCCCGGTTCGTGGGGGTTCGCCCGTGCGGAGGACCTGAAGTGAGCGAATCAGACGG
AGAAACGTTAGAAGCCGGACACCGAGAGATCTGAGTACCATCTCGGAGAGGAGGAGGACCTCGAAGAGATGGAGAAAGAG
```

TABLE 11-continued

Nucleotide Sequence of the right hand end of fowl adenovirus serotype 8 (CFA40) genome

AATATCCCACCGCGGCCCTCCTCGCTGCCTCTGGACGGGACGCGGAACCGCAAGCGCCGCTCCGCATCCTCGCCCGGGAA

GGAGCTGAAGAGGCCTCCGATCCGAAAGAGAGCCAAATCCGATAAACACGCGGAGACCGCGCCCGCGTCCAAAAAGCGCC

GTCCTCGAGGTAACTATAGAAGCTGGGTCAGGCACCGCGTGGCGATCTGCCAAGCGCTCCGCGACGCCGTTTTCGACCGA

AGGCTGGCGGCCGAAATCCTAAAGAGAGCGCGCGGTATCTTCGTACCGCCCACCGTATTGGGCTACTACGCCCGCAAACT

CCTAGAACTTCCCGACGAAGATCACTGATCGTCGGCTTTTTCTTTCTCCTTTCCTTCTTAGCGGCTCCCGCTACCGCCTC

TGACACGCTCCCTCCGCCTCTCCCGCCGAAAAAACGCCCCAAAAATACGCCGCGGACCGACTCGTCCTTCGAATTGGTCC

CTCCCGAGGTCGCAGACTTGAAAGCCAACATCCTCGACGTGCTCGTCGAAATCGAAAATATCGCCAAAAACGACCCTTCA

CGGCGCGTTTCCATCCGCAACCGCACCCGGGAAAGCATCACTCGGCAGTTACACTACGTCAAGGACGAGCAAAAACTCAC

CAAGCTTAAGGCAGATGCGGAAAAAATCCTGCACCTGTGGAAATCCCTTTCCTAATCCCGCTTCTTTTATAGCGCTACAG

ACCGCGTGACTGAGCCCGCGGCAACATCATGAACCTCCTCGAAGCCACTCCTACCGAGTACGTGTGGAAATACAACCCCC

TCTCCGGGATTCCCGCCGGCGCGCAACAGAATTACGGAGCGACCATAAACTGGCTCCTCCCCGGAGGTAACAGTTTCGCT

TACGCGGCGGACGAGATAAGACGGCACACCCTAAGCCCTGCCGCCACCCGCGCGATCACCGAACGTTTCGAAGCTGAGTC

AGACCAGCAACCCTTCGCCAACGCCCGGGAAACCGCCTAGATCACCGCCAACGTGCTGGACTCTGGCTTTCCAAAGTCCG

CCGTGTACCCCGTGGACCCTTCCGGACTTCAACGGGTTCAGCTCTCGGGCGGCGCCGAGGGCCGGATGCAACTCGCGGGT

GGCCTCACCGAAGGTCGACTGCAACTTTCGGGAGGTGTCCTAGGACACGTCGTGCCTCCTGGGGGAGAAGACGCGCCGG

CGGGCGTCCGCCGCGATGGTGTGGGACCGCTCTCGCGGGAAACGGGCTTCCCGAGGACGCCGAAGTGGTTTCGGATACCT

ACAAGTACTTCCTCCGCACCCAGGGACCCAGCCAAGTCGTGCAAGAACCCGGCGTGTACTCGCGGAGGCAGTTCATGACC

ACCTTCCTGCCGGCCGTGGTGCCCCGACCTTTCAGCAGTCCCAATCCGCGCGACTTTCCCGCGCAGTACAGCGCCATCTA

CAAAGGCACCAACGCGTACGAGGACGTATTTTGGGACTGGTGAAGTCCCTCTTCGCGGCTTACCCGTTGCTGACGGTGCT

CTGTTTCGCAATAAAGTTCTTCCAATTCAGCCTCGCTGAACGGTTCCCGCCTCGTTATTGTCACGCGTTCGCCTCCGTCG

CTCACCACGCGCGCGAAACCGTCTTTTGATCCAAAAGACGTAACCGGGGTTTAGGGGTTGCGCAAACCTCACGATCGC

CTGGTCGTTGACTTTCAACCAATATTTTTTAGGAGCCTGCGACTCCGTCTCCGACATGGCGACCTCGACTCCTCACGCCT

TCTCCTTTGGCCAAATCGGCTCCCGAAAACGCCCTGCGGGTGGCGATGGCGAGCGAGACGCCTCCAAAGTGCCGAAAATG

CAGACCCCCGCTCCGAGCGCGACCGCCAACGGAAATGACGAGCTGGACCTGGTCTACCCCTTTTGGCTCCAAAACGGCTC

TACCGGAGGAGGCGGCGGCGGCGGTTCCGGTGGAAACCCGTCCCTCAACCCGCCGTTTTTGGACCCCAACGGACCCCTGG

CCGTCCAAAACAGCCTCCTGAAGGTCAATACCGCAGCCCCCATCACCGTCACCAATAAGGCCCTGACACTCGCCTATGAA

CCGGAGAGTCTCGAGCTCACTAACCAACAGCAACTGGCGGTCAAAATCGACCCCGAAGGACCTCTGAAAGCCACGACCGA

GGGAATACAGCTGTCGGTCGACCCTACGACGTTGGAGGTTGATGACGTCGACTGGGAGTTAACCGTGAAACTCGACCCCG

ATGGCCCCCTGGATTCCTCAGCCGCAGGAATCACGGTCCGAGTCGATGAGACCTTGCTCATCGAAGATGCTGGATCCGGA

CAGGGCAAAGAACTCGGAGTCAATCTCAACCCCACGGGACCGATTACGGCCGACGAACAGGGCCTGGACTTAGAAATAGA

CAACCAGACACTCAAGGTCAACAGTGTCACCGGCGGGGCGTCCTAGCTGTACAACTCAAATCCCAAGGTGGACTTACCG

TACAGACTGACGGTATCCAAGTGAACACTCAAAACAGCATCACCGTTACTAACGGAGCTCTGGACGTGAAAGTAGCCGCC

AACGGACCTTTGGAATCAACCGACACCGGGCTCACACTTAATTATGACCCCGGAGACTTCACAGTTAATGCGGGCACGTT

GAGCATTATTAGGGACCCGGCTCTCGTAGCCAATGCGTACCTCACATCCGGCGCCTCCACCCTTCAGCAATTTACAGCTA

AGAGTGAAAATTCCAGTCAATTTTCTTTCCCATGCGCATACTATCTGCAACAGTGGCTTTCCGATGGGTTGATTTTTAGC

TCCCTCTATCTGAAGCTCGACAGGCACAGTTCACGAACATACCAACGGGTGAAAATTATCAGAACGCCAAGTACTTTACC

TTCTGGGTTGGAGCGGGCACTTCATTTAATCTTTCTACCCTTACCCAACCCACTATTACACCCAACACCACACAATGGAA

TGCATTCGCACCTGCTCTTGATTACTCAGGTGCTCCTCCCTTCATCTACGACGCGTCTTCCGTAGTTACAATTTATTTTG

TABLE 11-continued

Nucleotide Sequence of the right hand end of fowl adenovirus serotype 8 (CFA40) genome AACCCACCAGTGGTCGACTGGAAAGCTATCTCCCCGTCCTTACCGATAACTGGAGCCAAACAACCTACAACCCCGGCACC
ATCACCCTGTGTGTAAGAACGGTAAGGGTTCAATTGAGATCGCAAGGGACCTTCAGCACTCTAGTCTGTTACAACTTCCG
CTGTCAGAACGCGGGCATTTTTAACAGCAACGCTACAACGGGAACCATGACCCTGGGTCCTATCTTCTGTAGTTATCCTG
CCTTGAGCACCGCCAACGCTCCTTAATTCAATAAAAAATGATCCACACAATATGAAGGTCTACTGTGATTTTTTATTAAA
GCAGCCATACTAATTCTCCTGGATACCCATCAGTCTGTCCCACTCTCCGCGTTGCCAGTAGTACAGGCAGTTCACGGCGT
CCACGTACCACGATTCGCTCACCAGAAAGACCCGCTGCTCGGGAAAATCCACCATCATTCTGCGGATGTAGTGACAAGGG
AGCGCCCCCATCTGGCCGAGCGTGGCCACCGCTTCCACGAACACACCGGTGTTGTGCGGAGGGACATAGATGATCATGCC
CAGAACTCCTCCGCGGGCGCGGCGCAGAAGACGGGATAAAATTCGGTAAACATGACAGAGGCCCACGCCGCTACGAAGTA
CACCCCTTCCAGACTAGGGTCGCCTTCCAGCCTGCTCCAAAGGTACACGGAGAGACCACTGCTGTCGGGTTGACTGCACA
CGGCCATCGGCACGCGTCTCATCTCGAATCCGTGGCAGTGACACCGCTCCGGAATCATCTCGAATTCTTCCAAACATAGA
AACTGGTGCGCGTGGACGGCCGGCACGAAACGCAAATCTCCTTCCCCTGCTCCCACCGCGGGTTGATGTTCCCCTATGTC
TTCGCCCCATAACCTCTGAGCGGCCATGATCTACACCTGGGATTCTTCGCGCTCTATCTCAGTATACACGTGTTCCACAG
AGCCGCCGTAGACCTCTTCCTCGTCGCTACCTGCCGGTGGCGCTCTCAGCAACGACAGTTCCAGTGGTGTCGGCGGCGGT
GGAACAGAAGGAGGCGGTGAACGGGTATCCGAGCGGGAGTCGTAAAACGGATTGCTGCTCACAGTCCAATTGGGGGAACG
AGCGGGAAACTGAGACAGGGAACGCAGCCAGGAGAACCGACGTGATGGCTCGCGGTTATTAGGCAATGTGGGGGTAAAG
CAGAACACCGGCGACGGATACTCCAACGGTGTCCTCGGATGCTCTTGAGGACCTCCCGCAATGATTCTCCGCCACTGCGC
GATCAGCAATACAAACGCGATCGTGGCTAGAAGAGTGCAACAGCCAAACATCATAAACACGTAGGGAACGGCATGTAAAT
ATTGACTGAGGAAGAGATAACTGGCGGCCACCGCACCGCAGTGAATGACTCCCACGGTCACAGCCAGAAGCAGCAGAAGG
CATGCCTCTCTGCGGCGCCGGCGGATCCGCACCTATCAATAGAAAAAGGGGACTTTCTATCACCCTCCACGCGTGCCCG
GCGCTTGGACATGCAATTCCGCAAATAGGACAACTGAGCTATAGTGGCTAGGGGCAAGGGCTGTCTAAGAGGGCATCCGG
GGCAAGAAGCTTCGGGGTGATGGTCGCAGTACGTGCCGTGAACATGCAGTACCCATTCTTCTACATCCACAAACGTGGCG
CTACGGGAAGCGGAATGTAGCATAACCCCCGCGACACCATGCTCCAGCAAGCGGGTCGGCCATCTCTTTCAGCATGGAT
CGGGTCATCAGAGGCTGGGTCACGGGACTGCCCTTCCCGCAAGTTTTAAGAATGACGGTCGCTACCACATTGGTGCGACA
CGCACCCAGATAGAACGGGATATTTCAAAAAAGGCAGGTGCTCAGGCACGACCGTCTGGGAAACCTCATAACATAATG
ATTGAAGAGCCAACCGAAAGGCAACACCGGTCTCTAGAACGAGTCCCGTATCTACAAACAGAAAGTCGGTTTTGTTTTTG
CGAACCATCCATTCCCGATGTTTCTCTATCAGAGGTTCCCGCGCTACGAACAGACGCCTCGAAACCGCTCGCAGGATCTC
CTCCTTTTCCGCGGGTGATAAAGACAACCGAGACTGCAGTCTCAGTATGACGTTCAACAGAACGCACGGTCCCGTCTTGA
GTCTGAGATACTTCGAACACCTGCAGCTCACTACCGTATACAGGGACTCGTGCCACGAGTAATGCTGGGGTTTATCGAAG
AGACTAATGGAGGCTACGGAACGGCTCGTGTGATACTCCATCATGCGTTCCGCTGCTTCTTGGGACGGACCCTGTCTGAC
CAGGATGCTGAACCATATGGCTCCGCATTCGTTTTGATAGCCGCAACCGCGGGTAACGGCAACCACCTCCTACACGAAAG
AAAGGGGCGCCTTAAGTTACTCAAGGAAACCGCCCGGGAAAAATCGGGGCAATGAAAACCTATCACTCACCGAATCAGAA
CACAGAGGCATGATCCGTAACTAAGACACCTCTTTTATTGATCAGGTACCGTCACCTGTAAAGATACACACATTAAACGA
TACGGTAAGAGTCACCGCGGTAACACCGACATCGGTAGTGGCAGAATATATAGAGCACGACTGCTGTCGTGAACAGAGCA
CCTACGACACCACCCGTAACAATCGCGAGGCGCGCCCCATCCTCTTCCCAAAATTCACGGATCAGAGAGTAGAACTCTCC
TCCGAGCTGAGGAGACGTAGGGAAGCATCCCGTAGACCCATTGCTACTTTTTTCCGTCGGATAGCGGTAGAGACCAACAC
ACCTACCATAGCCAAAAAACACAAGCCCCACAACCGTTAAAAAAGAGTTCCGGTAGATGCACCCGAGGCCGCTACTCGAG
AGCCCTCGTCTATGGCTCGCAAGGCGACGGCTTGAACCGGTTCGGTTTCGTTTAGCTGGACGGTCACTACCTCCTCTTCT
GACGCGGTTTCCGAAGTGCTCCAAAAATCGCTTGAACTCGGTGTAGCTGCTGAGAAATTCCAGGTCGAAACGGTCGATGC TABLE 11-continued Nucleotide Sequence of the right hand end of fowl adenovirus serotype 8 (CFA40) genome

GGAGTCTGTCGATGTAGAGTTCAAACACGCAGTAGGTTCTGGCGGGAACTCCACAGAAACGGGTTCCAGTGGGCTTACCG

TTACCTTCAATTTTATAACTTCAAATTCAAGAAAGAATTCCAGTTCGAATACGTCGGCATTAAAGAAGGTGACGGTAAAT

TCTTTCTTCATTCTGTCCAATTGGAAGACACACTGCGCAGCTGTCTGACACACGTCCCAGAAACTGTACACTTTATGGGT

CCCCGAAGAATCCGTAAGTTGGATACTCGTCAGCCAGAAAGGAGACTTGCTAAGATCTACCTTGAGTCCATGTCCCACTT

TCACTTCTACATCAGCCAGCTGGATCGGAATCATAGCTATCGAGGCATCTCTATCCGCCAGGCAACCAGACTGAGGAGGA

ACACTGACTTGAGATCCGCCGTTCGGATTTAACATCGTGCGATAACTCATTAGGGGGAATCGCTCCTTGGTTACCATGCA

GTAGTGCGCAGGCCGACCGAACGGATCTCTTGTAGGGTTACAGTGCATGGTACGCACACACCCTCCAGTCATTACTTTAC

GGTCCTTTATCGAGGGAGCGCTTGACGAATCCTGATAGAATCCCTGTGGTGTGATCACGTACACCAGGTAGATACTTGCA

GAAGGATTCCAGTGACGGATCCACAACACCTCTTCTGCAAGCTCGGTGTAACCCACCGCGGTAAGTACATCATACCTCCC

ATACCGAAGTGTTTGCTCACTGTAACCTCCGATGAACATTCGACTCCACTAGAAGCTACTACTATGATCATGATCGGAG

TTACAAAGTCCTGCTTGAGTACGGGTGAGTACGTAATCTCAGTCATGTAGCTAATGCTAATATGATTGAAGTAGCTAGCG

TATCTGTAATCTCGACTCATAGTATACCCATTCCAAGTGCTCCGGACAGGACCCACTTTGAAACCCTCATTAAGCAAGTG

AAACATGGGTAACCCAGTTCTCACATCCAAAGTCTTTAGAAACTTCGGTACTATCAATCTATGAAAACAGCCGCTTTTAC

TCCACGTATCCCTCCATGAGAATTCTTCGCAGACCGTCTGTCCCCATACACTTTCTGCACACACTCTTCCCGACCATCCC

CCATGAATCCCACAACCTCTACCGCCCTTATCCTCCAACATGATATCCTCAGAAGCCGTATACCCTCCTGTAATCCACGA

CCCTTCCGTTTTCAGGACTGCCACGTAATCCGCATCATTTTTATCTAAGCCTCCGGTAACAAACGTGGGCTCTAACCCGA

CTATTCTGGTACACCGTCTATCCCCAGAAATATATGTCCACTGTCTGCAGATAGTAGAGCAAGCGTGAGCGCCGGCAGAA

TGTCCTATACAGTGTAACCTTTTCGAATGTGGTATGTCCGACAGAAACTTCCCGAAATCAACATACAGACCGTCATAGTC

GTAGTACAGGTTCCAGTCCACCAGGAGCAGCGCGACTGCAGGCGTCATATTCTGATGGACACGCAACACCTGTCTAAAAC

TTTGATAGCCCATGTAATACCCCGGTATAAGCACAATGATATCGGTCTTGCCGGCTAAAGCACTGTGCAATCGATGGTAG

ACACCGTACTGGTACGTCACGTCGTGAAATTTCGGCACACCCCCGTGAGCTCCATACCACGTAATCTTCGATGGCGGTCG

GCTCAATCTTCCAACGCCTCTCGGAGCATCAAGTTTTAGAGAATCCGGTCTCGCCACGCATGACCGATTGCCCGAATCGG

GACATGCAACTGCCGATTTCGCACACGAAAGCACGGAGGCTCCGAAGAGCACCCCGACCAACTGAAACAGAACGCATGAT

TTAGACCCACTCCCGACAGAGGATTAACGCGACCCAATCAAGGGATATCAAAAAAGAATCCTTACCGCGGAGAGATTCAT

AGACCGAAGAGTTGAGAGCGCTCCTGTTTCTCTGAAGATCTCTCACCCCGACTGTGACAGATCCACAAAGCAGCACTCAA

TTTATACTGTCAAATGGTTAATGTTTAATGCTAGAAAAGCGCTGACACCCAGTAAATATTTACTTAGTTTGCAGTTCCAC

TGTTTCCTTATTGCCATGACTGGACAAAAACCACAGATAAGATGTTCCATTCAAGGGAACCCGATGTTCCCTCGATAACT

TCCCGGTACAAAGTCCAAAAATAGAACTAGGTGCTTTATAAATACTAAGAGTCGACTCCTTGGTGTTTCAGAAGAACACA

GACGATCTACAAACAGGATGAACCTCGGAAGACTCAACACCGCCGGTAAGAACATCTTAATTTTTACTTTGTATGATTTT

CAATTCTGAAAAACACGTTTCCTGGTTCGTGCACGTACGCGGAAACGAAGTTCGAAAAATCAGAGTTGGAATTTTCCAGC

TATGGTTAACTATTAACTATATGACGTCACTTAGTTAATTATTAACGATATAAAGTAAATGATTAACTCGGGCTAGTTAA

TGATTAACTATACCTGGTTAATGATTAACTGACTTAGTTAATGATTAACTAGAAGTTAATGATTAACTAGAAGTTAATGA

TTAACTAGAAGTTAATGATTAATCTATTACGTCACTCGTTATATATTA<u>ACTAGT</u>GACGTCACTCGTTATACATTAACCCA
                                                                                      SpeI

TTACGTCACTCGTTATACATTA<u>ACTAGT</u>GACGTCATGAGTAAATCATTAACCTTCATGCATATGCATGAGGAGCTACTGA
                      SpeI

ATATGCATGAGAGCCTCATACATATGCATGGAACTTATGCATATTCACGACACTCATGCATATGCATGCATTGGTTAAAG

AGTAACCCTATGACTCAGTGTGTATGTTTACGTTGCCTAGCAACGTTAATGATTTACCTGCTGACGTGGCAGCTCCGCCT

CCAGGTAAATCATTTACCTGAACTTTGTTCTTTATGTTTATTCACCATGGCAACGCTACCATATATGGACATCCGACTCC

TABLE 11-continued

Nucleotide Sequence of the right hand end of fowl adenovirus serotype 8 (CFA40) genome GCCTCCCCCGTTATACATTAACGATGGCGTGATAGGCGGAGCTCTCCCCCATTGGCTCTCAATGACGTAGTTCAGGTTAA
CCATAAGCCAGAACCGCCTATATAGGTAGAGCAGGTAGACCCGGAACACCATTCCCATCCGGACCTCCATAGAGTGCGGA
CCTCTACGGGCTCTCCATACCGGTAAATATTTTATTCCATTTAATCCAATCGAATAAATCAATAATCAACTCAATGCTGT
GATTCTGCCTCAAATTCAATGGTGATTTTCTTTAATAAAAAGCCCACCCCCCTTGGCACCCCCCTGTACACCCCCCTGTA
CAGGCGACCACCCCCTATGGACACCCCCCTGTACAGGCGACCACCCCCTATGGACACCCCCCTGTACAGGCGACCACCCC
CTATGGACACCCCCCTGTACACCCCCCTGTACAGGCGACCACCCCCTATGGACACCCCCCTGTACAGGCGACCACCCCCT
ATGGACACCCCCCTGTACACCCCCCTGTACATTTTCTCCCATAGGCTACAATGGAATACTGCCCCCTAGTGTCTCCTGCT
GTATGGGACCCCTATGATGTGGGCGCCATTACCTTTGCCACTATGGAGCTCCTTCACGAGGGGGCGCCATTGAAATTGGG
AGACCGCATAGAGAGCCTAGCCAATGGGGTGCTTTGGAATCCGGATATCCCCGTCCAACTCTTCAACTGCCTTTCCATTC
GCTCATGGGATCACATGGGAAGCGCGTCATGTACCGTGGCCACACCTACCGGATGTACCACGCCCAGTTACGGGTCCGA
AGCTCCGCCCCCGTTACTAGGAAACAGGCCGGAAGCCTGCTCCTCAGCCTATCACAGAAGCTCCTCTGTTTCGCCGCCCG
CTTTAATACCCATCCCCTCGTGATGCAATTGGGGGTGGAGTCTAACCCTATGGGCCTACCTGTATATACCAAGAGGGCCC
TCCAGATGGCGCTACAGAGTATGCGGGTGCGCATTGCCCCTGACGGCCAGAAGGTGGCGCCACCGGAGATAGGCAAGACC
TGTACGGTGAAGCCCCTCAAGACCCCGGAGACCCTCCAGCAGGGGGTCTTCAGTACCACCGATTTAAAAAAGACACTTCC
AGATTGGGCTTTTCGCCGACTTTTTAACCAAACCCCCTATATTTGTGGATGGAAGATTGGCACCGCGCCAGAAGGGCGG
AGAGTTGGATCGTTACGCTCCACCCCCAGCCTTCGACTCCGCCCCCCACAGGGACCAAGACTCCGCCCACTCTGCAGGAC
CTTGCCCGGCTGGGCGTGGTCGAGCAATGCCTCAAGATGAGGAGGCGTGGCCTGGACCGCAGGCACCACCCCTATGCTCA
ATAAACCAATCAGATTCCAGTACTTGGCTCCTCCTATTTGTGGGCGGGACTTTGCACGCCTCTTAGCGGCGCCCCCTGGC
GGCCGAGGGCCGCCACTGCACCCCTGTCGGACTTAGTCTCTGGCGCGGGGCCGGTCAATCATTAACCCGACGGCCGGCAC
GGGCGCCCCTGGCGGCGGGCGCCCGCCACTGCACCCTGCGCCTCTTAGCGGCGCCCCCTGGCGGCCGAGGGCCGCCACT
GCACCCCTGTCGGACTTAGTCTCTGGCGCGGGGCCGGTCAATCATTAACCCGACGGCCGGACGGGCGCCCCTGGCGGC
GGGCGCCCGCCACTGCACCCTGCGCCTCTTAGCGGCGCCCCCTGGCGGCCGAGGGCCGCCACTGCACCCCTGTCGGACTT
AGTCTCTGGCGCGGGGCCGGTCAATCATTAACCCGACGGCCGGCACGGGCGCCCCTGGCGGCGGGCGCCCGCCACTGCA
CCCTGCGCCTCTTAGCGGCGCCCCTGGCGGCCGAGGGCCGCCACTGCACCCCTGTCGGACTTAGTCTCTGGCGCGGGGC
CGGTCAATCATTAACCCGACGGCCGGCACGGGCGCCCCTGGCGGCGGGCGCCCGCCACTGCACCCTGCGCCTCTTAGCG
GCGCCCCTGGCGGCCGAGGGCCGCCACTGCACCCCTGTCGGACTTAGTCTCTGGCGCGGGGCCGGTCAATCATTAACCC
GACGGCCGGCACGGGCGCCCCTGGCGGCGGGCGCCCGCCACTGCACCCTGCGCCTCTTAGCGGCGCCCCTGGCGGCCG
AGGGCCGCCACTGCACCCCTGTCGGACTTAGTCTCTGGCGCGGGGCCGGTCAATCATTAACCCGACGGCCGGCACGGGCG
CCCCTGGCGGCGGGCGCCCGCCACTGCACCCTGCGCCTCTTAGCGGCGCCCCTGGCGGCCGAGGGCCGCCACTGCACC
CCTGTCGGACTTAGTCTCTGGCGCGGGGCCGGTCAATCATTAACCCGACGGCCGGCACGGGCGCCCCTGGCGGCGGGCG
CCCGCCACTGCACCCTGCGCCTCTTAGCGGCGCCCCTGGCGGCCGAGGGCCGCCACTGCACCCCTGTCGGACTTAGTCT
CTGGTGCGGGCCCGAGTCACGGATGGAGTAGTTTCCCTTGCGGCCAGCAGAGGGCATACCTTTATTCTCAGCTCGCAAGT
CTCAATAGATACACACCTCATCGGTGTACAGCGTGTCCGCGTAGCGCAGCCCCGTGCACCTCACCCAACCACCTATATCG
CGAACGGCTCCGGTACTCACTATGTATTTCCCGACGCGATAGTTCGGATCATTGCACCACTTATTCAAGTACATTCTAAA
CCATTGCCCTTCGGGGACTTGGCGCTGATAAAAACATTCCCTGAAGTACCGTTTCACCGCGCGAGAACACTTATACAAGT
ATCTGTCCCGCAGGTTGAACATGGTTAAGCACAGAAGCAAGGTCATGTGGCAGGAACAAGAACCGCCAGGCTGCAACCCC
ACGCAGTATCCCATCGGATGACCGATCTCCGAGTTCGCCTCCTCGTGGAACGGGTACCATAGCTGCTTCACGTCTTGAAC
CAGCTTCCAGAACACTGCATCGTGCATACACCACGGCGGCACGGCAACTCCGAAGATCACGTACAGTGGCATGTTCCGGA

TABLE 11-continued

Nucleotide Sequence of the right hand end of fowl adenovirus serotype 8 (CFA40) genome

TACATCTACGACACAGGTACTGTGACACCTTGCGCGTACGCGAAAAGGGAACCCGACCCTCCCCCGTAACGCTCCACTTA

CGGACAGCCGGCGATGCGCACTGCGAACGAAAAATAAATCTGCGCCGTTGTGCGCTCCAGGCGGAAACAGGGGAATATAT

AAGCCAACTCTTATCTTTATTGTTGCCACGCCCGACACTATCCAGATTTCGAGACCTGCTGACACCACCGGAACACGCGA

CCTCGCCCTCTCTTTATCATCCATACGCCCAGGTGACTCAGTCAAATCCCTTATATAAAGACCGTTTTTACCTGACCGCT

TCCACGTACACAAGGCGGCACATGAAAGCACCATGCTGCGCCCCGTATCCGCCATCGCGTTCCTCTCGTGCCTATGTCTC

ACGCGGACCGCGCAACAGGTCGGTAAGTCCTTTAATCTTACGACCCACTCCAACCTCACTGTGCACCCGCAGACCAAAGG

AACCTCAAAGCAAGAGTGGCGGCTAGGGCGCGATACCAAGATTGCGATGTGGGAGAAAGGCTACGGGTACAGCTACCCGT

CGGGACCCTTTAAAGGCCGCGTAGAAATGAACGAGACCAGTGTCACCTTTTTGACCTCCGTCCCAACGATTCTGCCATA

CTGACTTACTTCTCCGAAGATAGCTCCGGCACGGAGAGTGAATATCCGTACGCCATCAGCGTAAGAGGTGAGCCCTTCCC

TACCTTTGTTCCATTCCGCCCATCGAGCACCTCAGCCGACACCACACATTTTCAGATCCCCTCCGCCCTCCCATTCTACG

GCTGATGACTAACAATTCCCGTCCGCGGACCGAGAGCCGCATGAGCTTGCAGTGCATCGCGCTCGATAACGATAGTTCCA

TT<u>TACGTA</u>CGCCTGGTACACTGACACCTTAGAGAGCGGGGACAACATCCGAGAAGTAACCGTCCGAACGGATTCTGAGGTA
  SnaBI

GCAGTTACCTGTCGGATATCGGATGGACATTCCACCAATTCCGCGACTCTCGTCGTGCCGCTAAACCGAGGTCAGTAATA

TCCCCTCCCTCACCGCAACAGATCCGCACAGTCAGGATCCCAGGCTTTCACGATCCTTTCCCCACTCCTTTAGAACCTGC

CGCTCCCTACGGCGCGGATATGACTACGGTGTTCCTGGCCATCTTAGCCCTTATTCTTCTAACCGTCATCGGCGGCTACG

CCCTCAGAAAGCTGTGTATGCGAAACGAGCGCGTTTTTATTTGTAACCCGTACAGAGAATGTTTTGGCGGTCATCTCTAG

GACAAATAAACTTCTACTTGAAATGAGTTTATTTTTCCCCCTGCCTGTTTGTGATGGGAAATGATCGGTGCTGCTTATGG

ACCGAGATAGATGGAAGGGACGGGGGCATTCAAATTTCTAGGTCCAGGGACATAAAAAAGAGATCAAATTTACATCTCCG

GTAAAGATCACCTCTATAACCCCGCTGTGAATCCCAGCACTCCCTTCCGATACGCAAACTGACTAGCAGTTCCTGTGTAT

AGACAAACGGAATCCTGGTGTACAGACAAACGGAATCCTGAGTTCCCAACGCATTCATTTATTTGAATATTTACACATTT

ACACACTGTACACGGTCATTCGATTTCATTGCCAACAGAAAGACTAATCGATGTCCCCTTTCAGTATGTGGACTGTGACA

GCAGGGTCTTCGCTCACTTCACTGTCCGTGTCATCCTCTGTACGCCCACACAGCATCGCCCGATAGTGAAAGCTGACACT

CAGCATGGAGAACCAAACAGCAGGGAGCAATGTGAGAGGCAGCCAACACAGGGAAACTTTTTTCTTCTCCCTTCAGACCC

CCTCCCGTCGAGACATTGTGATGGACTACTGGTACTTCGCCCTGATGTTCCCAGGTAGGAACGACCGTAAGGGTGAACCT

CTGAACGCTGTTCTGCATCAGGTCCCGTGTCACTTGATACATGCCGGAATCCGCGCCACTTAAGTTCTTCATAGTCACGC

AGTTCTCGGATCTGTTATACGACAGCGTCCCTTGATACGCCCCGTAGACCATCGGCTCCTTCAGCGCCTGGTAGTCCTGC

AGCACGAACTTGCGCACGGCGCCCGCATCCACCGCGGTCACTTCCCATTCTCTGATCTGAAAACTCTCGGTAGAACCGCA

CAGAGTCACAGCGTCCCGTTCGTTAGCCACGA<u>CCCGGG</u>ATACGTTCTCCATTTTCACCGTACCGTTCTCGGGAAGCCCCG
                                SmaI

ACACGGTGAAATATACAGTCTCGGGCTTGGAACCCACCGCGAATGATTGTGATAGCCAGCACCCGTTATTAGCTTTGATT

GCTTCGACATGCATTGAATTACAGGATGAATTTAGCCGCGCCCTGCTCATATAGCCCAGATCCAGCCCCTCTTTGATCGA

AGGAATCACGAAAGCCACTTTCTGCCATCTGTTACAGACCTTCCCCGGAGCGTGGTACCATAGCAGCAGCGTGAAATGAG

CCCATCTCCCCGTAGTCAGAGTCACCTCCTTACGGCCCCTCACGGCGGCACCGGAGACGGTGGCAGACAAGCAGAGGACG

GCGGCACACAGCAGGAGCGAGCCATGACTGCGGAGTCCGAGCCGAGCGGTGTGCTGCTCCATCCTCCGCTACCTTTTTAT

GCACCACCCACCTTTATTGTCGGTCACACATTAATTCGCCCCTCAGCAAACACGTGAGTAACGTATGCCGTTGTTCTGA

TCGGTCAGCACCGCGCCCGCGACGTTTGAACGAAGACGTACGGTGACTTCCGCATAGGGAGCTATAAGGAAGTCAGTTAG

GAAAAATCGATCCTCGACACACCCCACGGAAACGCTGACCTAGGCGAAACCTATCAGGTAAAACATTCACTATACGCACC

ACGCGTTGAATAAACAGTTAACCCATACGGGGTATATATTCTACCCCCACTGCAGTCAGCGATCAGGACGCGTCCACAGA

TABLE 11-continued

Nucleotide Sequence of the right hand end of fowl adenovirus serotype 8 (CFA40) genome GAGATCCGTGCGCGACCGCCTGTCCGGGCTCCTCTAGAATCAAGAATTCCATAACCATGCAGGTAAGAACTCCTTTCTCT
　　　　　　　　　　　　　　　　　　 XbaI

TCCTCCTATTTGATCCGACCCTTTTTTTACGCTACTCAACCGCAACCCGTTTCTTCCACCACAGTTACTGCTCCTTCTAT

GCCTTTGCCCTCTGATGGGCAGCGGAACACTAGCACCCCTCGTCTCGGTAGACAACTCCTACTCCGTGTTCGGATCCGGC

AAACCCCACTTTCTACCTCCGAATCCGCCACCACCGCCTACTCCGAAACCGCGGTTCCCGAAAACTCTTACCCCCATCC

GAGGCCACCACGCCCTGCGACGACTTGCTGGAAGAGGACTGCTGGTTCGCGGAGAGCAGCGCGGACTACGCACCCATACC

CTGGAACACCAAAGAGAATACGTCCGTGGTTATCCCGGCACAGGTAGCCGTCTCGCCATCGCAGTCCACTACTCCCCCTG

CGGTCATGCTCGGCATCGCACAGAAAGCCGTAAACCGCGGAGCCTCCAGCAAGGATCACACGTCCCATATCGCCACGGGC

GTTACCGTAGCCGCAATAGTCATACTCATTGCCCTCGTCATCATAGCCTTCCGTACAAAGGTTAAGGAACCGCGCCCAAC

CCGCTCCATCTACCTGGGCGTGCCTCCCCCTGACGTTAGACCTTACCGTATAATAGAGCAATAAAGATTTGGCCGCCACA

TCGCACAAGAATCTTTCCGTGTCCTGTGTCTGTCTCGGCGCCGTCCGCGGGAAAAGGTTAACGCGGAATCTATTTCCCTG

CGGATTTCCGTATCCGTCAGTTCCTGGGCGTCGCCGAAAATGCTCACGGAAGACACGCCCATGCGGGCGTGGCTAACCGA

TGATTCGAAAAACGATTCGCGAGCGCCCTCTGCCGGCGGCGGCGGGAATAGGGGTGTGGGGGAGTGTATTTTAAGTAG

ATATATATAGATGATG-

---

We claim:

1. A recombinant avian adenovirus vector expressing at least one heterologous nucleotide sequence wherein the at least one heterologous nucleotide sequence is inserted into a non-essential region at the right hand end of the genome of the avian adenovirus between map units 60 and 100 and wherein the avian adenovirus excludes chicken embryo lethal orphan virus.

2. The recombinant vector of claim 1 wherein said recombinant avian adenovirus is selected from the group consisting of serotypes 4, 8, 9 and 10.

3. The recombinant vector of claim 1, wherein at least one heterologous nucleotide sequence is expressed as an antigenic polypeptide.

4. The recombinant vector of claim 1 wherein at least one heterologous nucleotide sequence is expressed as an immunopotentiating molecule.

5. The recombinant vector of claim 3 wherein said heterologous nucleotide sequence encodes an antigenic determinant of infectious bursal disease virus which elicits an immune response to said virus when introduced in vivo.

6. The recombinant vector of claim 5 wherein said heterologous nucleotide sequence encodes an antigenic determinant of VP2 of infectious bursal disease virus which elicits an immune response to said virus when introduced in vivo.

7. The recombinant vector of claim 3 wherein said heterologous nucleotide sequence encodes an antigenic determinant of S1 of infectious bronchitis virus which elicits an immune response to said virus when introduced in vivo.

8. The recombinant vector of claim 3 wherein said heterologous nucleotide sequence encodes an antigenic determinant of hemagglutinin-neuraminidase of Newcastles Disease Virus which elicits an immune response to said virus when introduced in vivo.

9. The recombinant vector of claim 3 wherein said heterologous nucleotide sequence encodes an antigenic determinant of glycoprotein B of Marek's disease virus which elicits an immune response to said virus when introduced in vivo.

10. The recombinant vector of claim 4 wherein said heterologous nucleotide sequence encodes an antigenic determinant of chicken gamma interferon.

11. The recombinant vector of claim 4 wherein said heterologous nucleotide sequence encodes an antigenic determinant of chicken myelomonocytic growth factor.

12. The recombinant vector of claim 1 wherein said recombinant avian adenovirus comprises a live avian adenovirus having virion structural proteins unchanged from those in a native avian adenovirus from which said recombinant avian adenovirus is derived.

13. The recombinant vector of claim 12 wherein said recombinant avian adenovirus is selected from the group consisting of serotypes 4, 8, 9 and 10.

14. The recombinant vector of claims 12 wherein at least one heterologous nucleotide sequence is expressed as an antigenic polypeptide.

15. The recombinant vector of claims 12 wherein at least one heterologous nucleotide sequence is expressed as an immunopotentiating molecule.

16. The recombinant vector of claim 14 wherein said heterologous nucleotide sequence encodes an antigenic determinant of infectious bursal disease virus which elicits an immune response to said virus when introduced in vivo.

17. The recombinant vector of claim 14 wherein said heterologous nucleotide sequence encodes an antigenic determinant of VP2 of infectious bursal disease virus which elicits an immune response to said virus when introduced in vivo.

18. The recombinant vector of claim 14 wherein said heterologous nucleotide sequence encodes an antigenic determinant of S1 of infectious bronchitis virus which elicits an immune response to said virus when introduced in vivo.

19. The recombinant vector of claim 14 wherein said heterologous nucleotide sequence encodes an antigenic determinant of hemagglutinin-neuraminidase of Newcastles Disease Virus which elicits an immune response to said virus when introduced in vivo.

20. The recombinant vector of claim 14 wherein said heterologous nucleotide sequence encodes an antigenic determinant of glycoprotein B of Marek's disease virus which elicits an immune response to said virus when introduced in vivo.

21. The recombinant vector of claim 15 wherein said heterologous nucleotide sequence encodes an antigenic determinant of chicken gamma interferon which elicits an immune response to said virus when introduced in vivo.

22. The recombinant vector of claim 15 wherein said heterologous nucleotide sequence encodes an antigenic determinant of chicken myelomonocytic growth factor which elicits an immune response to said virus when introduced in vivo.

23. A method for producing a recombinant avian adenovirus vector for use in an immunogenic composition comprising the step of:
inserting into a non-essential region of an avian adenovirus genome at the right hand end of the genome of the avian adenovirus between map units 60 and 100, at least one heterologous nucleotide sequence as claimed in any one of claims 5 to 11 which is suitable for eliciting an immune response, the heterologous sequence in association with an effective promoter sequence with the exception that the avian adenovirus is not chicken embryo lethal orphan virus.

24. The method of claim 23 wherein prior to insertion of said heterologous nucleotide sequence, a restriction enzyme site is insert ed into said nonessential region of the genome.

25. A method of protecting birds against disease comprising the step of:
administering to said birds a first recombinant avian adenovirus vector of claim 1 incorporating and expressing at least one heterologous nucleotide sequence encoding an antigenic determinant of said disease against which protection is desired.

26. A method of claim 25 further comprising a step of:
administering a second recombinant avian adenovirus vector to said birds, wherein the second recombinant avian adenovirus vector incorporates and expresses at least one heterologous nucleotide sequence inserted into a non-essential region at the right hand end of the genome of an avian adenovirus between map units 60 and 100 and wherein the at least one heterologous nucleotide sequence incorporated into the second recombinant avian adenovirus vector is different from the at least one heterologous nucleotide sequence incorporated into the first recombinant avian adenovirus vector.

27. An immunogenic composition comprising at least one recombinant avian adenovirus vector of claim 1 and suitable carriers, excipients or both.

28. An immunogenic composition of claim 27 wherein said carriers and/or excipients are selected such that said immunogenic composition is deliverable in the form of an aerosol spray.

29. The recombinant vector of claim 1 wherein the avian adenovirus is non-pathogenic.

30. The recombinant vector of claim 1 wherein the heterologous nucleotide sequence encodes an antigenic determinant which elicits an immune response in a bird when introduced in vivo.

31. The recombinant vector of claim 30 wherein antigenic determinant is a polypeptide.

32. The recombinant vector of claim 30 wherein antigenic determinant is an antigenic determinant of infectious bursal disease virus.

33. The recombinant vector of claim 30 wherein the antigenic determinant is an antigenic determinant of infectious bronchitis virus.

34. The recombinant vector of claim 30 wherein antigenic determinant is an antigenic determinant of Newcastle's disease virus.

35. The recombinant vector of claim 30 wherein antigenic determinant is an antigenic determinant of Marek's disease virus.

36. The recombinant vector of claim 30 wherein the avian adenovirus is a recombinant fowl adenovirus.

37. The recombinant vector of claim 1 wherein at least one heterologous nucleotide sequence is expressed as a cytokine.

38. The method of claim 26 wherein said second avian adenovirus vector comprises a serotype different from that of said first avian adenovirus vector.

39. The recombinant vector of claim 1 wherein the at least one heterologous nucleotide sequence is inserted into a non-essential region at the right hand end of the genome of the avian adenovirus between map units 70 and 100.

40. The recombinant vector of claim 1 wherein the at least one heterologous nucleotide sequence is inserted into a non-essential region at the right hand end of the genome of the avian adenovirus between map units 92 and 100.

41. The method of claim 23 wherein the at least one heterologous nucleotide sequence is inserted at the right hand end of the genome of the avian adenovirus between map units 70 and 100.

* * * * *

UNITED STATES PATENT AND TRADEMARK OFFICE
Certificate

Patent No. 6,296,852 B1

Patented: October 2, 2001

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Michael A. Johnson, Thornbury, Australia; Christopher T. Prideaux, Coburg, Australia; Richard J. McCoy, Highton, Australia; John W. Lowenthal, Belmont, Australia; Michael Sheppard, Eltham Australia; Wendy Werner, New London, CT; and Katrina Erny, Riehen, Switzerland.

Signed and Sealed this Twenty-seventh Day of May 2003.

JAMES HOUSEL
*Supervisory Patent Examiner*
Art Unit 1648

SEQUENCE LISTING

<160> NUMBER OF SEQ ID NOS: 8

<210> SEQ ID NO 1
<211> LENGTH: 195
<212> TYPE: DNA
<213> ORGANISM: fowl adenovirus

<400> SEQUENCE: 1
tgctcgtgac cagcccaaaa caaagcatgc tatttgggtg gcataacgtt tgttttcgac      60
ttgtttgtcc aggctttcta ggtggagtac ggtgagcgcc tccggtggcg cgtcgaggaa     120
tcgaacgggc ttgaatgcgg tctcggtggc tcgcgagtgg gcggggtttg tttctgccgg     180
cggtcgcccg tcatc                                                      195

<210> SEQ ID NO 2
<211> LENGTH: 31
<212> TYPE: DNA
<213> ORGANISM: fowl adenovirus

<400> SEQUENCE: 2
tatataaagg ccgcaggtga gcgcttcttc c                                     31

<210> SEQ ID NO 3
<211> LENGTH: 40
<212> TYPE: DNA
<213> ORGANISM: fowl adenovirus

<400> SEQUENCE: 3
agctcctgat cgacttcgga gaggtctgcc tcctcggcgg                            40

<210> SEQ ID NO 4
<211> LENGTH: 131
<212> TYPE: DNA

<213> ORGANISM: fowl adenovirus

<400> SEQUENCE: 4

```
ggatcctgtc cgagccatcc cgcttgagga tcgttttcga ccgcgcggac gagccgctga    60
gtgtctagct cgccaaaggc ttcgacgaag aggttgagcc aatcgtcttc agcgaacact   120
tccgatccag g                                                        131
```

<210> SEQ ID NO 5
<211> LENGTH: 169
<212> TYPE: DNA
<213> ORGANISM: fowl adenovirus

<400> SEQUENCE: 5

```
agctcctgat cgacttcgga gaggtctgcc tcctcggcgg atcctgtccg agccatcccg    60
cttgaggatc gttttcgacc gcgcggacga gccgctgagt gtctagctcg ccaaaggctt   120
cgacgaagag gttgagccaa tcgtcttcag cgaacacttc cgatccagg               169
```

<210> SEQ ID NO 6
<211> LENGTH: 8442
<212> TYPE: DNA
<213> ORGANISM: fowl adenovirus

<400> SEQUENCE: 6

```
gaattctccg cggtcgtacc atctcagaac agccaattca tcgctcaaat cgtctgtctt    60
cctgggagga ccctcctctc tccactccgc taccgagcag ggttcggagc cgttaaaggc   120
acacttccaa cgggaaccat cttcaaaagt tgatccggga ggaagaccgc acaaggcgat   180
caaaacaaac taaaaacac gcacgataag gtcacatgca atcgaccta acctattctc     240
ccaaaatgat actcaccaca atcacgcaat gcatagagta cggctcagag gctccttctc   300
gagtggagta ctagccgggc gaataaactc cgatccgaac atccgccata taaacacagc   360
tttcgtaaaa tattaacaga cactaacttc ctcattgacc cgcttaattg ccgtgtcagc   420
aggtggctga caatgagtca tcgatgagtc atcgctaagt caacaatgga actttccact   480
tgctaacaaa gcgaaaccaa aagttaatca ttaacgccac acccatgatg agtcatcgcc   540
agtaaacctt aaaaggacgg ctccagcccg cagcgaaaag caaccttact tccaacacga   600
gggctctgcg gaaccatggc cgaagagtgg ctcgactttt caccccctcca cttcgccgaa   660
tccagaagga gaaggtgagg acatgtccct cgagaccgag tgccatgccc ctcttcacta   720
tatttaccat gctgtctttt gatgacctcc tggcggctgc cggtcccccc ggaatactct   780
ccggaagaga acctgtaaac tccgtcgctc gacaccatac aggtaggaga catcatggcc   840
caactcgcgt attccgatag agggacctcc gaccaaccct tccgactctt cctccagttg   900
ggattcagta ctttttctgcg gtgtcaactc gtatgactta aactatacca ttgtctttttc   960
ccgactccga gagtcttggc aatcgcacgg cgcatacttg aaaaccgtac cttcgctcga  1020
gtgcgtgcaa aacgacggga aattccagga agcatactgc tcactggtga aatgcacgc   1080
cgtttccgaa gatgccactg agcatctcaa tgaactctta ctagacgaaa cccactacca  1140
acattgcgaa cccctcaatg acatgttgga cttgggattc cggtggctca atgacctaaa  1200
aggaggaatg gagtggtgca tggacactgc cctggatcgc gcatcaaaag tcatgcctct  1260
gactgactat caaccacaat aaataaattt tacattaaaa actttctgag taagattttt  1320
cgaacctgaa aaattctaag tgcggttaat cattaatcaa gttaaatatt aaactctagt   1380
taattattaa actctagtta aatattaaac gctagttaaa tattaagctg aagttaatga  1440
```

-continued

```
ttcatccgag ttaatggata accttgagtc aatgattaac tctggttaat atgtaactcg    1500
gctaatgatt aacatgggtt aaccattaac atggtttaac cattaactat agttaataaa    1560
taactctaag ttaataagta gctagtgacc gtacgattga cgtcacggtg accgtcggtg    1620
ttgccatgga gatgtaacca tggtgatgtt aaacattaaa ctgctgacac cagtggaatt    1680
ttccatgtta accattaaca tggaccttgt cctgtttgtt tattcaccat ggcaacatac    1740
catatatgga catccgactc cgcctccccc gttatacatt aacgatggcg tgataggcgg    1800
agctctctcc cattggctct caatgatgtc atgtagttac acattagccc gttcaaccta    1860
tataggtaga ccaggtaggc aggttcagac agacagaccg gggaccagca gactgaacgg    1920
agctctccac taaaccggta ggcctctata ttgaatcgat gaataaatac cgaatcactc    1980
aatattatga ttttccattg aaattaatgg tgattttctt caatcaaact cccaccccccc   2040 ttggcacccc cctgtacacc ccctgtaca ggcgaccacc cctatgatc accccctgt      2100 acagccgacc accccccatg accaccccc tgtaccatta cagccaatgg gatcccatcc    2160
attgacatca catgatcccc gctggcccta tgaggtggct accatatcct tcaccctatt    2220
ggatcccatg ccgaggggcg gaaaagatgg gaggcgcccg tacctcgaca accaattggc    2280
tgaggccctt cagttcagtt ccgccctcac ttccgaccaa ttcaatgcat tggagttcac    2340
cacgtgggtt gtgaaggggc ggagactcct ccataaggga aagcagtacc gcctttacaa    2400
cagggcggcc gggatatgca gtatccacca atggagagaa gtgaggccca gctgaccatg    2460
gaggccgtag ccaatgggct gtgggatctg ccggatgaaa tactcgggag ccccctactg    2520
cacaatactg gtatacacac ctggggctgg gggtccccg tcactaccga gatcagcctg     2580
aggatggtgg taaagaccct ccgtgtcaat actccattcc accgccaggg ggagatgcct    2640
ataccggtat ccaaggaggt ccatgtgaaa gccccccaac attttgaaga catgctccag    2700
ggggtcctga cgaccaccga tctaaaaaag catattccta gacccatctt ttcccgattt    2760
tttaacgaaa aaccctcggt ttgggcctat aagactttca atattcggc cggtgaagaa     2820 aaatggcgag tggtggtccc taccgagggt ccctatgggg gtcctaagaa ccctgtttct    2880
ttgcaaaacc tcgcgaaaag ggtgtgttga aaattgtcta aaaatgaaaa gggcggggct    2940
acggttcatg ccatattaat aaaccaatca gaaaacagaa atacgactcc tcctctttgt    3000
gggcggtcct ggggaacacc aatagaaata gagactccgc ctatgaggcg gagacttagt    3060
tactgaataa cttttcggac ttagaaaaat tttcacctgc ttaatcattt accaatgggc    3120
ctacgtcact atgctccgcc tttaactccg cctatagctc cacctctctc tccgccccga    3180
tggactttgg actttagatc acatgactgc tacgtcacgg agggaggagc ttcggactta    3240 gaaattttc gctctatcaa tcattaactt gacgatggac tttgaacccc acgtaagcga     3300
cggggaggag ctaacgttaa tcttcaactc ggactttgcc cggaagcgga gcttcggact    3360
taaaaaattt tccactctat caatcattaa ctgggcaacg gactttggca ctgacgtgcg    3420
caaagaggag gttctaaagt taaactttaa ctcgaacttt gtccggaggc ggagctccgg    3480
acttaaaaaa attttttcacc gctataatca ttatccaact gaatcacatg acacaaagga    3540
agagactgta atcaaattta attattaaca actcagtcaa catttacatc atcagcggta    3600
caaagtccag tacatacacg ccacgcccca agacattgaa atgcttcctc cgtcacgccc    3660
cagcgcccca tgcggtactg ctcgggacac cactgattat catagagctt caaccacacc    3720
tggcacgaag agccggtatc tctataaaaa accaaatgca gggccgtcgc atatcactcc    3780
```

```
gacacttctc caactttccc ttagtctgat cggaacaatg gatacaaatt aacaaagttg      3840
catgacattc gcacacggaa aactcttgca acccgaacat gtacttcaga ggactgcatt      3900
cgggactgta cttctcaaca agtttagtcc atatgaactt caatccgcga tgaacatatc      3960
tgaaaacctc aggcctctga caccattccg gaactgccgc tccgaacaca aggtacattg      4020
tcatctgaaa tttaagccat ttattcatac acgcactcgt aaatacatcc ctctctactg      4080
ccaaccgctt ctgatgttat gcaatattca cccaagcggt actcttgcgc gtatccctcg      4140
ttacgcaaaa ggcatacacc cttaatccac ttctcactgt catatggata tttcccaaaa      4200
aacaaacact taacagccaa accaaccccc tccagatacg cgcttccaaa atccgaacca      4260
aggcaaaaaa caatcgatac aaaatcctcc atcttgcaaa gcatagagat aaaagaaacc      4320
cgttactagt ccaggaaaca ctttcctaa atccaatttc tcccaagcat taattatatc      4380
acacgcgcga aaatcgtgaa acatagccag gttcaattcc cataagggcg ccaacataag      4440
taacccaaca ttaagtaacc caacattacc caccgcacac tgggctgtca aatgagcgct      4500
ctgcagtcct ccaaactctg tagtacttat acagtctacc tctttaatca ttaaccatag      4560
acgtcatgga aaatttccaa ccccacccag aatgaatcac cggtcaaagg tcacttcctc      4620
attacctaga taaggatcac aaagtacttc ctcattacct agataaggta tcacaaggta      4680
catgagtcac ccataatgat actgaatcag cggtttcggt cacgtcagta tcagacaatc      4740
attaaccaga gattcctata aactttccgc agactcgcac cacggtattc catccgaaga      4800
ctgatccagt ctgaagacaa tcttctcttc ggtgaacagt cctgaggaaa aacaccatgc      4860
gggtaagcat cattcatcca ttataccct ttttactctt tcacctaacc tcgctaacat      4920
agatctccta cctctcggtc cacagctgtt aactccatac agaacaaacc cacggtccct      4980
accaaaggac ccatggccaa cttcacctct gttcgccatg aagtcacat caattacttt      5040 tggtatgggc aacacggaat ggcaccctcg aaaatccacg gtcctctcca tgatgatgac      5100
atgatatact ggagactccg tgaccgtggg ttcctgagag gaggcagaga aaagaacctg      5160
atcctactcg tccatggatg gcacggcctc caccgcacct ttgatatctt cttcagcttc      5220
ctccgcttcc accagaagat gacaccagac gtaggtgtgc tcttagtaga ttgggggta      5280 caaggtgctg acaaactaat tctaggagat gctgcctacc acgccgtcac catcaatatt      5340
gatggcctac tcaagaacct gaaccgcacc aacttacact gcataggaca ctccttgggg      5400
gctcatgcat gcggtgctat ttgtcgaaga ttcaaccagc tccaaaagaa gaaatgcact      5460
agaattgttg gactcgaccc agcagggcct ctcttcaaaa ccaactctcc ctatccttac      5520
ctcaccaaag cccgtctgtc taagaagat gctgactatg tagctctctt tatgacgaac      5580
cgacggatga tgggactcca cgaattggaa ggagatgagt acattacccc ctatatagac      5640
ggaacctatc tgaaccattg tcctttcgtc ggtaaatgga caggcaccat cacggcagaa      5700
aactaccaag gaagaaaggt cactgaatac atcgatttag gaacggtggc caaatcggga      5760
ataatcccac acaccatgga atgcatgctc acacctcatg gcccctgttc ttttcatggt      5820
gtccctagac acccgccaag gcctacctgc attccggtat gttgacaacc ctcccaaaga      5880
tgaaggtgcc atgcatacgg tttggaatgg gtataccata gggaaagact acctatgacc      5940
agcctatttc aaacacgaaa ctatctggct tagtacgctc acgacagatg gaaaccagct      6000
agctagcacc cttcgaattc caacacgaag attccataga tccgtctttc atggcaatgg      6060
caattagcga caaaggttgc atctggtccg gctcccatct gagctaccac tacagtatca      6120
tcccttacgg aaacaaatac gatctggtaa catccttcag tgcactctcc cctggaatgg      6180
```

```
tagacgcaca cttcctcgaa gtctacatga actacgaaca ctgccccgtc tatctagccc      6240
gatttctgat tcccaaaccg taccaactga agttacctag acccaccaca gccggtctct      6300
cttccgaaat cttaagatgc aataaacaaa ccacatatac ctggaactgc tacagaacat      6360
ggcagcaagc tgtcctaccc gtgtaccgcc agcaactcga tcttacgggt gacgaaaat       6420 acaacatcca ggtccctccc aaacatggat gcctgaaaga caatccaac tttaccgata       6480 tgttccgtac atacatgggt gaatatgaag tcttgtctga gcagactgtc atagtaacca      6540
gcttgccgtc accgttcgaa ctcatccgta ttgctctgag agatcctgcc tcacccgcca      6600
ttcaaaacat catgacctat tgggacatgt gcgtacccgt agctagcact tgtagcttca      6660
aagtaaatcg agcaacgaga actctcagca taacctgccc cgaaccgaat acctactgga      6720
tctccttctt ttaccaatgg gaagaagtct tgctcaagat taatgtccat cctaaaccca      6780
ctaccactac caccactacc actacaacca ctactcccac taccactaca accactactc      6840
ccactaccac taaccactac aaccactact cccactaccac ctactcccac tactcccac      6900 ctaccactac aaccactaca accactactc ccactaccac tacaaccact actcccacta      6960
cgacctccac cgaatcaatc acagaaccga gctccgcttg tgatgaagaa gaagatgaag      7020
attgttggtt cgaaaatatc gcgatcagaa tgaagttcct caaaaaggta caactcccgt      7080
tcaaagtagc gaacaatgaa atgtcagaac caactactgc tgctactact ccttccagcc      7140
ctgccgccat agaggaagaa agcaacagca gagcatctac accacccct cttcaactca       7200 ccgtatcccc aggtactaac cccctcttc aagaattcct caaagcggaa ccatcatcta       7260
aagattccct ccacaaggac caagacgcca cggtcaccat tcctgccacc attggactct      7320
tagccctagt ctgtctcagt gtcatcgttg ccgtattcat tgcccttaga aggagaggga      7380
gaggtcaagg ccaaccttat tgttgttcct ggaagagcaa taatactgta taccaggaaa      7440
ctactgaaat gttgtaaaat ttataacgct ataaaagtgt ctgactacaa taaagataag      7500
agcataatca actcgggtgt ccgcccattc ctttctctat atattctgtc acgaacagat      7560
ttcagacaga aggcgacatg ggaggcgaga agagctccgt sacaaagcta gacaggttcc      7620
cctactgggt accctagaag aaatagatag gtatgctaag ctaatcgcgg aacagtggcc      7680
ccatcgggtc cggcaaacac tttctagtta taggagatct ggaaggtacc ttacatgcgg      7740
ggcaacattt aaaggaatac tgcgaagtgc tatatctacc ttccccaaaa agaatgaccg      7800
tcattggcat agtggacaac gtcatctcat tcgcggatgg attgcaagta gtcattttgg      7860
tggcggaaga taaaaccgtc tatggctacg aagaagacac tctccataaa ttagcatcca      7920
ccataccaga attctttcgt atcggaatgc agaactttgg aaccgaagta tttcactgcg      7980
gttcccacat ccccccattg gtaagtgcag atcccacacc ctctcattac ttacctgata      8040
gatactaaca cactatattc cagtccgagg aggagcgtca gcgtgatccc gagataaggc      8100
ggctccgaga agaagctcga aacttcatat cagccggcga agaaaaaaca gactaaccaa      8160
ccgcaatccg atccgaacat agccacgcaa tggtgtgcgg atccacttaa aatagattac      8220
gcgtattccc agaaataaac tgattgaaat gagaggcaag agctgtgtca ttatttcgcg      8280
ttcgttcgca aatacggaag tccatcacgg atatccgtaa tcgtcatttg ggtggagacc      8340
atgagtcatc gatgactcac ttaaacggtt tcggtttcgg ctatcacgac gtgcgcgcgg      8400
cggttgtaag tgtgtcaaaa gacgcggtta tataagatga tg                        8442

<210> SEQ ID NO 7
```

```
<211> LENGTH: 8520
<212> TYPE: DNA
<213> ORGANISM: fowl adenovirus

<400> SEQUENCE: 7
ggatccacag agaaccttcc gccaactcgg tatacgctat ctcggtggtt acatcgtatt      60
tcccatatct aaagtctgc  acactatagc ctcccatata tacgctgcta tcatgtgaag    120
caactactat aatcataata gaagaaacaa agtccttctt aaaatttggg gaatacgaca    180
tttccgtcat atactttatg ctgtaatggt tgaagtaact gtcatatcta taatcacgac    240
taagtgtata cccattccaa gtactcctta ccggtcctac cctcgaccct tcctgtaata    300
catggaacac aggcaaacct gtctttacat ccagggtttt caaaaacttt ggaacaatca    360
ttcgatgata gcatccactt aaactaaacg tattacccca ggaaaattcc tcacatactg    420
tcgctcccca acattttct  ccgcatactc ttccggacca tccaccgtgt ataccacagc    480
ttctaccgcc cttatcttcc accattaaat cttccgaagc cgtgtaccca ccagtgatcc    540
acgaatactg agtctttaga cgaccacat  aatccgcatc caacttatct aatccaccgc    600
ttacaaatgt cggttctagc ccgactattc tgatacaccg atggcccttg ctcatttgtg    660
aatactgtct acatatcgtc gagcaagcat gagctcctgc cgagtgacct atacagtgca    720
attttttagc gtcggggata tctaccagaa acttcctaaa atccgcatgt aaaccatccg    780
tatcatagta caaccgatag tccaccaaca caacacctac ggcgggagtc atcttctgat    840
gaaatcgcaa caccttccta aaatcgtcat atcccagata ccatcctggt ataagcagca    900
ctatgtctga tttcccggcg aaggcattgt gcattttatg gtatacacca tactcgtatc    960
tcgcatcgtg gaacttcggt acaccaccat gcgatccata ccacgtgatt ctcgaaggaa   1020
gtctgttcgg atttccggcg cttttcggag cttccagttt agtagccgga ggcattgcca   1080
cacaggacca attgaccaaa tcatggcaac cttctgattt cgtacccgaa aatgcggagg   1140
ccccgaggag caccccgaat aactgaaaca gaacgcaaaa tttagaccgg taccctccca   1200
tacgattatc acgtcccaaa gccaaatatc acggtactca ccagcgcaaa aatcttcatg   1260
aagatctggg gcaagagccg cacaacagtc cacctgaatc tgagacagct taccggcgac   1320
tgtaccaaac cggtgtgcca ccgccgaatt tattctctca atctattaat gtttaactaa   1380
acaaacttgc tgacacttga taaatattta ctgacctaga caattccgag aacttcctta   1440
ttaccgtgac tatgcagtat caagataaac ccttccaaag ttcgactgag tacacggtgt   1500
acttcctgtc ataaaatatc acttctaaat atagtcctag gtagaaacta taaatggtaa   1560
gagacaaacac actgattctt agaaaaacct cacagaacaa gatgaacctc acattatcct   1620
gactcttcct tacgaactga ataaccggt  aagtcataaa aatgattttc cttttgacat   1680
tgcgtacgcg gaagcaaact agaaaaatcg aacttggaat tttccaagtc gagttaacta   1740
ttaacttgat gacgtcaatt ggattaatca ttaactcgaa ttagttaatg attaactaga   1800
tctggttaat gattaactag tctcagttaa tgattaacta acctggttaa tgattaacta   1860
acctggttaa tgattaacta atagttaaac attaactagt agttacttat taacttatga   1920
ctcatggatt aattattaac tagtgacgtc actagttaat cattaagctt tctatgcgta   1980
tgcatgagag attcatgcgt atgaatgaga gtctcatcca tattcatgaa cctcatccat   2040
attcatgagc ctctcatgca tatgcatgtt tttacatgca tatgcatgga cctcattcat   2100
attcatcaat tcgttaatgt ataacgctat gactcactgt atatgtttac gttgcctagc   2160
aacgttaatg atttacctgc tgacgtggca gctccgcctc ccggtaaatc atttacctgg   2220
```

```
actttgttct ttatgtttat tcaccatggc aacgctacca tatatggaca tccgactccg    2280
cctccccagt tatacattaa cgatggcgtg ataggcggag ctctctccca ttggctctta    2340
atgacgtagt ccgggttaac cataagccag aaccgcctat ataggtagag caggtagacc    2400
cggaacacca ttcccatacg gacctccata gagtgcggac ctctacgggc tctccatacc    2460
ggtaaatatt ttattccatt taatccaatc aaataaatca ataatcaact caatgctgtg    2520
attctgcctc aaattcaatg gtgattttct ttaataaaaa gcccaccccc cttggcaccc    2580
ccctgtacac ccccctgtac aggcgaccac cccctatgga cacccccctg tacaggcgac    2640
caccccctat ggacaccccc ctgtacaggc gaccacccc tatggacacc ccctgtaca    2700 ggcgaccacc ccctatggac accccctgt acaggcgacc accccctatg gacacccccc    2760
tgtacacccc cctgtacatt ttctcccata ggctacaatg gaacactgcc cctagtgtc    2820 tcccgctcca tgggacccct atgaggtggg caccatctca tttgccgcaa tggagctcat    2880
ccacgagggg gcgccattga agctagggga ccgcatagag agcctggcca atgggtgct    2940 ttggaatccg gatatcccg cccaactctt caactgcatt tctattcgct catggggatc    3000
acatgggaag cgcgtcatat tcaaaggcca cacccaccgg atgttccacg cccagcttag    3060
gatccgtagc accgccccg ttactaggaa acaggccgga agcctactcc tcagcctatc    3120
acagaggctc ctgtgtttcc ccgcccgcta taatacccac ccctcgtga tgcaattggg    3180 ggtggagtct aatgccatgg gacttcctat atattccaag agggccctcg agatggcgct    3240
caagagcatg cgggtgcgca ttgcgcctaa cagccaccag gtggcgccac ctgaaatagg    3300
aaagacctgt acggtgaagc ccctcaaaga agtggagacc ctccagcagg gggtcttcag    3360
taccaccgat ctaaaaagag cacttccaga aatggacttt tcgccgactt ttttacgaaa    3420
ttccctatat ttgtggctgg aagattggca ctgctccaga aggggcggag aaatggatgg    3480
ttacgctcca ccccgaatcc agagccccgc ccaccgaagg acggaaggac ccgcccactc    3540
tccaagacct cgcccggctg ggcgtggtcg aaaactgcct caagatgagg aggcggggca    3600
taagccctag gcaccacccc tactttcaat aaaccaatca gaacagagca cttgactcct    3660
cctatttgtg ggcggggcta tgggtacggt atagagcgcc ccctggcggc cgttggccgc    3720
cactgcaccc gcgccggact tagtctctgg cgcgggccgg tcaatcatta acccggcgcc    3780
cagcacgggc gccccctgcc ggccggagac agacactgcg tgtctgcgga gctcccctg    3840 gcggccgagg gccgccactg cacccgcgcc ggacttagtc tctggcgcgg gccggtcaat    3900
cattaacccg gcgcccagca cgggcgcccc ctgccggccg gagacagaca ctgcgtgtct    3960
gcggagctcc ccctggcggc cgaggccgc cactgcaccc gcgccggact tagtctctga    4020
caccgcattt actttcaaca cctttttta tttcagcaca ccgaaatctc gtccgtgtaa    4080
accttgtccc caaacctcag tcccgtacat cgaacccatc cacatatatc tcgcacagct    4140
ccagtgctta caagatattt ccctactgga taattaggat cttgacacca cttattcaaa    4200
tacatccgga accactgtcc gtctggaact tggcttctgt agaactcctc acgaaagtag    4260
cgcttcattg ctctagaaca cttatacaaa tgtttatctc tcaggtcgaa catcgtgagg    4320
caaatcaaca gcgtcaaatg acaagcacaa gaaccgcccg gctgaagccc gacgcagtaa    4380
cccataggat gtccgacacc gatgttagct tcttcgtggt acggatacca cagctccttg    4440
atgtcttgaa ctagcttcca gaagatggca tcgtgcatac accacggagg tacggcaaca    4500
ccaaacacca cgtacaaagg catctcccga cactctgcaa ttacaactag catcagaaat    4560
```

-continued

```
acatccagcc gctatttgaa aaaaacaaca ggatctcacc caaaagaaa aagtacttac      4620
cccgaaacca ccaggaaatc ccccttacgt gataatccgg atctcgctga cgctcaaaga     4680
agccgcctta ataccgctc cttatctctc ttcgattacc tcagttacgc ccatttctta      4740
tcaggtaaga tacgcaggta agatacgccc ttccacatca gcacggaatg tgctgaccag     4800
cttaccgcgc ccgttttaa tatccgttaa ttagtaactt aggtgaatca ccaaaccacc      4860
tgccggcata tatctacacc cttgatacgg cggcatccat tgaagtcgag cgccaccatg    4920
gagtcaacta ccgtatcctc gattctgctc ctatccttct tcgtatcttc catcgaatcc    4980
tatccgctcc tgcataactt cacggcgctc acgggatccg tgcttactct tccctacaaa    5040
ggacatgacc gacccttta attcgaatgg cggctgacag atcagaccaa agtagcaatc     5100
tcggatccta gcaccggcat caactacccg tcgggtccac tcaaaggaag agtacatcta    5160
aacggcagcg ccctcatcgt tacatcccta cgacttagtg acgccggtac ctatacaatc    5220
ctctcagagg acaacacagg aactgaaatc ggatactcct attacgtcga agtcagaggt    5280
atagaacttt cccctccttt ttctacatga tatcccgttc cctctttttt cttaccccta    5340
gcttattctt cctagaaccg atgcaagctc ccaccctcta tacggatcgc tacaatgact    5400
catctgccat acgcctcaca tgccaagctt ccaacaatct ccaccgtaat atcacatacc    5460
actggaaaac agatttaata cagccaacta actcgactcg atctatcacc ttaaacatcg    5520
aagactatat atccgttacc tgcacagtca ctgatggagt cagcaaaaac agcatcacga    5580
ttatggttcc gttgagaggt agtattcggt ttcccgttat ctccctatac tacgtaatca    5640
tgcccaccct tttaacccgt atctttacaa cagatcctc tccacctacg ccttacggtt     5700
tgcatcccac tatcattttc ctgagtgtcc tctgcatgat cctcatcacc gcaattaccg    5760
tctactttgt gaagaagcat tgctgcgata agcaatataa aataacttgc attaacccttt   5820
accgagaatg cttcggtggc gccggtctcg tttaatctcg tttaaataaa aaccactata    5880
atccccgctt cctataatct ctacttccta tgattaaatg ggtaattaaa tgatgggtaa    5940
ttaagtggtg tcaatgatca aataatgatt cggaaacgat ttcggaaaaa atgattttag    6000
gaatcaatga tcattatcaa aaataaatga tttattata agacgtgttt ttgatgattg     6060
atacgattag taaatcacat gattagaaac acatgattag aaaacacagtt taatcatcaa    6120
tcgaaatcac cgcgcaagat atggacagtc acgttctcct ctgatgtcct atccatagat    6180
tcgctgtccg tagaatcaga ggcgcagagc atccgccgaa accagaaagt tatcgctacc    6240
atcagcaata acaacataat taacgcgatc ggcagccaca ctggaaactc gccggtctga    6300
ttggatacca gtcctccgcc ggtcttataa gtggtctcct cgatcttctg atcctcctga    6360
gtcaaaccag gaattaccac tacgtaaaat ccggtctttg aatcctgttg taagtctagc    6420
gtattagtat acagtcccga atcggcaggt gttacgtctc taatagtaac gcaattggat    6480
gtggcattgt aatgcgtgcg gctcttatag ttagcataca ctatggggtt acccagagct    6540
ttataaagct gtaatacgaa cacggtagac gcgtgctcgt tagaggactg aaactcccac    6600
tccgttatag aagcggagct agcatccttc ccacacatgc gtaactctcc accttccaaa    6660
actaatatac ggctcatgtt atgcacctca accgtcgcat tgcccgtaat atccttcacg    6720
gtatactgta tggcatacgg tttcccaccg acaaaggaac cgtaagtcaa ccagcacccg    6780
ttattagcct tcagcttact caggtaaata gtattgcaac cactatctac cctcgttcta    6840
cccatgtacc cgctttcaag tccaggttct ttaaccctcg gaatcacaaa tgccgccctc    6900
tccatcttat tgcaattggg ggacggggaa tgataccaga ggatcatagt atggtccctg    6960
```

-continued

```
cactctcctg tccgtagagc cagctccggg tcccggggag cgccaaagca gagtccgagg      7020
acagcagcca gcagcagggc aacggacttc atgatgaatg cgggaaccag ccagcagcag      7080
caggtagaag gtgcgagtac tcgaggcagg cgggaataac accgcacgct ttccaccccg      7140
cttaaataca caacccacac cggtcatggt caaacattac ctagcctact cagcacggaa      7200
aagtactcac ccttaacaca gttcgactta tcaggtacac acccgtaacc ttcgcacccc      7260
aaagcgcaca gtcagcacca taaggaagtc gtaaagttac cctttgattg cattgtcatc      7320
ataaaaaacg ctgagcaaac ggaaacgccc caagtacaaa tctctcttcc gccacgccct      7380
cgttaatcaa taactagtcg ccgatacata tataccccct ccgttccatc acacctacac      7440
taccttctct ccgcacaggc aacatctcaa tccttactct tccgaatcca cttcgccgcc      7500
ttcgacatga atccggtaag tatcaacttt tttctaagct tatgcttctg cacctctga      7560 tcttaatacc gcacccctt tttctcaaaa aaggtttcgt gcttaacgct tcttctatgc      7620
gtcatcatcc cgagagccga tccgcttcca atcaccccg cctctaaacc cgctaccgac      7680
tccgcccgga ccggcgcctc cgtcatcacg acccacttac ccgcatctcc gagcgccacc      7740
ccgtgcgacg aaatcttgag cgaggactgt tggttcgaaa atgccagcgg tgattaccaa      7800
cccctaccct gggaaccgaa agaggaaacg gtttcagatc aaaaccctct caccgcaacc      7860
gaccccatcg gtgaccgaat ccccgctatc atccagtccc agtccgcgc ttctaaccgt      7920 ccgaccagta aggaacacac ttctactatc gcatccatct cgaccgtagt cggcatcgcg      7980
gtcctcgtca tcctgaccct cgtagcctac tttaccaagt accccaaacc gagaccgccc      8040
agatccatct acataggagt agctccaccc gatatggaac tcaaggaaat ataattccag      8100
ccccaccctt aaccctacct ttccatgagt cagtattttc aataaagtta tattgcagta      8160
ttaattccgt tgtttccgcg ttctttctct cgcgcggaca aagtccgttc gaccaggaag      8220
tccggtatac gtcattccgc ggtgtcatga tgacgcgcat aactcacgac tgccatctgc      8280
cggacaaacg cggtactaca cttaacacat aaacacccgc cttttttcga ttcccaccat      8340
aatcaggctt tggtaaaaat tcgcagattc taaaatccgt attcctgcgc ccgcgataat      8400
agatcacgcc cacgacacgc cctagcgctc ttatcacacg gtctctgctg ccatctagcg      8460
ggcgggagcg gtagtgcgag gtgacagcag cgtcattcat gtaggtatat atagatgatg      8520
```

<210> SEQ ID NO 8
<211> LENGTH: 19056
<212> TYPE: DNA
<213> ORGANISM: fowl adenovirus

<400> SEQUENCE: 8

```
agacctcgtc ttcgccacgg tcaaggagaa gatcggctgg cggcggttcg tggaagctat        60
ccaacggtac gtggctgacg cctacggtgc tttcctgaca ctcaatgcgg aaaccgcacc       120 cgtcggggt gacgaagata acgccgtcag tgtgctcatt gacactttag gcgaagaaag       180
ggctatttta gcagcttatc gggtggcgga aaagctatta gacgataagc cgctgccaaa       240
cgacggcgag aacaatgggt ccgaaaatcc ccgggacgcc gcgcatactt tgcggagag        300 tcccgaatcg gacgaggacg tacaaaaggc gtccgccgag agctctcccg acacaccagc       360
tcgagacttt accgcggaag ccgtaaccgt gtacatcgac tcggacggcg gttgcgagga       420
cagcagcgaa gaagatcagg aggaagagga ggaggacgat gaagaagaag acgaagaaga       480
agaagacgaa gaggaggagg aggaagagga ggaggaggag gacgacggaa cacccgagtc       540
```

-continued

```
taccccttct accgtcatcg aagcggcgaa tctctcgccg gtcggcaccg acgaaaagca    600
cggggaaccc gacggcgagc ccgatgatgg tgacaatgac gacggagagg acgagggaag    660
aaattctgac gaggatagcg gatactattg ggggatgac accccctgg  aattggttcg    720
cgatcgcggg acaggcgatc acggtgagcc agatagcacc gctccttccg acggtcctgg    780
ggaagctccg tcggccgacg gggtagacga ggagcaggag caagacgaac aagagggaga    840
gaccgccgtc cccgccgcca ccgctcagcc cgctttcgac aaatgcctcc aacggcaagc    900
catgatgctc accggcgctt tgaaagacgc cttacccgag caggaacgcg acgtgcccct    960
ctgcgtcgat agcgtgcaat accagctcga gcgctacatc tttaaccccg atatgcgtgt   1020
ccctccggaa taccgcgaag tgcgctttaa cttctatccg cccttcatgc gccccaaagc   1080
gatcgcgaac taccacattt tcgccgtcac ggcgcccatt ccggcaagtt gcaaagccaa   1140
ccgcagcggg agccagctct tagaagcttg tcgcgacatg aaagtgttca agcgcttacc   1200
tcgttggcgc ctcaacgtcc aatccgacga cgggctcggg gacgaagtgg tacctgtaac   1260
agagctgaca gatgccaaat tagtccctct caaggacgac atctcgcggt tgcagtgggc   1320
taaaatgcgc ggtgaacaca tccgcttttt tagctaccct tccctgcaca tgcctcccaa   1380
gatctcacgt atgctcatgg agtgtctgct ccaacctttc gcaaacgaaa acgacaaggc   1440
ggaacaggtc gcccctgcg  tgagcgaaga ggaaatgcgt tttattgtag atccggagca   1500
gagaatgaga ggcgaggaac tctacaaggc catgctcaaa aggagggccg tcgttaccat   1560
ggccgtgcgg tacaccgctt tgctcgagct catggaacgc gtcttccgag agccttcctc   1620
cgtcaaaaaa gcccaagaag tgctccatca caccttcat  cacggcttcg tggcccaagt   1680
gcgcgaaacg gccaaagtga acctgagcaa ctacgccacc taccacggcg tcacctacaa   1740
cgacccgctc aacaactgca cgtcagccaa gcttttcgaa ggcagggaca aggaggatta   1800
cgtgctcgac accgtctacc ttttcttggt cctcaattgg caaaccgcga tgggtatgtg   1860
gcagcaagcc atcgatgata ccaccctgga catctacgcg aaagccttta cgcgccagcg   1920
acgcgccatt tacggcctcg gaagcgtcac cgaggtcagc aaggccatcg tcgacatcct   1980
gatggacggg gacaggctca cggaggaaat gcggaaagcc ctccccaact tcgtgacgca   2040
gagccagatc tccgatttc  ggcactttgt caccgaaagg tcgaacgtcc cctccatggc   2100
cgccccgttc taccctccg  atttcgtccc gttggctttc cggcaaagcg cccctctgct   2160
ctgggaccag gtctacctcc tccagatcgc ctttttcctc accaaccacg gaggatacct   2220
gtgggaaccg cccgagagcg aagcggaggt gccgcagcac cgcacttact gcccctgcaa   2280
tctctgcagc ccgcaccgca tgccggcgga taacgtcgct ctgcacaacg aagtgctcgc   2340
catcggcact ttcgagattc gcagcgccga aggcaaatct ttcaggctca cgcccgaact   2400
ctgggccaac gcctatctcg ataaattcgt gcccgaggac ttccatcctt tcaccgtgtt   2460
ccactttccc gaaaaccgct cttccttcac caaaaatcac accggttgcg tcacggaaag   2520
tccggaaatc ctctctctga ttcgtcagat ccaggcctcc agggaggagt ttctcctccc   2580
cgagcaaggg gctctacaaa gacccgcaga ccggcgaaac gctcaccact tcggtcgggg   2640
cagagaaccg tcctggagcc tccggcggag cgcctctacc gcccgctgcc gccagtacct   2700
gcggaggagc tcgagcgccg ccgaaacctc ctagggctct acggtctgcc tgccctgctg   2760
cagacccgga ctcccagagc gactacgggg aagctgctct cgcgtccaac tacggccgat   2820
atggctcaga ggatgctgga cgagaaaatc agagttaccg aagaccctcc ggaacccgag   2880
aacgccgttc ccttccctac ggacgcccgg ttcgtggggg ttcgcccgtg cggaggacct   2940
```

```
gaagtgagcg aatcagacgg agaaacgtta gaagccggac accgagagat ctgagtacca   3000
tctcggagag gaggaggacc tcgaagagat ggagaaagag aatatcccac cgcggccctc   3060
ctcgctgcct ctggacggga cgcggaaccg caagcgccgc tccgcatcct cgcccgggaa   3120
ggagctgaag aggcctccga tccgaaagag agccaaatcc gataaagacg cggagaccgc   3180
gcccgcgtcc aaaaagcgcc gtcctcgagg taactataga agctgggtca ggcaccgcgt   3240
ggcgatctgc caagcgctcc gcgacgccgt tttcgaccga aggctggcgg ccgaaatcct   3300
aaagagagcg cgcggtatct tcgtaccgcc caccgtattg ggctactacg cccgcaaact   3360
cctagaactt cccgacgaag atcactgatc gtcggctttt tctttctcct ttccttctta   3420
gcggctcccg ctaccgcctc tgacacgctc cctccgcctc tccgccgaa aaaacgcccc   3480 aaaaatacgc cgcggaccga ctcgtccttc gaattggtcc ctcccgaggt cgcagacttg   3540
aaagccaaca tcctcgacgt gctcgtcgaa atcgaaaata tcgccaaaaa cgacccttca   3600
cggcgcgttt ccatccgcaa ccgcacccgg gaaagcatca ctcggcagtt acactacgtc   3660
aaggacgagc aaaaactcac caagcttaag gcagatgcgg aaaaaatcct gcacctgtgg   3720
aaatcccttt cctaatcccg cttcttttat agcgctacag accgcgtgac tgagcccgcg   3780
gcaacatcat gaacctcctc gaagccactc ctaccgagta cgtgtggaaa tacaaccccc   3840
tctccgggat tcccgccggc gcgcaacaga attacggagc gaccataaac tgggtggtgc   3900
ccggaggtaa cagtttcgct tacgcggcgg acgagataag acggcacacc ctaagccctg   3960
ccgccacccg cgcgatcacc gaacgtttcg aagctgagtc agaccagcaa cccttcgcca   4020
acgcccggga aaccgcctac atcaccgcca acgtgctgga ctctggcttt ccaaagtccg   4080
ccgtgtaccc cgtggaccct tccggagttc aacgggttca gctctcgggc ggcgccgagg   4140
gccggatgca actcgcgggt ggcctcaccg aaggtcgagt gcaactttcg ggaggtgtcc   4200
taggacacgt cgtgcctcct gggggagaa gacgcgccgg cgggcgtccg ccgcgatggt   4260
gtgggaccgc tctcgcggga aacgggcttc ccgaggacgc cgaagtggtt tcggatacct   4320
acaagtactt cctccgcacc cagggaccca gccaagtcgt gcaagaaccc ggcgtgtact   4380
cgcggaggca gttcatgacc accttcctgc cggccgtggt gccccgacct ttcagcagtc   4440
ccaatccgcg cgactttccc gcgcagtaca gcgccatcta caaaggcacc aacgcgtacg   4500
aggacgtatt ttgggactgg tgaagtccct cttcgcggct tacccgttgc tgacggtgct   4560
ctgtttcgca ataaagttct tccaattcag cctcgctgaa cggttccgc ctcgttattg   4620 tcacgcgttc gcctccgtcg ctcaccacgc gcgcgcgaaa ccgtcttttg atccaaaaga   4680
cgtaaccggg gtttagggt tgcgcaaacc tcacgatcgc ctggtcgttg actttcaacc   4740
aatatttttt aggagcctgc gactccgtct ccgacatggc gacctcgact cctcacgcct   4800
tctcctttgg ccaaatcggc tcccgaaaac gccctgcggg tggcgatggc gagcgagacg   4860
cctccaaagt gccgaaaatg cagaccccg ctccgagcgc gaccgccaac ggaaatgacg   4920
agctggacct ggtctacccc tttggctcc aaaacggctc taccggagga ggcggcggcg   4980
gcggttccgg tggaaacccg tccctcaacc cgccgttttt ggaccccaac ggaccctgg   5040 ccgtccaaaa cagcctcctg aaggtcaata ccgcagcccc catcaccgtc accaataagg   5100
ccctgacact cgcctatgaa ccggagagtc tcgagctcac taaccaacag caactggcgg   5160
tcaaaatcga ccccgaagga cctctgaaag ccacagaccga gggaatacag ctgtcggtcg   5220
accctacgac gttggaggtt gatgacgtcg actgggagtt aaccgtgaaa ctcgaccccg   5280
```

-continued

| | |
|---|---|
| atggcccct ggattcctca gccgcaggaa tcacggtccg agtcgatgag accttgctca | 5340 |
| tcgaagatgc tggatccgga cagggcaaag aactcggagt caatctcaac cccacgggac | 5400 |
| cgattacggc cgacgaacag ggcctggact tagaaataga caaccagaca ctcaaggtca | 5460 |
| acagtgtcac cggcggggc gtcctagctg tacaactcaa atcccaaggt ggacttaccg | 5520 |
| tacagactga cggtatccaa gtgaacactc aaaacagcat caccgttact aacgagctc | 5580 |
| tggacgtgaa agtagccgcc aacggacctt tggaatcaac cgacaccggg ctcacactta | 5640 |
| attatgaccc cggagacttc acagttaatg cgggcacgtt gagcattatt agggacccgg | 5700 |
| ctctcgtagc caatgcgtac ctcacatccg gcgcctccac ccttcagcaa tttacagcta | 5760 |
| agagtgaaaa ttccagtcaa ttttctttcc catgcgcata ctatctgcaa cagtggcttt | 5820 |
| ccgatgggtt gattttagc tccctctatc tgaagctcga caggcacagt tcacgaacat | 5880 |
| accaacgggt gaaaattatc agaacgccaa gtactttacc ttctggggttg gagcgggcac | 5940 |
| ttcatttaat ctttctaccc ttacccaacc cactattaca cccaacacca cacaatggaa | 6000 |
| tgcattcgca cctgctcttg attactcagg tgctcctccc ttcatctacg acgcgtcttc | 6060 |
| cgtagttaca atttattttg aacccaccag tggtcgactg gaaagctatc tccccgtcct | 6120 |
| taccgataac tggagccaaa caacctacaa ccccggcacc atcaccctgt gtgtaagaac | 6180 |
| ggtaagggtt caattgagat cgcaagggac cttcagcact ctagtctgtt acaacttccg | 6240 |
| ctgtcagaac gcggcattt taacagcaa cgctacaacg gaaccatga ccctgggtcc | 6300 |
| tatcttctgt agttatcctg ccttgagcac cgccaacgct ccttaattca ataaaaaatg | 6360 |
| atccacacaa tatgaaggtc tactgtgatt ttttattaaa gcagccatac taattctcct | 6420 |
| ggatacccat cagtctgtcc cactctccgc gttgccagta gtacaggcag ttcacggcgt | 6480 |
| ccacgtacca cgattcgctc accagaaaga cccgctgctc gggaaaatcc accatcattc | 6540 |
| tgcggatgta gtgacaaggg agcgcccca tctggccgag cgtggccacc gcttccacga | 6600 |
| acacaccggt gttgtgcgga gggacataga tgatcatgcc cagaactcct ccgcgggcgc | 6660 |
| ggcgcagaag acgggataaa attcggtaaa catgacagag gcccacgccg ctacgaagta | 6720 |
| cacccttcc agactagggt cgccttccag cctgctccaa aggtacacgg agagaccact | 6780 |
| gctgtcgggt tgactgcaca cggccatcgg cacgcgtctc atctcgaatc cgtggcagtg | 6840 |
| acaccgctcc ggaatcatct cgaattcttc caaacataga aactggtgcg cgtggacggc | 6900 |
| cggcacgaaa cgcaaatctc cttccctgc tccaccgcg ggttgatgtt ccctatgtc | 6960 |
| ttcgccccat aacctctgag cggccatgat ctacacctgg gattcttcgc gctctatctc | 7020 |
| agtatacacg tgttccacag agccgccgta gacctcttcc tcgtcgctac ctgccggtgg | 7080 |
| cgctctcagc aacgacagtt ccagtggtgt cggcggcggt ggaacagaag gaggcggtga | 7140 |
| acgggtatcc gagcgggagt cgtaaaacgg attgctgctc acagtccaat tgggggaacg | 7200 |
| agcgggaaac tgagacaggg aacgcagcca ggagaaccga cgtgatggct cgcggttatt | 7260 |
| aggcaatggt gggggtaaag cagaacaccg gcgacggata ctccaacggt gtcctcggat | 7320 |
| gctcttgagg acctcccgca atgattctcc gccactgcgc gatcagcaat acaaacgcga | 7380 |
| tcgtggctag aagagtgcaa cagccaaaca tcataaacac gtagggaacg gcatgtaaat | 7440 |
| attgactgag gaagagataa ctggcggcca ccgcaccgca gtgaatgact cccacggtca | 7500 |
| cagccagaag cagcagaagg catgcctctc tgcggcgccg gcggatccgc acctatcaat | 7560 |
| agaaaaaagg ggactttcta tcaccctcca cgcgtgcccg gcgcttggac atgcaattcc | 7620 |
| gcaaatagga caactgagct atagtggcta ggggcaaggg ctgtctaaga gggcatccgg | 7680 |

```
ggcaagaagc ttcggggtga tggtcgcagt acgtgccgtg aacatgcagt acccattctt    7740
ctacatccac aaacgtggcg gtacgggaag cggaatgtag cataaccccc gcgacaccat    7800
gctccagcaa gcggggtcgg ccatctcttt cagcatggat cgggtcatca gaggctgggt    7860
cacgggactg cccttcccgc aagttttaag aatgacggtc gctaccacat tggtgcgaca    7920
cgcacccaga tagagaacgg gatatttcaa aaaaggcagg tgctcaggca cgaccgtctg    7980
ggaaacctca taacataatg attgaagagc caaccgaaag gcaacaccgg tctctagaac    8040
gagtcccgta tctacaaaca gaaagtcggt tttgtttttg cgaaccatcc attcccgatg    8100
tttctctatc agaggttccc gcgctacgaa cagacgcctc gaaaccgctc gcaggatctc    8160
ctccttttcc gcgggtgata aagacaaccg agactgcagt ctcagtatga cgttcaacag    8220
aacgcacggt cccgtcttga gtctgagata cttcgaacac ctgcagctca ctaccgtata    8280
cagggactcg tgccacgagt aatgctgggg tttatcgaag agactaatgg aggctacgga    8340
acggctcgtg tgatactcca tcatgcgttc cgctgcttct tgggacggac cctgtctgac    8400
caggatgctg aaccatatgg ctccgcattc gttttgatag ccgcaaccgc gggtaacggc    8460
aaccacctcc tacacgaaag aaaggggcgc cttaagttac tcaaggaaac cgcccgggaa    8520
aaatcggggc aatgaaaagc tatcactcac cgaatcagaa cacagaggca tgatgcgtaa    8580
ctaagacagc tcttttattg atcaggtacc gtcacctgta aagatacaca cattaaacga    8640
tacggtaaga gtcaccgcgg taacaccgac atcggtagtg gcagaatata tagagcacga    8700
ctgctgtcgt gaacagagca gctacgacac cacccgtaac aatcgcgagg cgcgcggcat    8760
cgtcttccca aaattcacgg atcagagagt agaactctcc tccgagctga ggagacgtag    8820
ggaaggatcc cgtagaccca ttgctacttt tttccgtcgg atagcggtag agaccaacac    8880
agctaccata gccaaaaaca caagccccac aaccgttaaa aaaagagttc cggtagatgc    8940
acccgaggcc gctactcgag agccctcgtc tatggctcgc aaggcgacgg cttgaaccgg    9000
ttcggtttcg tttagctgga cggtcactac ctcctcttct gacgcggttt ccgaagtgct    9060
ccaaaaatcg cttgaactcg gtgtagctgc tgagaaattc caggtcgaaa cggtcgatgc    9120
ggagtctgtc gatgtagagt tcaaagacgc agtaggttct ggcgggaact ccacagaaac    9180
gggttccagt gggcttaccg ttaccttcaa ttttataact tcaaattcaa gaaagaattc    9240
cagttcgaat acgtcggcat taagaaggt gacggtaaat tctttcttca ttctgtccaa    9300
ttggaagaca cactgcgcag ctgtctgaca cacgtcccag aaactgtaca gtttatgggt    9360
ccccgaagaa tccgtaagtt ggatactcgt cagccagaaa ggagacttgc taagatctac    9420
cttgagtcca tgtcccactt tcacttctac atcagccagc tggatcggaa tcatagctat    9480
cgaggcatct ctatccgcca ggcaaccaga ctgaggagga acactgactt gagatccgcc    9540
gttcggattt aacatcgtgc gataactcat taggggaat cgctccttgg ttaccatgca    9600
gtagtgcgca ggccgaccga acggatctct tgtagggtta cagtgcatgg tacgcacaca    9660
ccctccagtc attactttac ggtcctttat cgagggagcc cttgacgaat cctgatagaa    9720
tccctgtggt gtgatcacgt acaccaggta gatacttgca gaaggattcc agtgacggat    9780
ccacaacacc tcttctgcaa gctcggtgta acccaccgcg gtaagtacat catacctccc    9840
ataccgaagt gtttgctcac tgtaacctcc gatgaacatt cgactcccac tagaagctac    9900
tactatgatc atgatcggag ttacaaagtc ctgcttgagt acgggtgagt acgtaatctc    9960
agtcatgtag ctaatgctaa tatgattgaa gtagctagcg tatctgtaat ctcgactcat   10020
```

-continued

```
agtataccca ttccaagtgc tccggacagg acccactttg aaaccctcat taagcaagtg    10080
aaacatgggt aacccagttc tcacatccaa agtctttaga aacttcggta ctatcaatct    10140
atgaaaacag ccgcttttac tccacgtatc cctccatgag aattcttcgc agaccgtctg    10200
tccccataca ctttctgcac acactcttcc cgaccatccc ccatgaatcc cacaacctct    10260 accgcccttta tcctccaaca tgatatcctc agaagccgta taccctcctg taatccacga    10320
cccttccgtt ttcaggactg ccacgtaatc cgcatcattt ttatctaagc ctccggtaac    10380
aaacgtgggc tctaacccga ctattctggt acaccgtcta tccccagaaa tatatgtcca    10440
ctgtctgcag atagtagagc aagcgtgagc gccggcagaa tgtcctatac agtgtaacct    10500
tttcgaatgt ggtatgtccg acagaaactt cccgaaatca acatacagac cgtcatagtc    10560
gtagtacagg ttccagtcca ccaggagcag cgcgactgca ggcgtcatat tctgatggac    10620
acgcaacacc tgtctaaaac tttgatagcc catgtaatac cccggtataa gcacaatgat    10680
atcggtcttg ccggctaaag cactgtgcaa tcgatggtag acaccgtact ggtacgtcac    10740
gtcgtgaaat ttcggcacac ccccgtgagc tccataccac gtaatcttcg atggcggtcg    10800
gctcaatctt ccaacgcctc tcggagcatc aagtttttaga gaatccggtc tcgccacgca    10860
tgaccgattg cccgaatcgg gacatgcaac tgccgatttc gcacgcgaaa gcacggaggc    10920
tccgaagagc accccgacca actgaaacag aacgcatgat ttagacccac tcccgacaga    10980
ggattaacgc gacccaatca agggatatca aaaagaatc cttaccgcgg agagattcat     11040
agaccgaaga gttgagagcg ctcctgtttc tctgaagatc tctcaccccg actgtgacag    11100
atccacaaag cagcactcaa tttatactgt caaatggtta atgtttaatg ctagaaaagc    11160
gctgacaccc agtaaatatt tacttagttt gcagttccac tgtttcctta ttgccatgac    11220
tggacaaaaa ccacagataa gatgttccat tcaagggaac ccgatgttcc ctcgataact    11280
tcccggtaca aagtccaaaa atagaactag gtgctttata aatactaaga gtcgactcct    11340
tggtgtttca gaagaacaca gacgatctac aaacaggatg aacctcggaa gactcaacac    11400
cgccggtaag aacatcttaa tttttacttt gtatgatttt caattctgaa aaacacgttt    11460
cctggttcgt gcacgtacgc ggaaacgaag ttcgaaaaat cagagttgga attttccagc    11520
tatggttaac tattaactat atgacgtcac ttagttaatt attaacgata taagtaaat    11580 gattaactcg ggctagttaa tgattaacta tacctggtta atgattaact gacttagtta    11640
atgattaact agaagttaat gattaactag aagttaatga ttaactagaa gttaatgatt    11700
aatctattac gtcactcgtt atatattaac tagtgacgtc actcgttata cattaaccca    11760
ttacgtcact cgttatacat taactagtga cgtcatgagt aaatcattaa ccttcatgca    11820
tatgcatgag gagctactga atatgcatga gagcctcata catatgcatg gaacttatgc    11880
atattcacga cactcatgca tatgcatgca ttggttaaag agtaacccta tgactcagtg    11940
tgtatgttta cgttgcctag caacgttaat gatttacctg ctgacgtggc agctccgcct    12000
ccaggtaaat catttacctg aactttgttc tttatgttta ttcaccatgg caacgctacc    12060
atatatggac atccgactcc gcctcccccg ttatacatta acgatggcgt gataggcgga    12120
gctctccccc attggctctc aatgacgtag ttcaggttaa ccataagcca gaaccgccta    12180
tataggtaga gcaggtagac ccggaacacc attcccatcc ggacctccat agagtgcgga    12240
cctctacggg ctctccatac cggtaaatat tttattccat ttaatccaat cgaataaatc    12300
aataatcaac tcaatgctgt gattctgcct caaattcaat ggtgattttc tttaataaaa    12360
agcccacccc ccttggcacc cccctgtaca ccccccctgta caggcgacca cccccctatgg   12420
```

```
acaccccct gtacaggcga ccaccccta tggacacccc cctgtacagg cgaccacccc    12480
ctatggacac cccctgtac acccctgt acaggcgacc acccctatg gacacccc       12540 tgtacaggcg accaccccct atggacaccc cctgtacac cccctgtac attttctccc   12600 ataggctaca atggaatact gccccctagt gtctcctgct gtatgggacc cctatgatgt 12660
gggcgccatt acctttgcca ctatggagct ccttcacgag gggcgccat tgaaattggg  12720 agaccgcata gagagcctag ccaatggggt gctttggaat ccggatatcc ccgtccaact 12780
cttcaactgc ctttccattc gctcatgggg atcacatggg aagcgcgtca tgtaccgtgg 12840
ccacacctac cggatgtacc acgcccagtt acgggtccga agctccgccc ccgttactag 12900
gaaacaggcc ggaagcctgc tcctcagcct atcacagaag ctcctctgtt tcgccgcccg 12960
ctttaatacc catccctcg tgatgcaatt ggggtggag tctaaccta tgggcctacc    13020 tgtatatacc aagagggccc tccagatggc gctacagagt atgcgggtgc gcattgcccc 13080
tgacggccag aaggtggcgc caccggagat aggcaagacc tgtacggtga agcccctcaa 13140
gaccccggag accctccagc aggggtctt cagtaccacc gatttaaaaa agacacttcc  13200
agattgggct tttcgccgac tttttaacca aacccctat atttgtggat ggaagattgg  13260
caccgcgcca gaaggggcgg agagttggat cgttacgctc caccccagc cttcgactcc  13320 gccccccaca gggaccaaga ctccgcccac tctgcaggac cttgccggc tgggcgtggt   13380 cgagcaatgc ctcaagatga ggaggcgtgg cctggaccgc aggcaccacc cctatgctca 13440
ataaaccaat cagattccag tacttggctc ctcctatttg tgggcgggac tttgcacgcc 13500
tcttagcggc gcccctggc ggccgaggc cgccactgca ccctgtcgg acttagtctc    13560 tggcgcgggg ccggtcaatc attaacccga cggccggcac gggcgccccc tggcggcggg 13620
cgcccgccac tgcaccctgc gcctcttagc ggcgcccct ggcggccgag ggccgccact  13680
gcacccctgt cggacttagt tctggcgcg gggcggtca atcattaacc cgacggccgg   13740
cacgggcgcc cctgcggc gggcgcccgc cactgcaccc tgcgcctctt agcggcgccc   13800
cctggcggcc gagggccgcc actgcacccc tgtcggactt agtctctggc gcgggccgg  13860 tcaatcatta acccgacggc cggcacgggc gccccctggc ggcgggcgcc cgccactgca 13920
ccctgcgcct cttagcggcg cccctggcg ccgagggcc gccactgcac ccctgtcgga   13980
cttagtctct ggcgcgggc cggtcaatca ttaacccgac ggccggcacg ggcgcccct   14040 ggcggcgggc gcccgccact gcaccctgcg cctcttagcg gcgcccctg gcggccgagg  14100 ccgccactg cacccctgtc ggacttagtc tctggcgcgg ggcggtcaa tcattaaccc   14160 gacggccggc acgggcgccc cctggcgcg ggcgcccgc actgcaccct gcgcctctta   14220
gcggcgcccc ctggcggccg agggccgcca ctgcacccct gtcggactta gtctctggcg 14280
cggggccggt caatcattaa cccgacgcc ggcacgggcg ccccctggcg gcgggcgccc  14340
gccactgcac cctgcgcctc ttagcggcgc cccctggcgg ccgagggccg ccactgcacc 14400
cctgtcggac ttagtctctg gcgcgggcc ggtcaatcat taacccgacg gccggcacgg  14460 gcgcccctg gcggcgggcg cccgccactg caccctgcgc tcttagcgg cgcccctgg    14520 cggccgaggc cgccactgc acccctgtcg gacttagtct ctggtgcggg cccgagtcac  14580
ggatggagta gtttccttg cggccagcag agggcatacc tttattctca gctcgcaagt  14640
ctcaatagat acacacctca tcggtgtaca gcgtgtccgc gtagcgcagc cccgtgcacc 14700
tcacccaacc acctatatcg cgaacggctc cggtactcac tatgtatttc ccgacgcgat 14760
```

-continued

```
agttcggatc attgcaccac ttattcaagt acattctaaa ccattgccct tcggggactt    14820
ggcgctgata aaacattcc ctgaagtacc gtttcaccgc gcgagaacac ttatacaagt     14880
atctgtcccg caggttgaac atggttaagc acagaagcaa ggtcatgtgg caggaacaag    14940
aaccgccagg ctgcaacccc acgcagtatc ccatcggatg accgatctcc gagttcgcct    15000
cctcgtggaa cgggtaccat agctgcttca cgtcttgaac cagcttccag aacactgcat    15060
cgtgcataca ccacggcggc acggcaactc cgaagatcac gtacagtggc atgttccgga    15120
tacatctacg acacaggtac tgtgacacct tgcgcgtacg cgaaaaggga acccgaccct    15180
cccccgtaac gctccactta cggacagccg gcgatgcgca ctgcgaacga aaaataaatc    15240
tgcgccgttg tgcgctccag gcggaaacag gggaatatat aagccaactc ttatctttat    15300
tgttgccacg cccgacacta tccagatttc gagacctgct gacaccaccg gaacacgcga    15360
cctcgccctc tctttatcat ccatacgccc aggtgactca gtcaaatccc ttatataaag    15420
accgttttta cctgaccgct tccacgtaca caaggcggca catgaaagca ccatgctgcg    15480
ccccgtatcc gccatcgcgt tcctctcgtg cctatgtctc acgcggaccg cgcaacaggt    15540
cggtaagtcc tttaatctta cgacccactc caacctcact gtgcacccgc agaccaaagg    15600
aacctcaaag caagagtggc ggctagggcg cgataccaag attgcgatgt gggagaaagg    15660
ctacgggtac agctacccgt cgggacccct taaaggccgc gtagaaatga acgagaccag    15720 tgtcacctt tttgacctcc gtcccaacga ttctgccata ctgacttact tctccgaaga    15780
tagctccggc acgagagtg aatatccgta cgccatcagc gtaagaggtg agcccttccc    15840
tacctttgtt ccattccgcc catcgagcac ctcagccgac accacacatt ttcagatccc    15900
ctccgccctc ccattctacg gctgatgact aacaattccc gtccgcggac cgagagccgc    15960
atgagcttgc agtgcatcgc gctcgataac gatagttcca ttacgtacgc ctggtacact    16020
gacaccttag agagcgggga caacatccga gaagtaaccg tccgaacgga ttctgaggta    16080
gcagttacct gtcggatatc ggatggacat tccaccaatt ccgcgactct cgtcgtgccg    16140
ctaaaccgag tcagtaata tccctccct caccgcaaca gatccgcaca gtcaggatcc     16200
caggctttca cgatccttc cccactcctt tagaacctgc cgctccctac ggcgcggata    16260
tgactacggt gttcctggcc atcttagccc ttattcttct aaccgtcatc ggcggctacg    16320
ccctcagaaa gctgtgtatg cgaaacgagc gcgtttttat ttgtaacccg tacagagaat    16380
gttttggcgg tcatctctag gacaaataaa cttctacttg aaatgagttt attttttcccc   16440 ctgcctgttt gtgatgggaa atgatcggtg ctgcttatgg accgagatag atggaaggga    16500
cgggggcatt caaatttcta ggtccaggga cataaaaaag agatcaaatt tacatctccg    16560
gtaaagatca cctctataac cccgctgtga atcccagcac tccctcccga tacgcaaact    16620
gactagcagt tcctgtgtat agacaaacgg aatcctggtg tacagacaaa cggaatcctg    16680
agttcccaac gcattcattt atttgaatat ttacacattt acacactgta cacggtcatt    16740
cgatttcatt gccaacagaa agactaatcg atgtccccct tcagtatgtg gactgtgaca    16800
gcagggtctt cgctcacttc actgtccgtg tcatcctctg tacgcccaca cagcatcgcc    16860
cgatagtgaa agctgacact cagcatggag aaccaaacag cagggagcaa tgtgagaggc    16920
agccaacaca gggaaacttt tttcttctcc cttcagaccc cctcccgtcg agacattgtg    16980
atggactact ggtacttcgc cctgatgttc ccaggtagga acgaccgtaa gggtgaacct    17040
ctgaacgctg ttctgcatca ggtcccgtgt cacttgatac atgccggaat ccgcgccact    17100
taagttcttg atagtcacgc agttctcgga tctgttatac gacagcctcc cttgatacgc    17160
```

-continued

```
cccgtagacc atcggctcct tcagcgcctg gtagtcctgc agcacgaact tgcgcacggc    17220
gcccgcatcc accgcggtca cttcccattc tctgatctga aaactctcgg tagaaccgca    17280
cagagtcaca gcgtcccgtt cgttagccac gacccgggat acgttctcca ttttcaccgt    17340
accgttctcg ggaagccccg acacggtgaa atatacagtc tcgggcttgg aacccaccgc    17400
gaatgattgt gatagccagc acccgttatt agctttgatt gcttcgacat gcattgaatt    17460
acaggatgaa tttagccgcg ccctcgtcat atagcccaga tccagcccct ctttgatcga    17520
aggaatcacg aaagccactt tctgccatct gttacagacc ttccccggag cgtggtacca    17580
tagcagcagc gtgaaatcag cgcatctgcc cgtagtcaga gtcacctcct tacggcccct    17640
cacggcggca ccggagacgg tggcagacaa gcagaggacg gcggcacaca gcaggagcga    17700
gccatgactg cggagtccga gccgagcggt gtgctgctcg atcctccgct acctttttat    17760
gcaccaccca ccttttattgt cggtcacaca ttaattcgcc ccgtcagcaa acacgtgagt    17820
aacgtatgcc gttgttctga tcggtcagca ccgcgcccgc gacgtttgaa cgaagacgta    17880
cggtgacttc cgcataggga gctataagga agtcagttag gaaaaatcga tcctcgacac    17940
accccacgga aacgctgacc taggcgaaac ctatcaggta aaacattcac tatacgcacc    18000
acgcgttgaa taaacagtta acccatacgg ggtatatatt ctaccccgac tgcagtcagc    18060
gatcaggacg cgtccacaga gagatccgtg cgcgaccgcc tgtccgggct cctctagaat    18120
caagaattcc ataaccatgc aggtaagaac tcctttctct tcctcctatt tgatccgagc    18180
ctttttttac gctactcaac cgcaacccgt ttcttccacc acagttactg ctccttctat    18240
gcctttgccc tctgatgggc agcggaacac tagcaccct cgtctcggta gacaactcct    18300
actccgtgtt cggatccggc aaacccccac tttctacctc cgaatccgcc accaccgcct    18360
actccgaaac cgcggttccc gaaaactctt accccccatcc gaagccacca cgccctgcga    18420
cgacttgctg gaagaggact gctggttcgc ggagagcagc gcggactacg cacccatacc    18480
ctggaacacc aaagagaata cgtccgtggt tatcccggca caggtagccg tctcgccatc    18540
gcagtccact actcccctg cggtcatgct cggcatcgca cagaaagccg taaaccgcgg    18600
agcctccagc aaggatcaca cgtcccatat cgccacgggc gttaccgtag ccggaatagt    18660
catactcatt gccctcgtca tcatagcctt ccgtacaaag gttaaggaac cgcgcccaac    18720
ccgctccatc tacctgggcg tgcctccccc tgacgttaga ccttaccgta taatagagca    18780
ataaagattt ggccgccaca tcgcacaaga atctttccgt gtcctgtgtc tgtctcggcg    18840
ccgtccgcgg gaaaaggtta acgcggaatc tatttccctg cggatttccg tatccgtcag    18900
ttcctgggcg tcgccgaaaa tgctcacgga agacacgccc atgcgggcgt ggctaaccga    18960
tgattcgaaa aacgattcgc gagcgccctc tgccggcggc ggcgggaata gggggtgtgg    19020
ggggagtgta ttttaagtag atatatatag atgatg                              19056
```